US007217566B2

(12) United States Patent
Cates et al.

(10) Patent No.: US 7,217,566 B2
(45) Date of Patent: May 15, 2007

(54) ATTACHED CELL LINES

(75) Inventors: Sharon Cates, San Diego, CA (US); Valentina C. Ciccarone, Gaithersburg, MD (US); Dale F. Gruber, East Amherst, NY (US); Pamela Hawley-Nelson, Downingtown, PA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/805,536

(22) Filed: Mar. 22, 2004

(65) Prior Publication Data

US 2005/0124067 A1 Jun. 9, 2005

Related U.S. Application Data

(60) Provisional application No. 60/529,405, filed on Dec. 15, 2003, provisional application No. 60/456,550, filed on Mar. 24, 2003.

(51) Int. Cl.
*C12N 5/10* (2006.01)
*C12N 5/08* (2006.01)

(52) U.S. Cl. .................. 435/369; 435/366; 435/325; 435/455

(58) Field of Classification Search .................. None
See application file for complete search history.

(56) References Cited

U.S. PATENT DOCUMENTS

| 5,547,932 | A | | 8/1996 | Curiel et al. | |
|---|---|---|---|---|---|
| 5,683,903 | A | * | 11/1997 | Lysko et al. | ............ 435/369 |
| 5,863,798 | A | | 1/1999 | Lysko et al. | |
| 5,919,636 | A | | 7/1999 | Lysko et al. | |
| 2003/0096414 | A1 | | 5/2003 | Ciccarone et al. | |

FOREIGN PATENT DOCUMENTS

WO   WO 02/090533 A2 * 11/2002

OTHER PUBLICATIONS

Yao et al. Laminins promote the locomotion of skeletal myoblasts via the alpha 7 integrin receptor. J Cell Sci. vol. 109, Pt 13, pp. 3139-3150, Dec. 1996.*
Robbins et al. Macrophage scavenger receptor confers an adherent phenotype to cells in culture. Biotechniques. vol. 25, No. 2, pp. 240-244, Aug. 1998.*
Roy et al. "High Transfection Efficiency of Cloned Cell Lines," Focus, vol. 21, pp. 62-63, Life Technologies, 1999.*
Cassoni et al. "GeneSwitch™ -It Stays Off Until You Turn it On," Expressions, vol. 6, pp. 1-15, Invitrogen Corporation, 1999.*
2000 Invitrogen Catalog, Invitrogen Corporation, 2000, pp. 111-113.*
Pear et al. Production of high-titer helper-free retroviruses by transient transfection. PNAS, USA, vol. 90, pp. 8392-8396, Sep. 1993.*

Harms et al. Interfreron-gamma inhibits transgene expression driven by SV40 or CMV promoters but augments expression driven by the mammalian MHC I promoter. Human Gene Therapy, vol. 6, No. 10, pp. 1291-1297, 1995.*
Cote et al. Seum-free production of recombinant proteins and adenoviral vectors by 293SF-3F6 cells. Biotechnology and Bioengineering, vol. 56, No. 5, Sep. 1998, 567-575.*
Elbashir, S.M., et al., "Duplexes of 21-nucleotide RNAs mediate RNA interference in cultured mammalian cells," *Nature* 411:494-498, Macmillan Magazines Ltd. (2001).
Finn, B., et al., "Hit the ground running: Ultimate Human ORF Clones--Sequence-verified and ready to use," *Expressions10*:16, Invitrogen Corporation (Feb. 2003).
Aiyar, N., et al., "Human $AT_1$ receptor is a single copy gene: characterization in a stable cell line," *Mol. Cell. Biochem.* 131:75-86, Kluwer Academic Publishers (1994).
Ashkenas, J., et al., "Structures and high and low affinity ligand binding properties of murine type I and type II macrophage scavenger receptors," *J. Lipid Res.* 34:983-1000, Federation of American Societies for Experimental Biology (1993).
Baek, S., et al., "Sustainable Systemic Delivery via a Single Injection of Lentivirus into Human Skin Tissue," *Hum. Gene Ther.* 12:1551-1558, M.A. Liebert (2001).
Bickel, P.E., and Freeman, M.W., "Rabbit Aortic Smooth Muscle Cells Express Inducible Macrophage Scavenger Receptor Messenger RNA That Is Absent from Endothelial Cells," *J. Clin. Invest.* 90:1450-1457, The American Society for Clinical Investigation (1992).
Buchschacher, G.L., and Wong-Staal, F., "Developmentof lentiviral vectors for gene therapy for human diseases," *Blood* 95:2499-2504, The American Society of Hematology (2000).
Dull, T., et al., "A Third-Generation Lentivirus Vector with a Conditional Packaging System," *J. Virol.* 72:8463-8471, American Society for Microbiology (1998).
Freeman, M., et al., "An ancient, highly conserved family of cysteine-rich protein domains revealed by cloning type I and type II murine macrophage scavenger receptors," *Proc. Natl. Acad. Sci. USA* 87:8810-8814, National Academy of Sciences (1990).
Gronostajski, R.M., and Sadowski, P.D., "Determination of DNA Sequences Essential for FLP-mediated Recombination by a Novel Method," *J. Biol. Chem.* 260:12320-12327, The American Society of Biological Chemists, Inc. (1985).
Invitrogen™, "Growth and Maintenance of the 293FT Cell Line," Invitrogen™ Catalog No. R700-07, Version C, Invitrogen Corporation, pp. 1-10 (Mar. 2003).
Invitrogen™, "Growth and Maintenance of Flp-In Cell Lines," Invitrogen™ Catalog, Catalog Nos. R750-07, R752-07, R758-07, R760-07, R761-07, R762-07, Version E, Invitrogen Corporation, pp. 1-16 (Feb. 2003).
Invitrogen™, "Growth and Maintenance of the Freestyle™ 293-F Cell Line," Invitrogen™ Catalog, Catalog No. R790-07, Version B, Invitrogen Corporation, pp. 1-11 (Aug. 2002).
Invitrogen™, "Growth and Maintenance of the Grip Tite™ 293 MSR Cell Line," Invitrogen™ Instruction Manual, Catalog No. R795-07, Version A, Invitrogen Corporation, pp. 1-20(Mar. 2003).

(Continued)

*Primary Examiner*—Celine Qian
*Assistant Examiner*—Jennifer Dunston
(74) *Attorney, Agent, or Firm*—Douglas A. Golightly

(57) ABSTRACT

The present invention provides novel cell lines that may have improved adhesive qualities, transgene expression level, growth rate, and/or growth rate in serum free medium or even chemically defined compared to cells of the prior art.

5 Claims, 40 Drawing Sheets

OTHER PUBLICATIONS

Kodama, T., et al., "Purification and characterization of a bovine acetyl low density lipoprotein receptor," *Proc. Natl. Acad. Sci. USA* 85:9238-9242, National Academy of Sciences (1988).

Kodama, T., et al., "Type I macrophage scavenger receptor contains a-helical and collagen-like coiled coils," *Nature* 343:531-535, Nature Publishing Group (1990).

Landy, A., "Mechanistic and structural complexity in the site-specific recombination pathways of Int and FLP," *Curr. Opin. Genet. Dev.* 3:699-707, Current Biology Ltd (1993).

Lewis, P.F., and Emerman, M., "Passage through Mitosis Is Required for Oncoretroviruses but Not for the Human Immunodeficiency Virus," *J. Virol.* 68:510-516, American Society for Microbiology (1994).

Matsumoto, A., et al., "Human macrophage scavenger receptors: Primary structure, expression and localization In atherosclerotic lesions," *Proc. Natl. Acad. Sci. USA* 87:9133-9137, National Academy of Sciences (1990).

Miller, D.G., et al., "Gene Transfer by Retrovirus Vectors Occurs Only in Cells That Are Actively Replicating at the Time of Infection," *Mol. Cell. Biol.* 10:4239-4242, American Society for Microbiology (1990).

Miller, A.D., and Rosman, G.J., "Improved Retroviral Vectors for Gene Transfer and Expressions," *Bio Techniques* 7:980-990, Eaton Publishing Co. (1989).

Mochizuki, H., et al., "High-Titer Human Immunodeficiency Virus Type 1-Based Vector Systems for Gene Delivery into Nondlviding Cells," *J. Virol.* 72:8873-8883, American Society of Microbiology (1998).

Naldini, L., and Verma, I.M., "Lentiviral Vectors," in *The Development of Human Gene Therapy*, Cold Spring Harbor Laboratory Press, Cold Spring Harbor, NY, pp. 47-60 (1999).

Naldini, L., et al., "Efficient transfer, integration, and sustained long-term expression of the transgene in adult rat brains injected with a lentiviral vector," *Proc. Natl. Acad. Sci. USA* 93:11382-11388, National Academy of Sciences (1996).

Ohara, O., and Temple, G., "Directional cDNA library construction assisted by the *in vitro* recombination reaction," *Nucleic Acids Res.* 29:E22, Oxford University Press (2001).

Park, F., and Kay, M.A., "Modified HIV-1 Based Lentiviral Vectors Have an Effect on Viral Transduction Efficiency and Gene Expression *in Vitro* and *in Vivo*" *Mol. Ther.* 4:164-173, The American Society of Gene Therapy (2001).

Pearson, A.M., et al., "Polynucleotide Binding to Machrophage Scavenger Receptors Depends on the Formation of Base-quartet-stablized Four-stranded Helices," *J. Biol. Chem.* 268:3546-3554, The American Society for Biochemistry and Molecular Biology, Inc. (1993).

Peng, K.W., et al., "Organ distribution of gene expression after intravenous infusion of targeted and untargeted lentiviral vectors," *Gene Ther*, 8:1456-1463, Nature Publishing Group (2001).

Sambrook, J., et al., "Assay for β-Galactosidase in Extracts of Mammalian Cells," in *Molecular Cloning: A Laboratory Manual*, Cold Spring Harbor Press, Cold Spring Harbor, NY, pp. 16.66-16.67 (1989).

Sauer, B., "Site-specific recombination: developments and applications," *Curr. Opin. Biotechnol.* 5:521-527, Current Biology (1994).

Seki, S., et al., "Differential Effects of Aphidicollin on Replicative DNA Synthesis and Unscheduled DNA Synthesis In Permeable Mouse Sacroma Cells," *Biochem. Biophys. Acta.* 610:413-420, Elseview Biomedical Press (1980).

Urlaub, G., and Chasin, L.A. "isolation of Chinese Hamster cell mutants deficient in dihydrofotlate reductase activity," *Proc. Natl. Acad. Sci. USA* 77:4216-4220, National Academy of Sciences (1980).

Yee, J.K., et al., "A general method for the generation of high-titer, pantropic retroviral vector: Highly efficient infection of primary hepatocyte," *Proc. Natl. Acad. Sci. USA* 91 :9564-9568, National Academy of Sciences (1994).

Yee, J.K., et al., "Gene expression from transcriptionally disabled retroviral vectors," *Proc. Natl. Acad. Sci. USA* 84:5197-5201, National Academy of Sciences (1987).

Yu, S., et al., "Self-inactivating retroviral vectors designed for transfer of whole genes into mammalian cells," *Proc. Natl. Acad. Sci. USA* 83:3194, National Academy of Sciences (1986).

zufferey, R., et al., "Self-Inactivating Lentivirus Vector for Safe and Efficient In Vivo Gene Delivery," *J. Virol.* 72:9873-9880 American Society for Microbiology (1998).

\* cited by examiner

Figure 1. The Human Macrophage Scavenger Receptor (MSR)

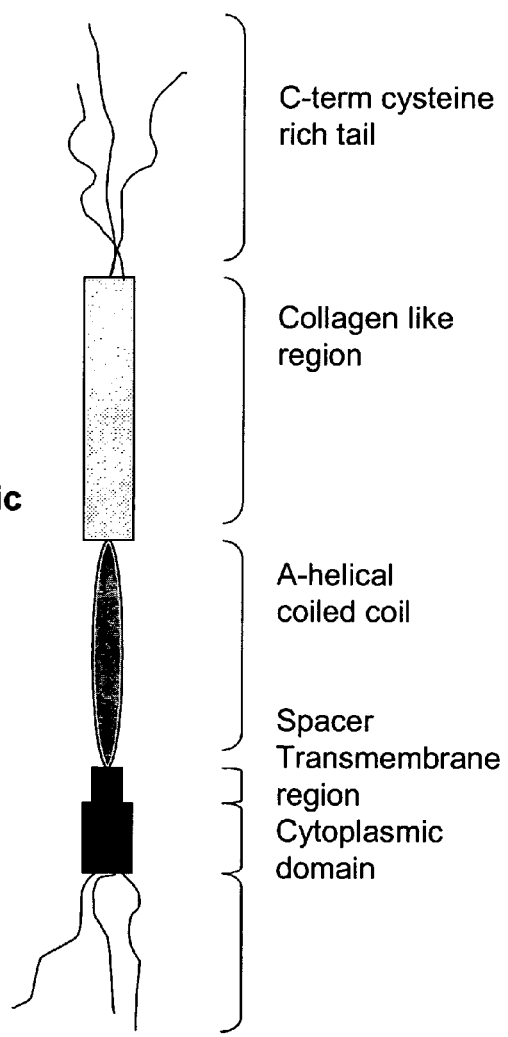

- Trimeric integral membrane protein

- Recognizes polyanionic ligands
    - Low density lipoproteins
    - Bacterial endotoxins
    - Lipopolysaccharides
    - Tissue culture treated plastic

- Implicated in the pathologic deposition of cholesterol during atherogenesis

- Implicated in host defense against microbial pathogens

C-term cysteine rich tail

Collagen like region

A-helical coiled coil

Spacer
Transmembrane region
Cytoplasmic domain

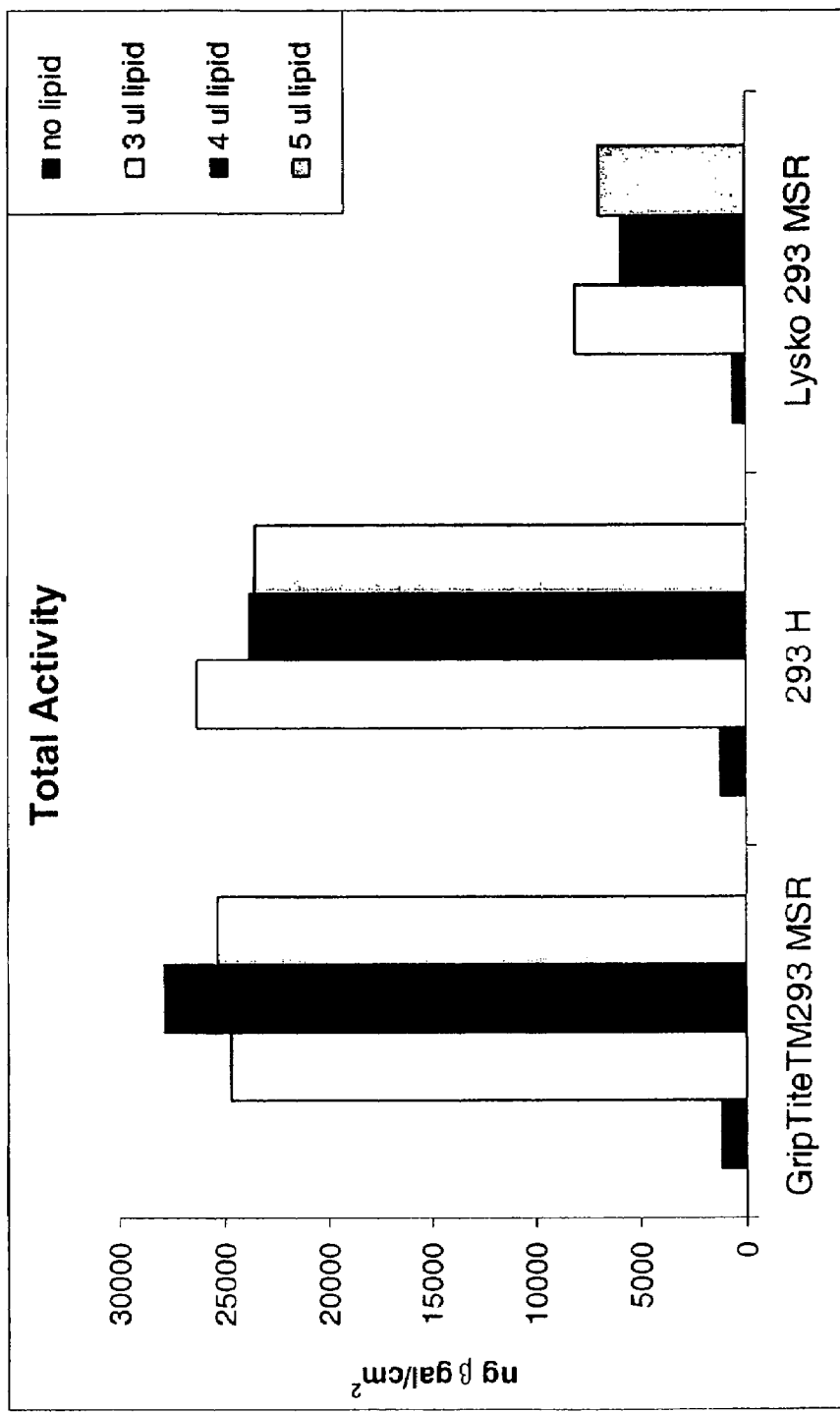
Figure 2. Expression of β-galactosidase in GripTite™ 293 MSR as compared to parental GIBCO 293H and Lysko 293 MSR Figure 3. Crystal Violet and β-gal staining of 293 MSR clones
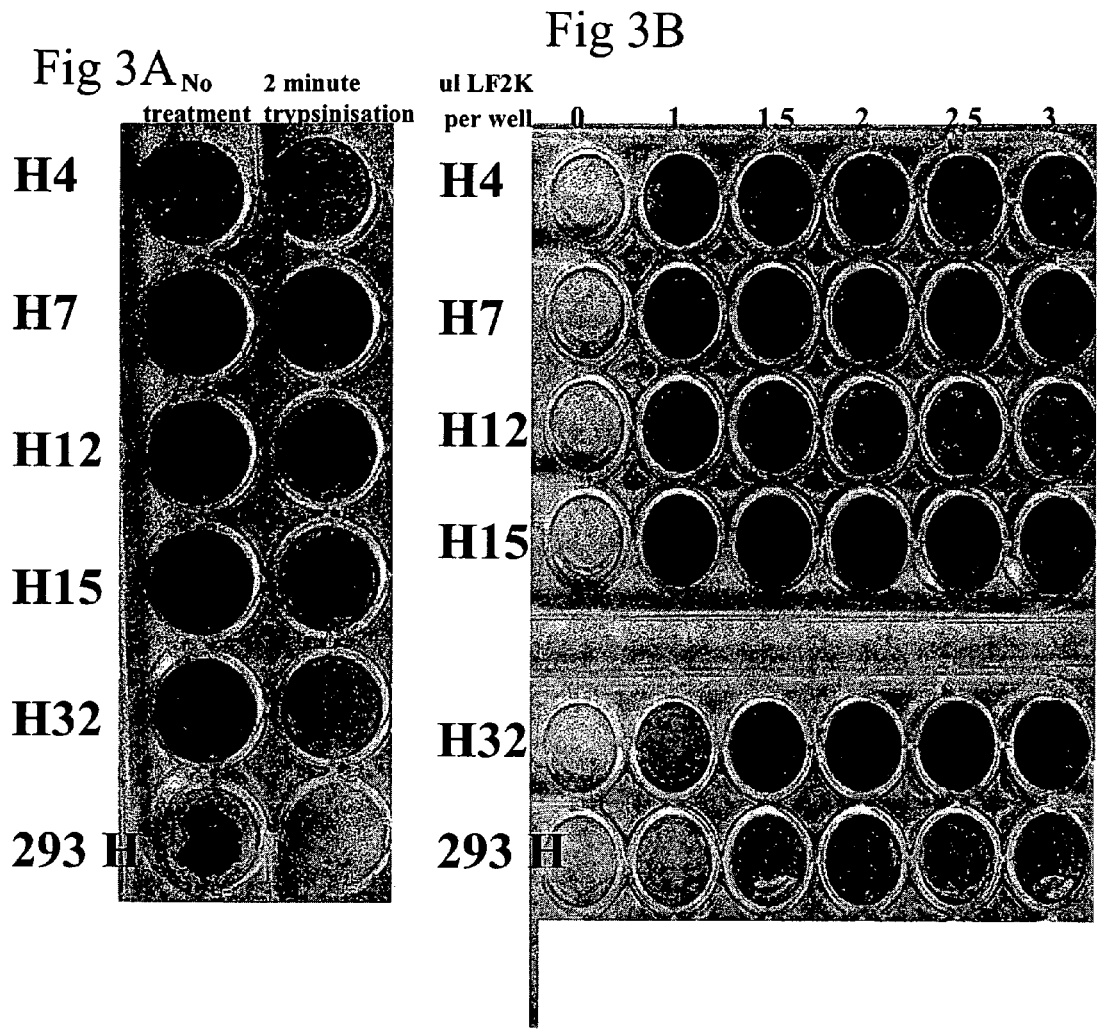

Figure 4. 293 MSR adheres to tissue culture plastic more effectively than GIBCO 293-H
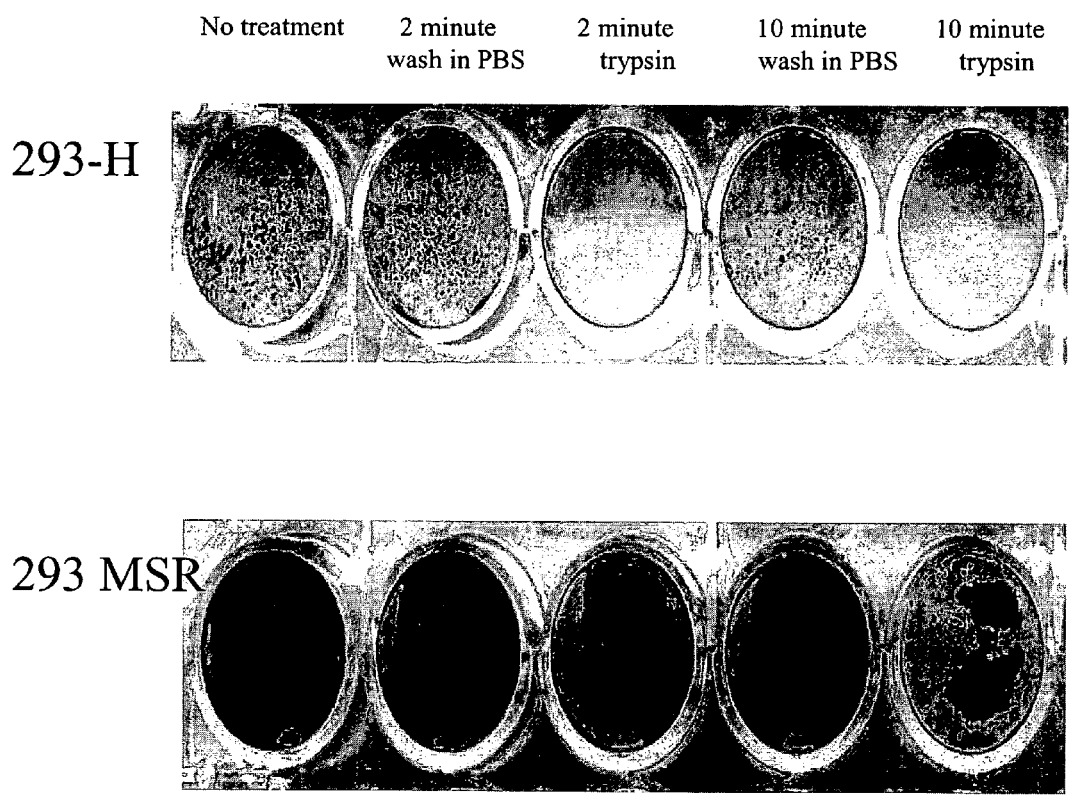

Figure 5. 293 MSR cells remain attached to tissue culture plastic during common protocols
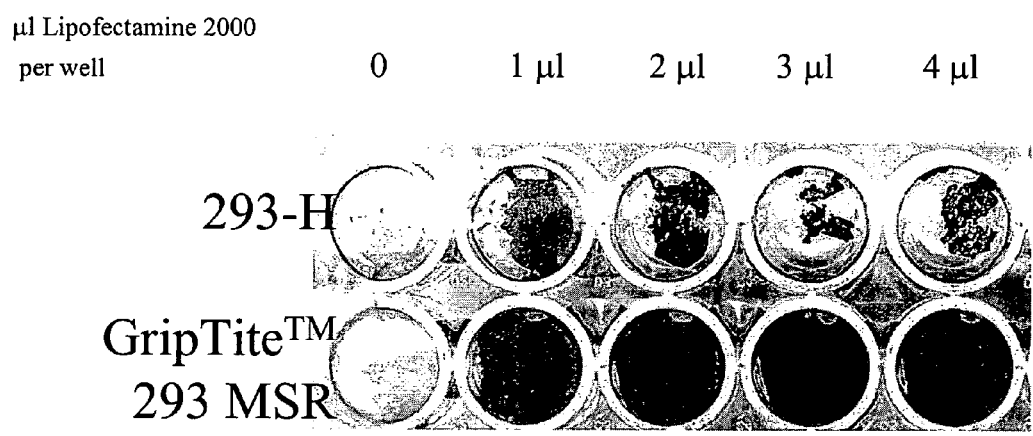
Cells were washed a total of 7 times in the course of X-gal staining.

Figure 6A. Sample key

A. Untransfected 293-H cells no wash control.
B. Untransfected 293 MSR cells no wash control.
C. pCMV♦SPORT-βgal transfected 293-H no wash control.
D. pCMV♦SPORT-βgal transfected 293 MSR no wash control.
E. Untransfected 293-H cells slant-pin wash.
F. Untransfected 293 MSR cells slant-pin wash.
G. pCMV♦SPORT-βgal transfected 293-H slant-pin wash.
H. pCMV♦SPORT-βgal transfected 293 MSR slant-pin wash.
I. Untransfected 293-H cells straight-pin wash.
J. Untransfected 293 MSR cells straight-pin wash.
K. pCMV♦SPORT-βgal transfected 293-H straight-pin wash.
L. pCMV♦SPORT-βgal transfected 293 MSR straight-pin wash.

Figure 6B. Plate washing
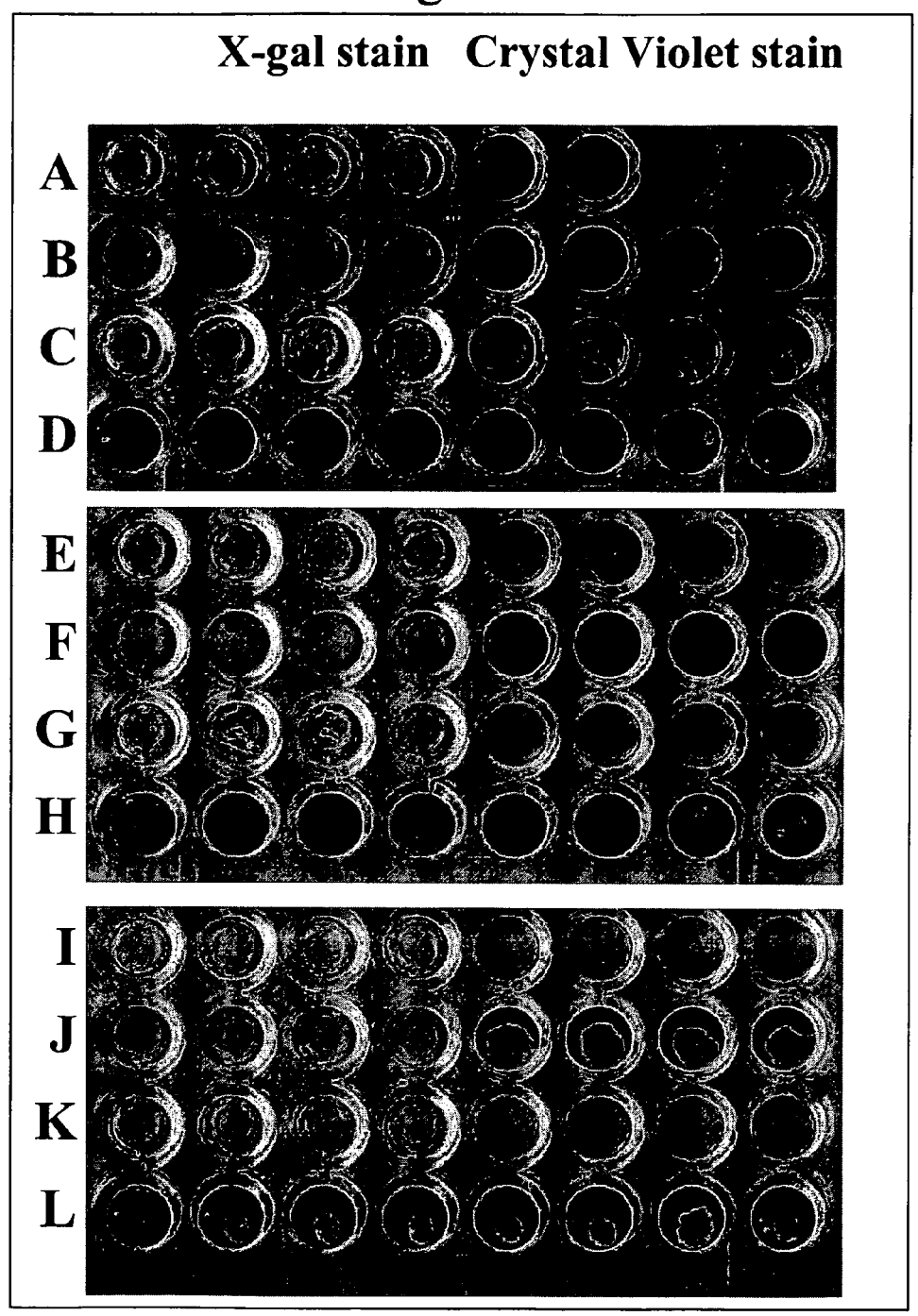

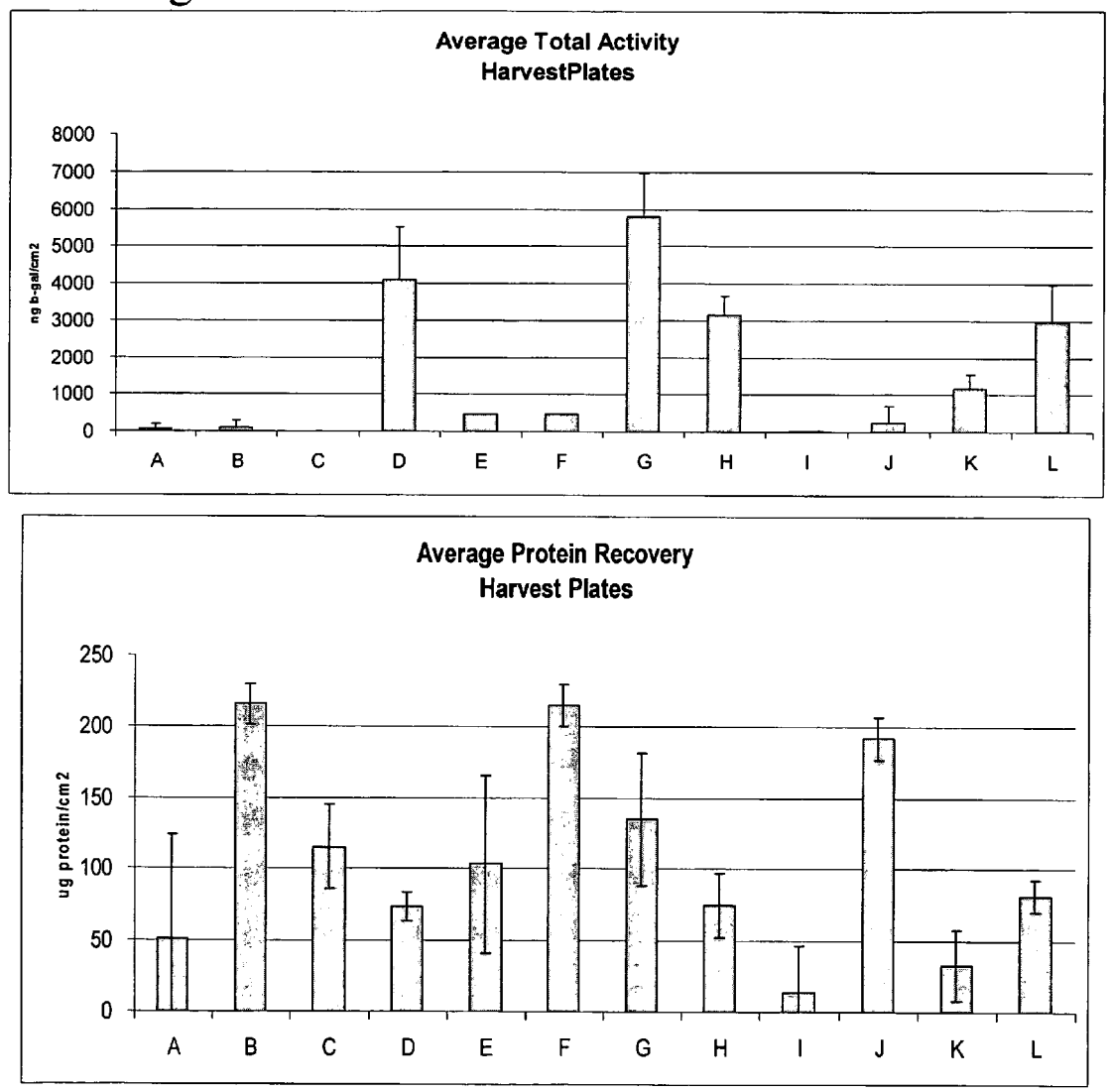
Figure 6C. ONPG and Bradford assays after plate washing

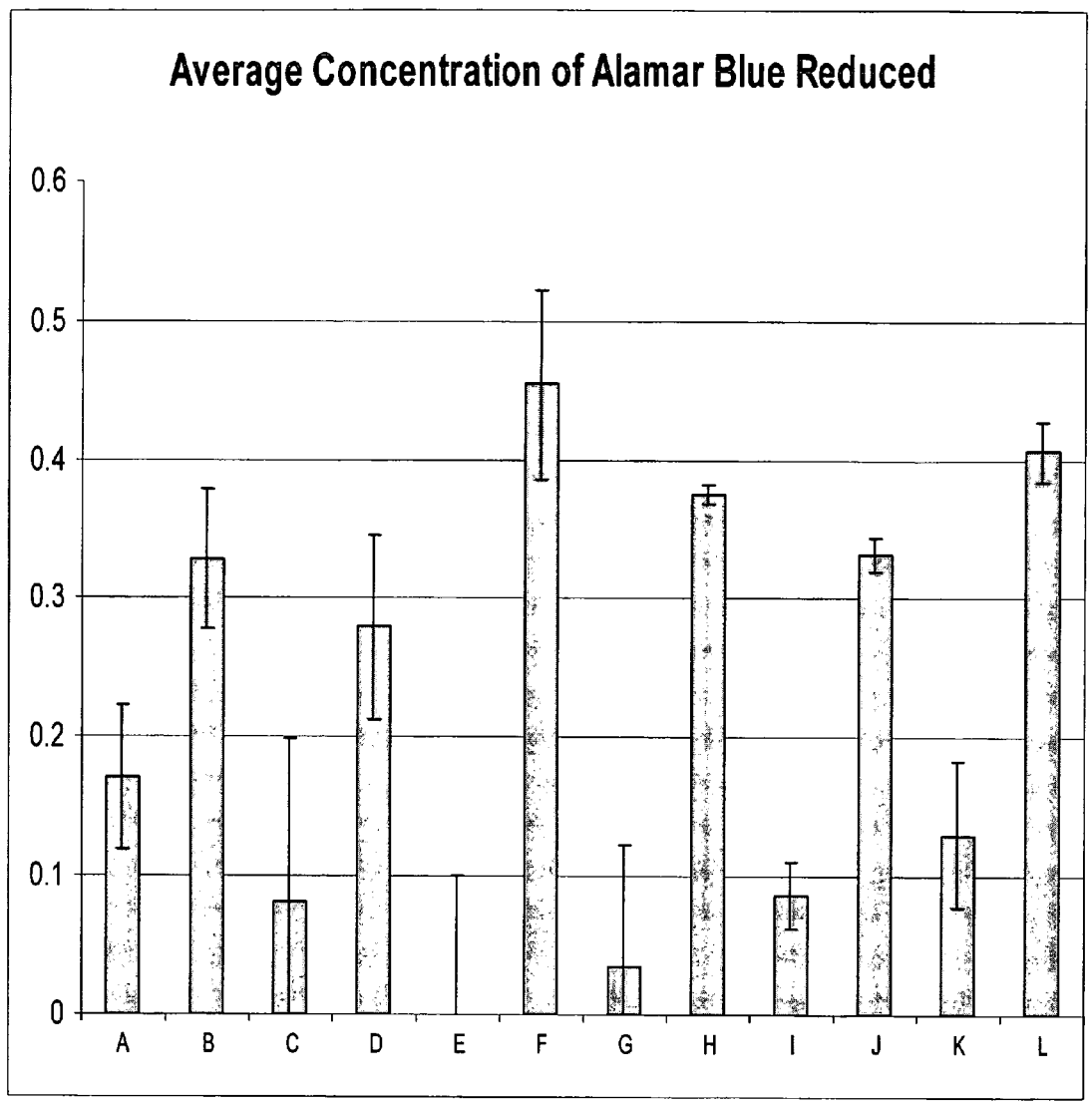
Figure 6D. Alamar Blue™ assay after plate washing

Figure 7.
GIBCO 293-H        GripTite™ 293
12-channel pipettor
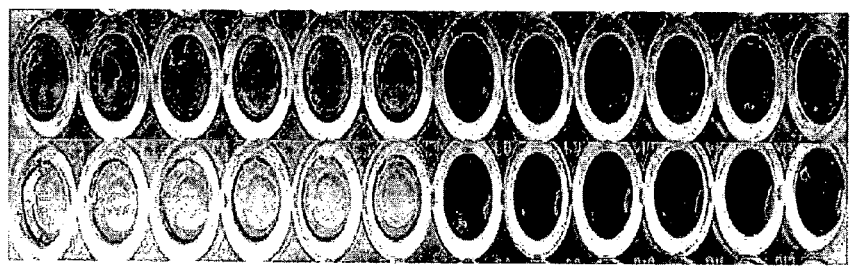
Crystal Violet Stain
β-gal stain
Packard MultiPROBE® II HTEX
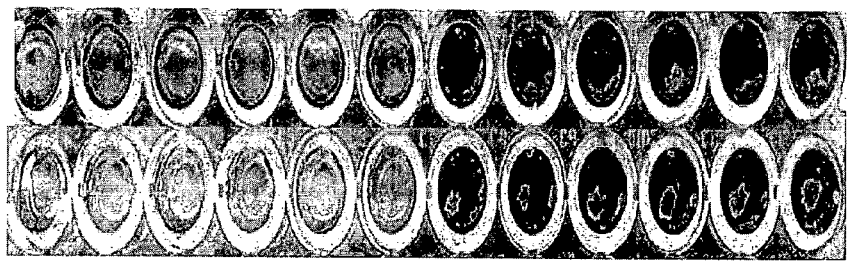
Crystal Violet Stain
β-gal stain Figure 8. Southern blot analysis of Flp-In™ 293 MSR clones digested with *NcoI*.
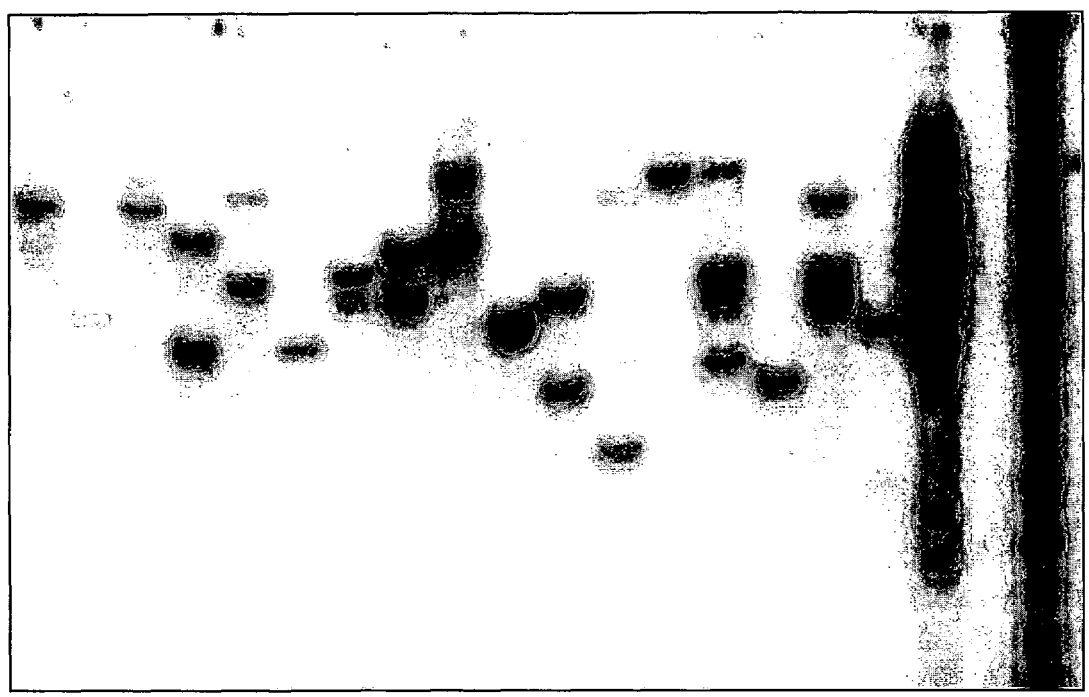

Figure 9. β-galactosidase expression levels pre-*flp* recombinase dependent integration.
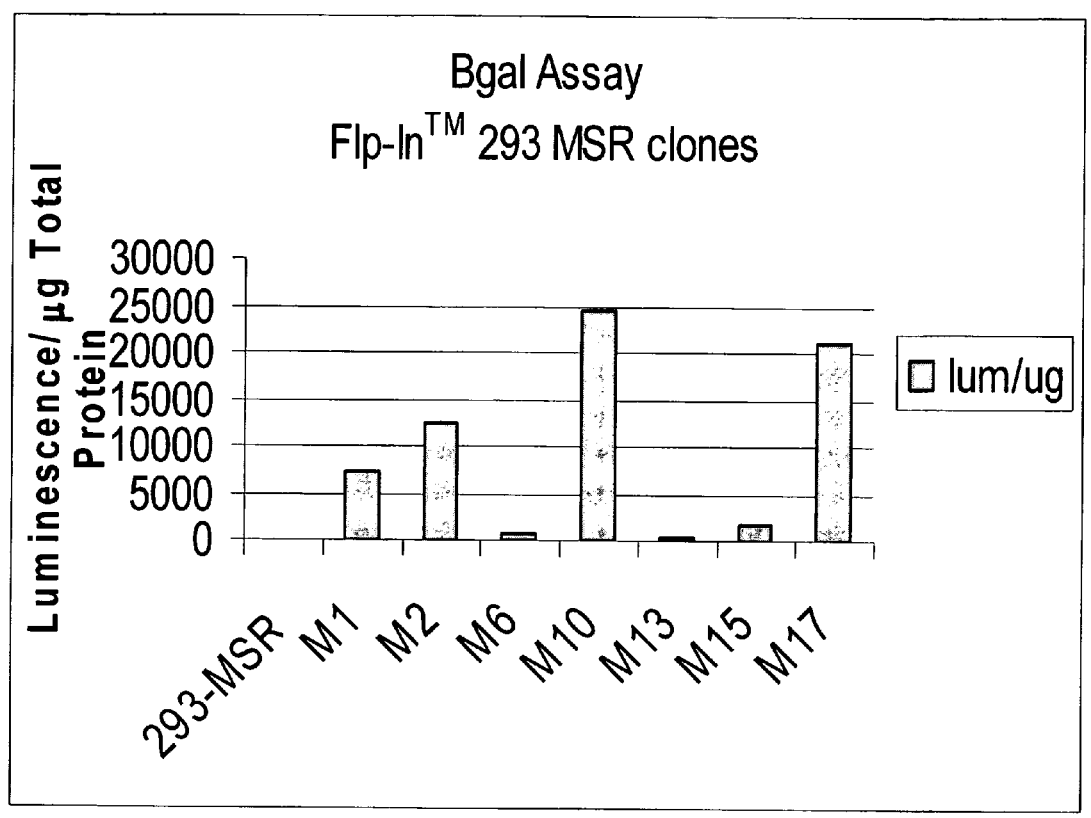

Figure 10. Southern blot analysis of Flp-In™ 293-MSR clones digested with *BglII*
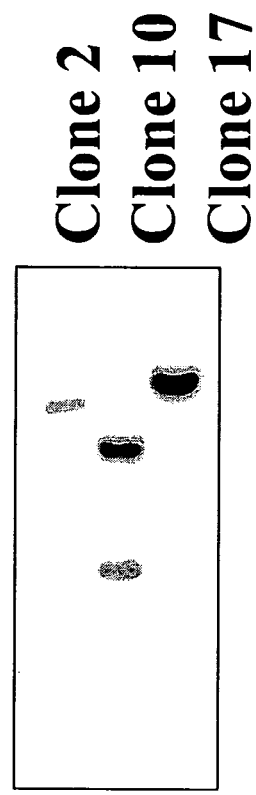

Figure 11. Anti-CAT Western blot on subclones generated by *flp* recombinase dependent transfection with pcDNA6/FRT/TO/CAT of Flp-In™ 293 MSR clone #17.
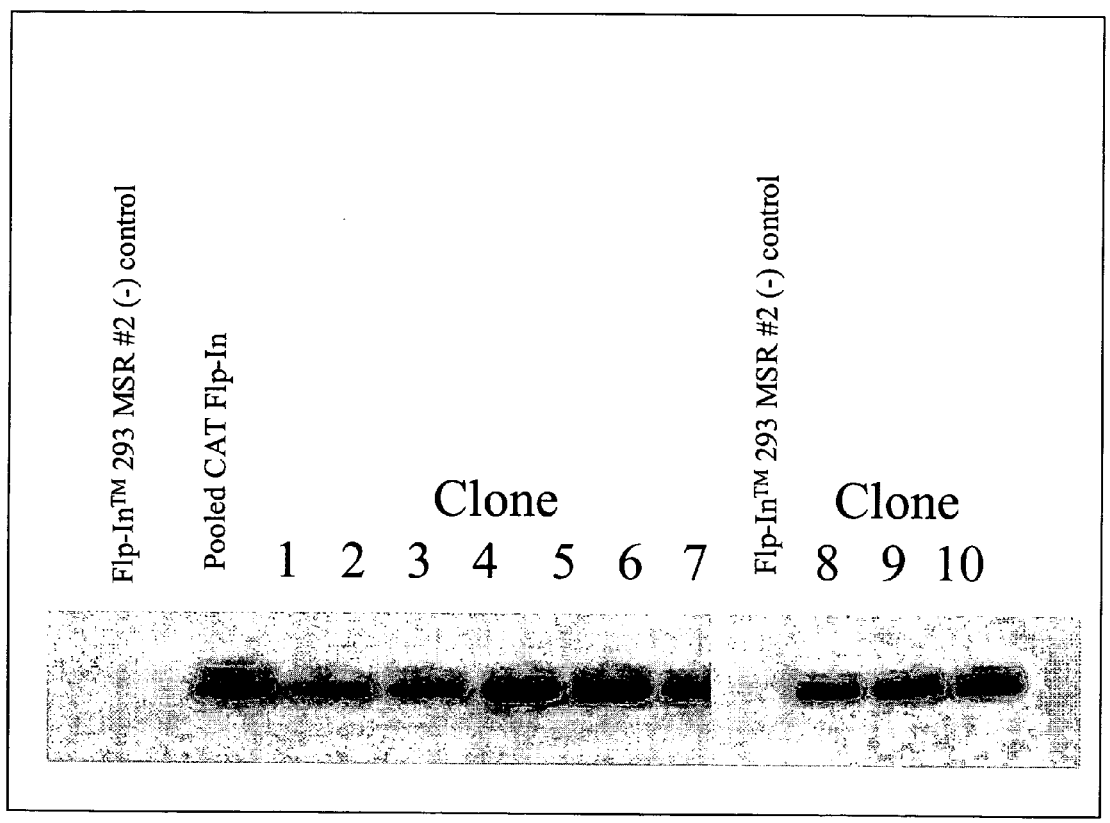

Figure 12. β-galactosidase expression levels post-*flp* recombinase dependent integration.
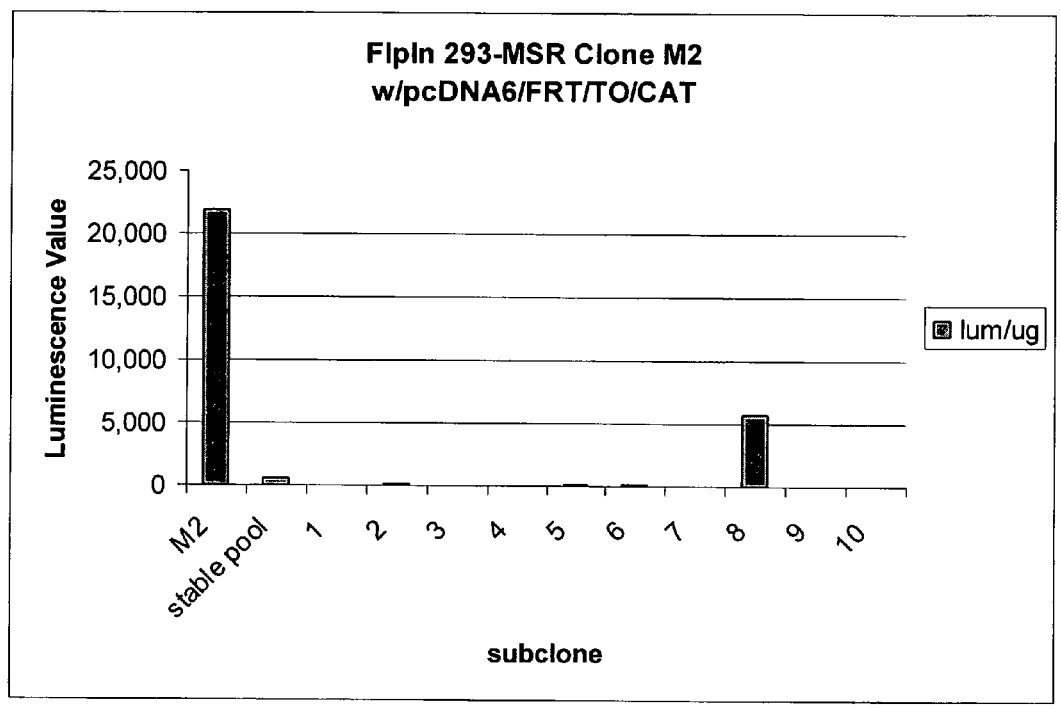

Figure 13. Prescreening of TREx 293 MSR clones.
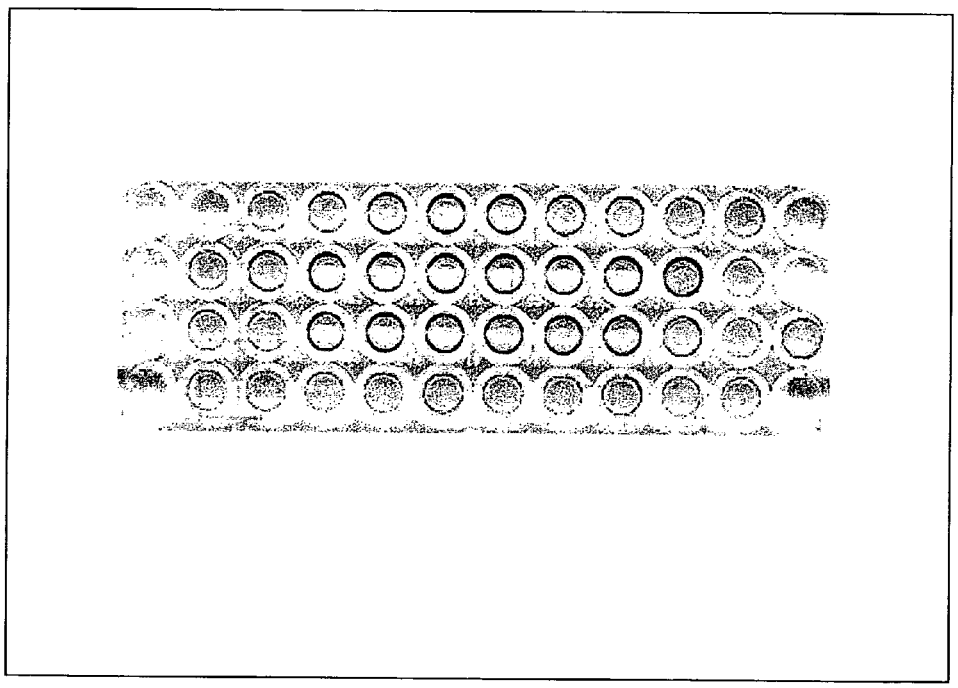

Figure 14. Screening of T-REx™ 293 MSR clones.
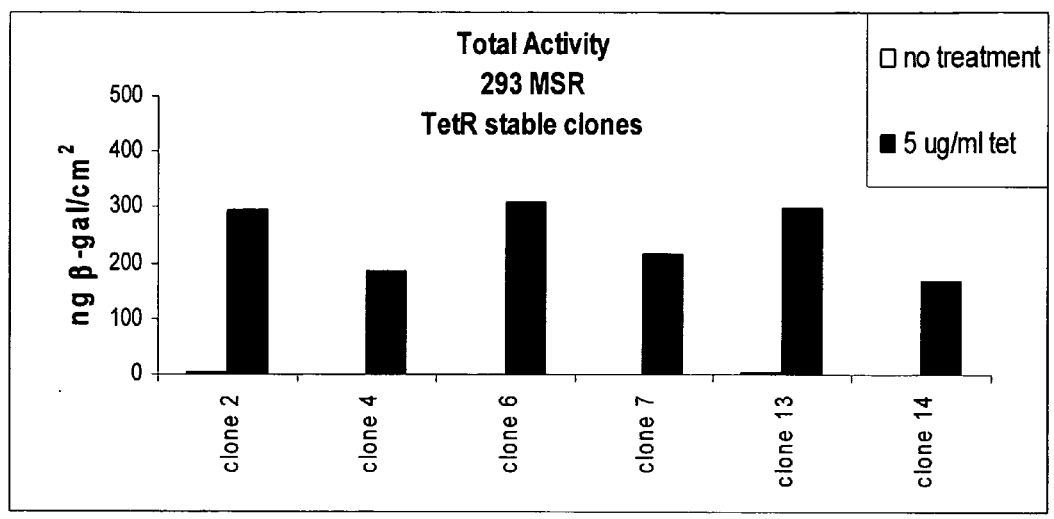
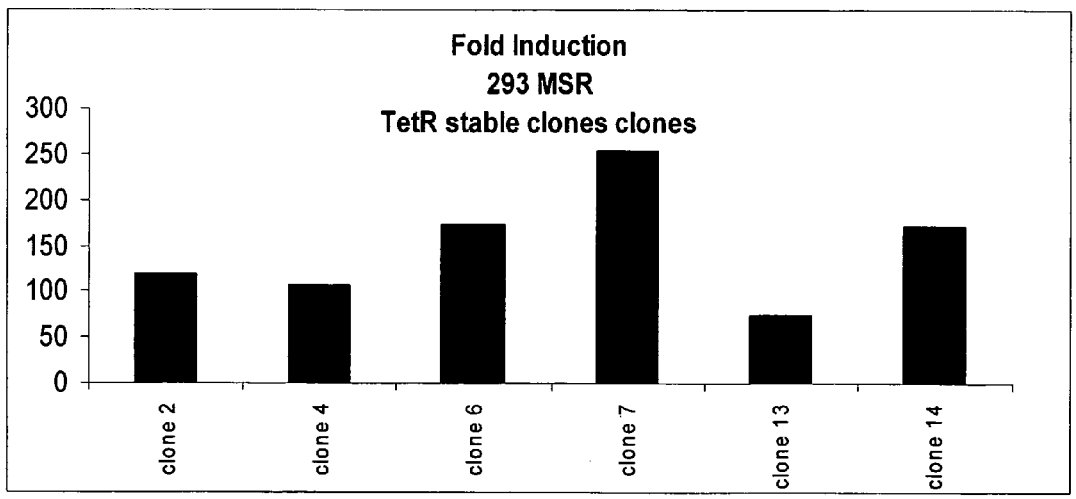

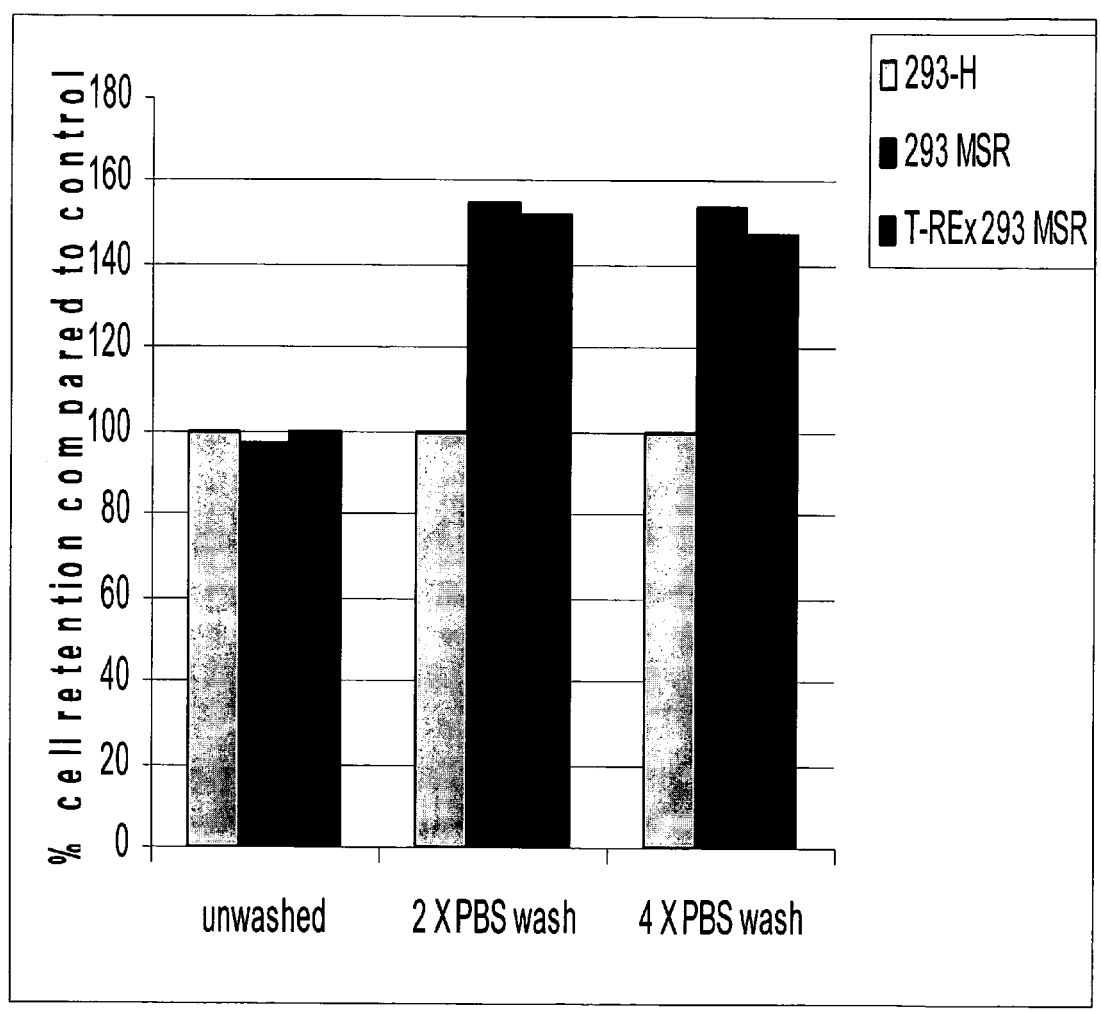
Figure 15. 293 MSR cell lines adhere better than GIBCO 293-H during plate washing Figure 16. T-REx 293 MSR adheres more tightly than T-REx 293
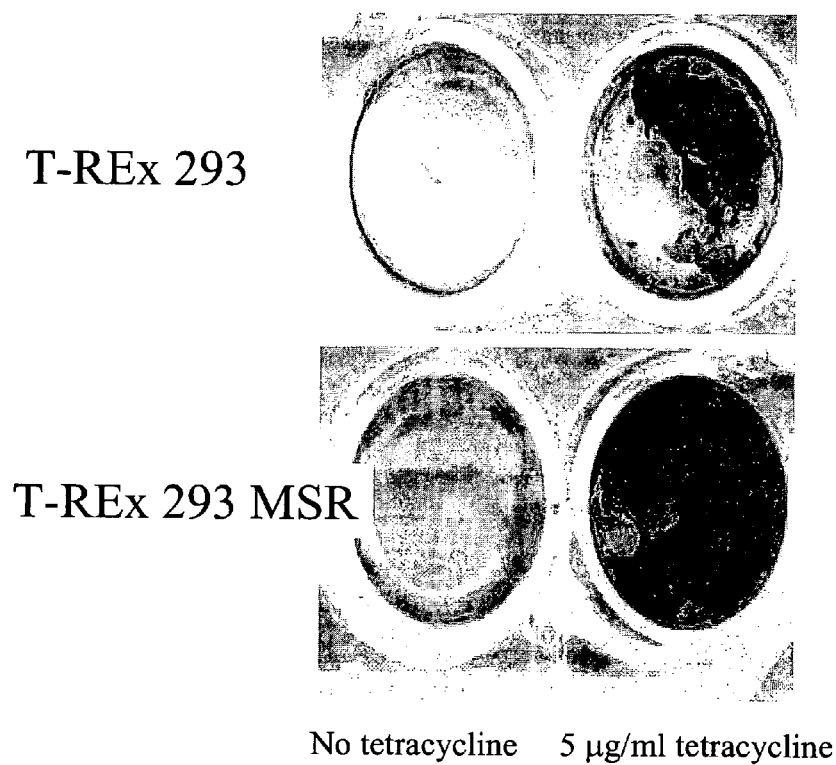
T-REx 293
T-REx 293 MSR
No tetracycline    5 µg/ml tetracycline Figure 17. 293 MSR cell lines adhere during PBS wash and trypsinization.
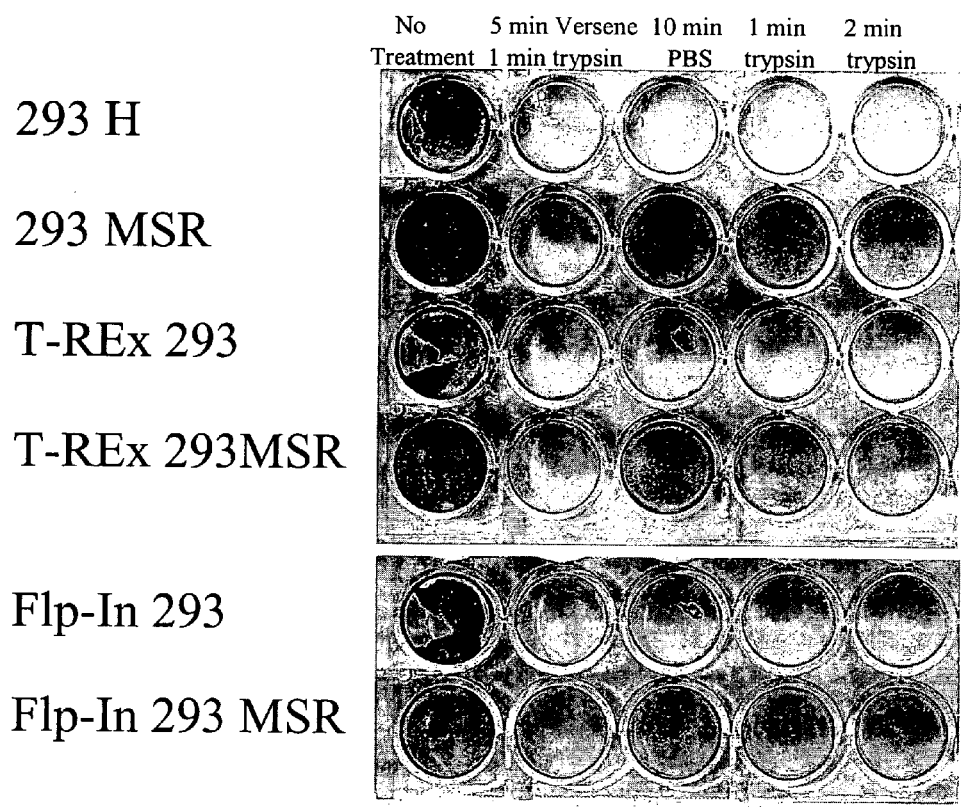

Figure 19. Labor/Time Savings

T-Flask Equivalency (Total Cells) to a 1L Bioreactor at $1 \times 10^6$ Cells/mL

| T-Flask Size | N | Estimated Confluency (Avg) | Media Volume per Flask | Flask(s) to Bioreactor Equivalency |
|---|---|---|---|---|
| 162 cm² | 6 | 75% | 25 | 18 |
| | | | | |
| 75 cm² | 6 | 90% | 15 | 28 |
| | | | | |
| 25 cm² | 6 | 80% | 5 | 110 |

Transient β-gal expression in suspension 293F cells

Transient β-gal expression: 293F cells 1L Bioreactor

Figure 24. Reporter proteins expressed using the FreeStyle™ 293 Expression System.

| Protein | Transfection | Product | Total |
|---|---|---|---|
| Human EGF | 3 ml | 4.3 mg/ml | 12.9 mg |
| Human EGF | 30 ml | 4.5 mg/ml | 135 mg |
| Chloramphenicol Acetyltransferase (CAT) | 3 ml | 0.5 ng/ml | 1.5 ng |
| Chloramphenicol Acetyltransferase (CAT) | 30 ml | 0.5 ng/ml | 15 ng |
| Luciferase | 30 ml | 2.3 ug/ml | 69 ug |
| β-galactosidase (β-gal) | 3 ml | 5.3 ug/ml | 15.9 ug |
| β-galactosidase (β-gal) | 30 ml | 7.7 ug/ml | 231 ug |

Figure 25. Western blot analysis of large T antigen in 293FT, 293A and T-Rex 293.
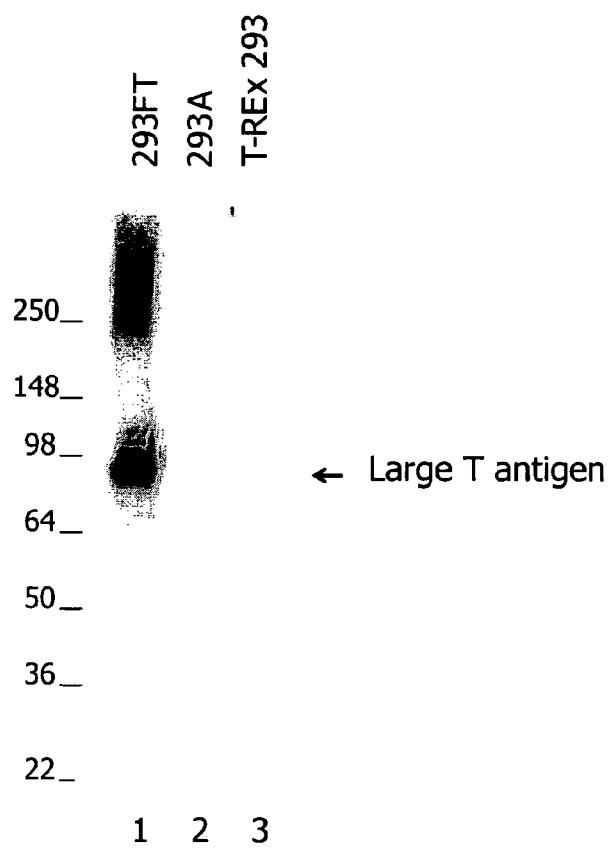

Figure 26. Packaging plasmids.
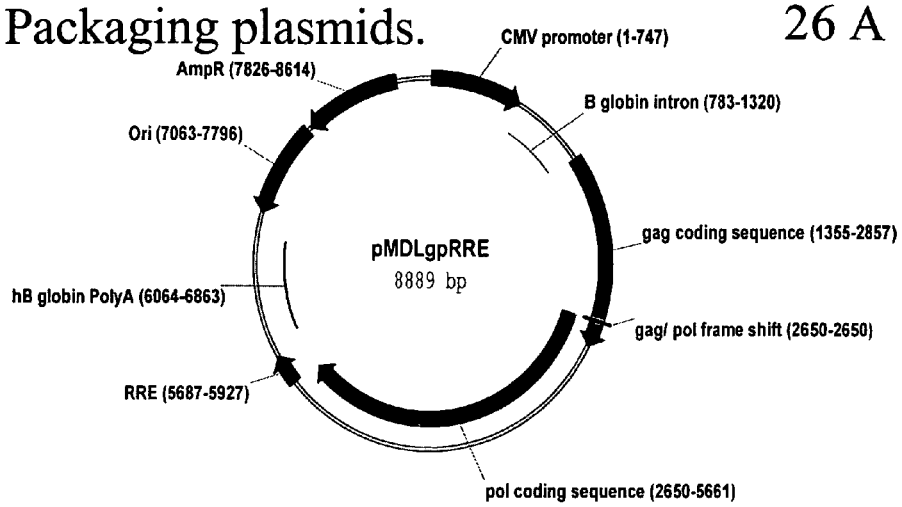
26 A
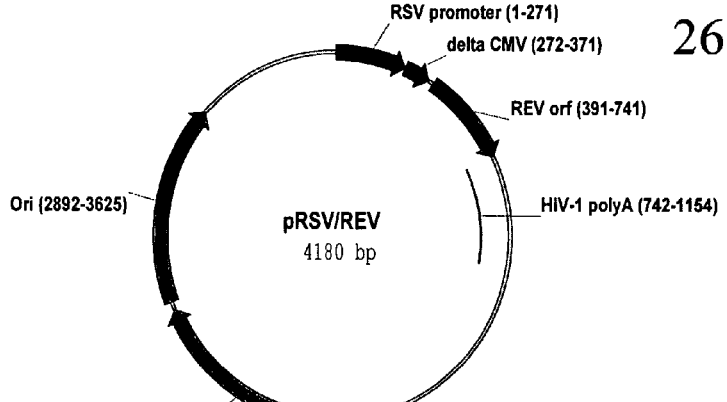
26 B
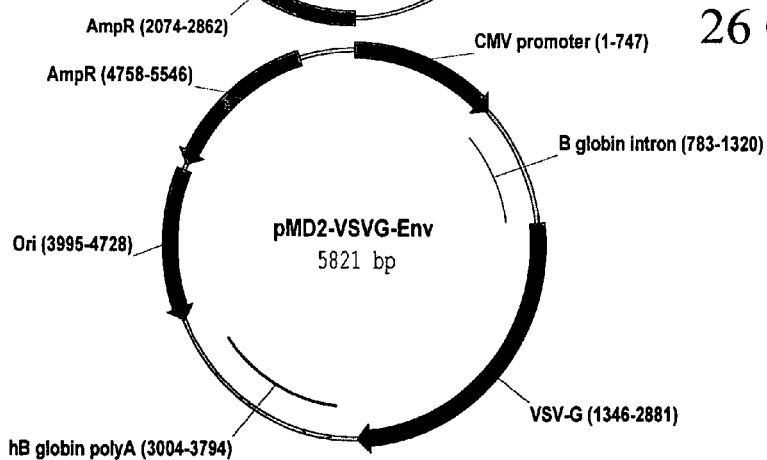
26 C

Figure 27. Expression vector maps.
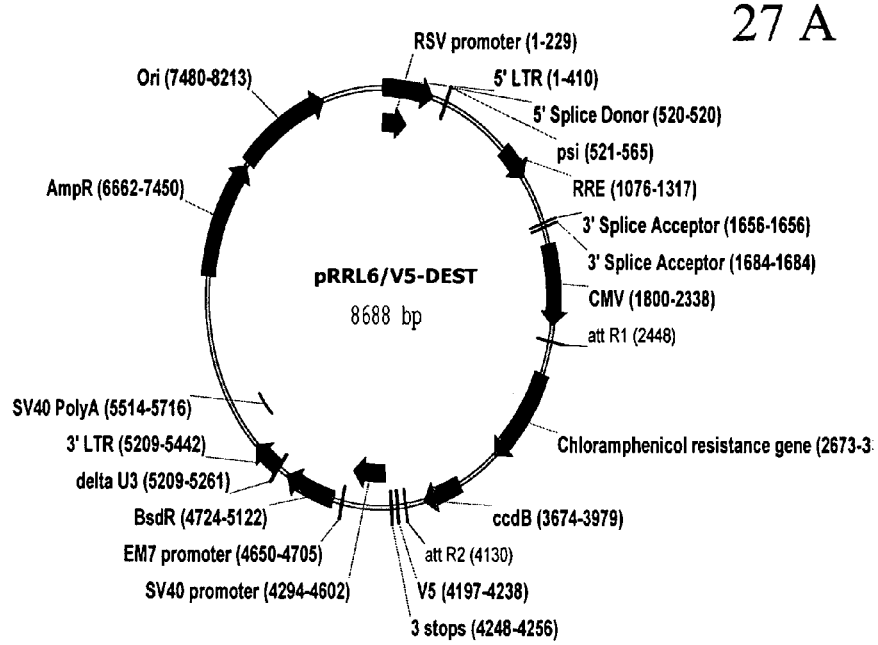
27 A
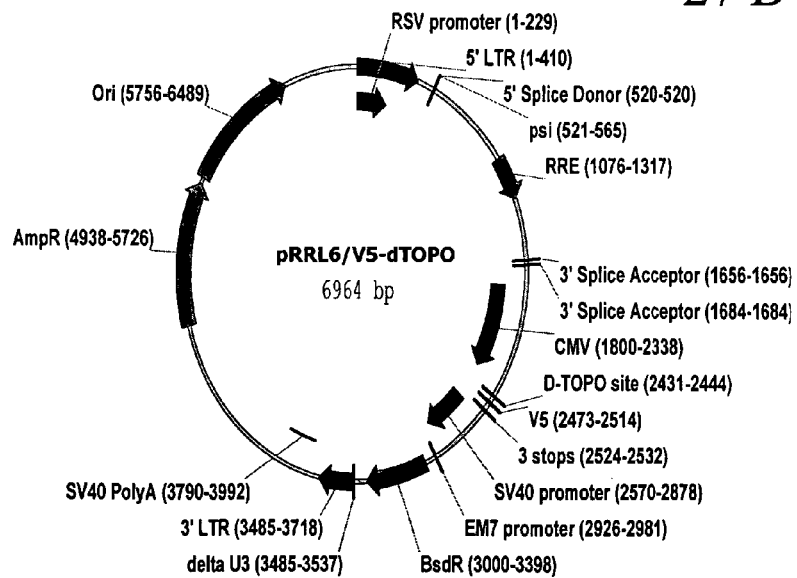
27 B

Figure 28. Transient expression of pRRL6/V5-GW/lacZ +/- V5 epitope addition.

Figure 29. Virus production protocols and titers.

FIG. 29 A. Timecourse of Production

Day 0   Plate 5 x $10^6$ 293FT per 100mm plate

Day 1   Four plasmid co-transfection (ratio = 1:1:1:1)
              12 µg DNA total (3 µg each)
              36 µl Lipofectamine 2000

Day 2   Replace media

Day 3-4   Harvest supernatant containing virus
              Spin 3000 rpm x 15' and/or filter 0.45 µm
              Aliquot supernatant, use for titering and store –80°C FIG. 29 B.   Examples of Production Titers ($Bsd^R$ cfu/ml)

|       | Empty | LacZ | GFP | CAT | PKC |
|-------|-------|------|-----|-----|-----|
| Exp 1 | $6 \times 10^6$ | $5 \times 10^5$ | $4 \times 10^6$ | n.d. | n.d. |
| Exp 2 | $3 \times 10^7$ | $3 \times 10^5$ | $6 \times 10^6$ | $8 \times 10^6$ | n.d. |
| Exp 3 | $7 \times 10^6$ | $6 \times 10^5$ | $2 \times 10^6$ | $1 \times 10^7$ | $3 \times 10^6$ |
| AVG   | $1.4 \times 10^7$ | $4.7 \times 10^5$ | $4 \times 10^6$ | $9 \times 10^6$ | $3 \times 10^6$ | n.d. = not determined

Figure 30. Gene delivery by lentivirus.
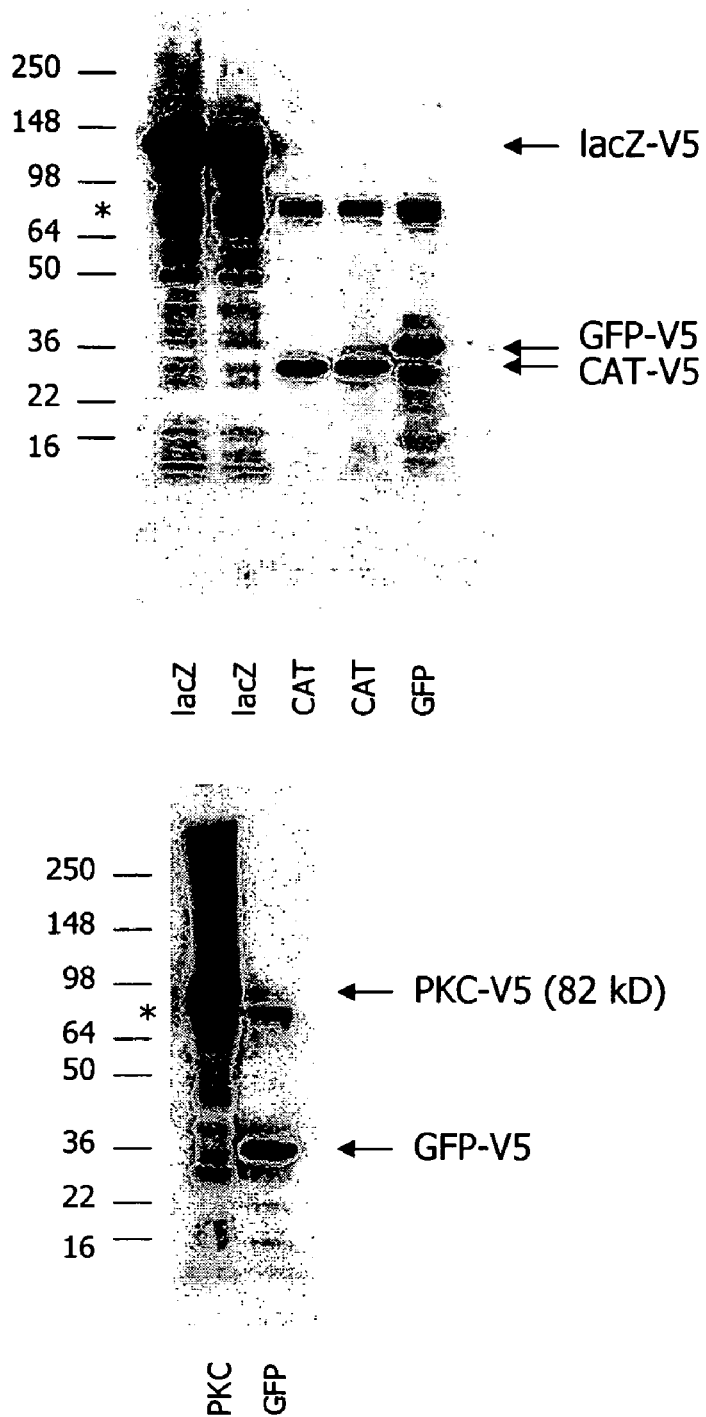

Figure 31. Gene delivery by lentivirus.
RRL6/V5-GW/lacZ
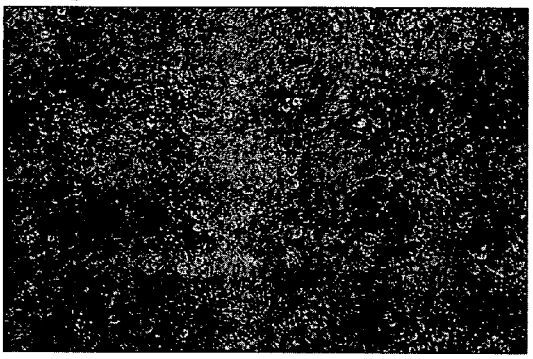
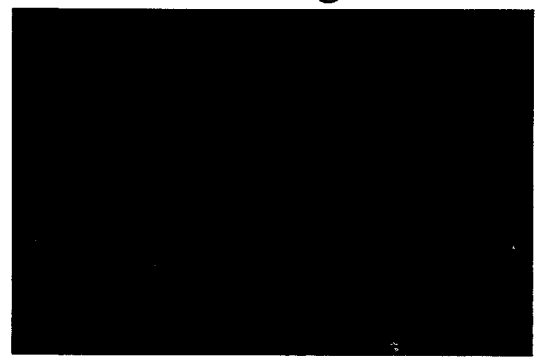
Brightfield                                Fluorescent
RRL6/V5-dT/GFP Figure 32. Gene expression is directly correlated with multiplicity of infection (MOI).
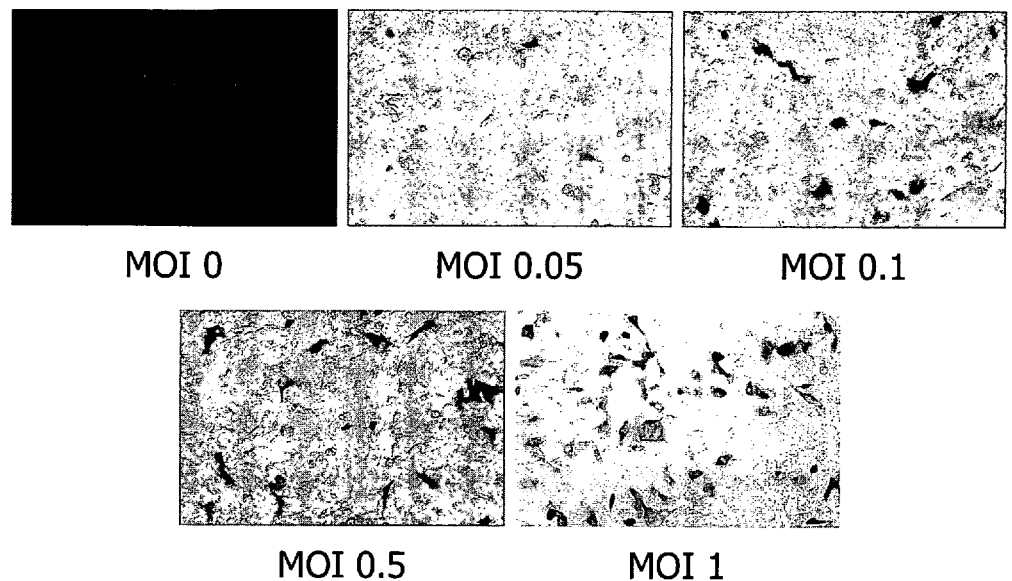
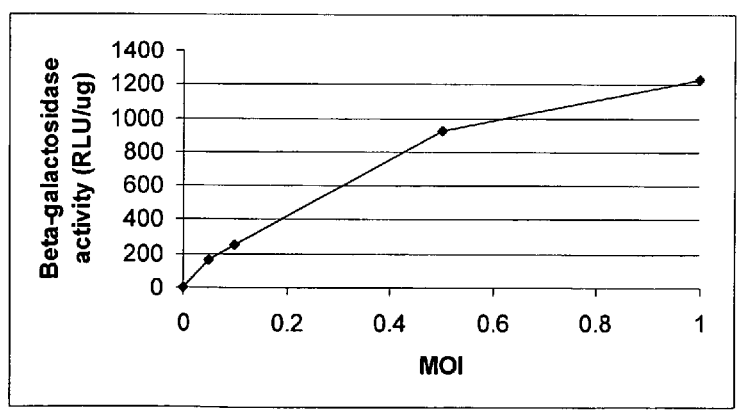

Figure 33. Lentivirus transduction of non-dividing cells.
Figure 33 A.
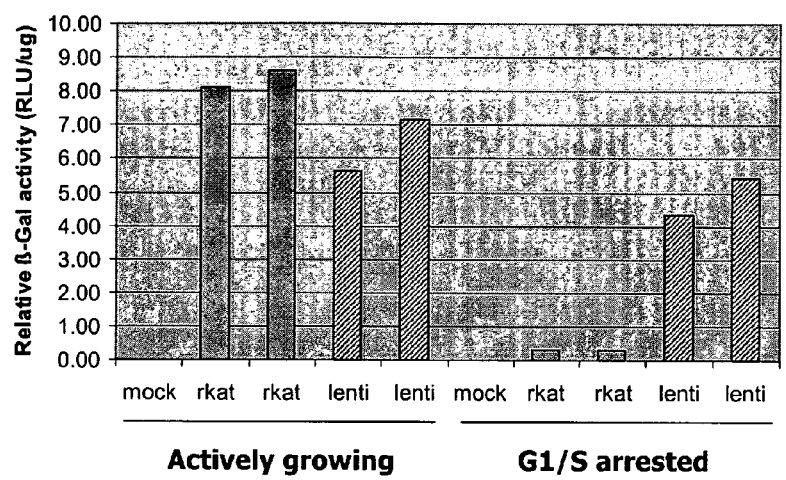
Figure 33 B.
rKAT6-lacZ retrovirus
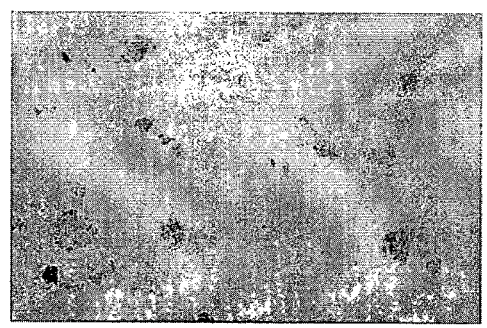
RRL6-lacZ lentivirus Figure 34. Lentivirus transduction of post-mitotic neurons.
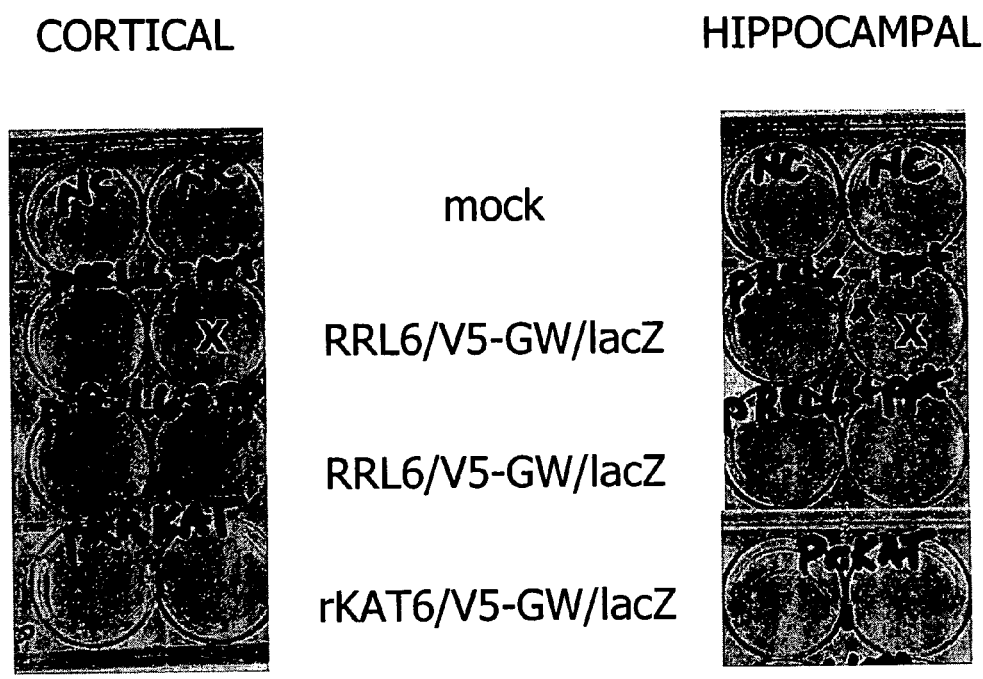

Figure 35. Long term gene expression from lentiviral vector delivery.
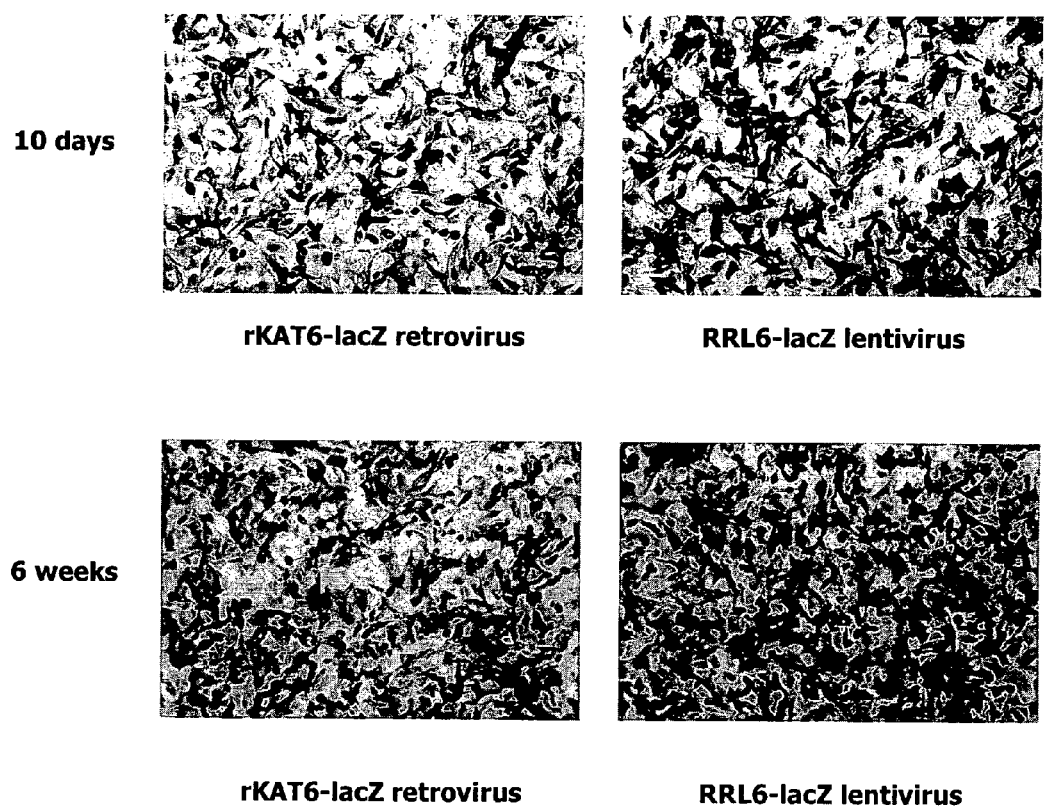

Figure 36. Titers of recombinant lentivirus from various cell lines

| Cell Line | pLentiGOI (A) | pLentiGOI (B) |
|---|---|---|
| 293 FT | $6.0 \times 10^6$ | $6.0 \times 10^6$ |
| 293 T #1 | $3.0 \times 10^5$ | $3.0 \times 10^5$ |
| 293 T #2 | $1.1 \times 10^6$ | $1.1 \times 10^6$ |
| 293 A | $1.0 \times 10^5$ | $1.0 \times 10^5$ |

Figure 37. Recombinant virus titer.
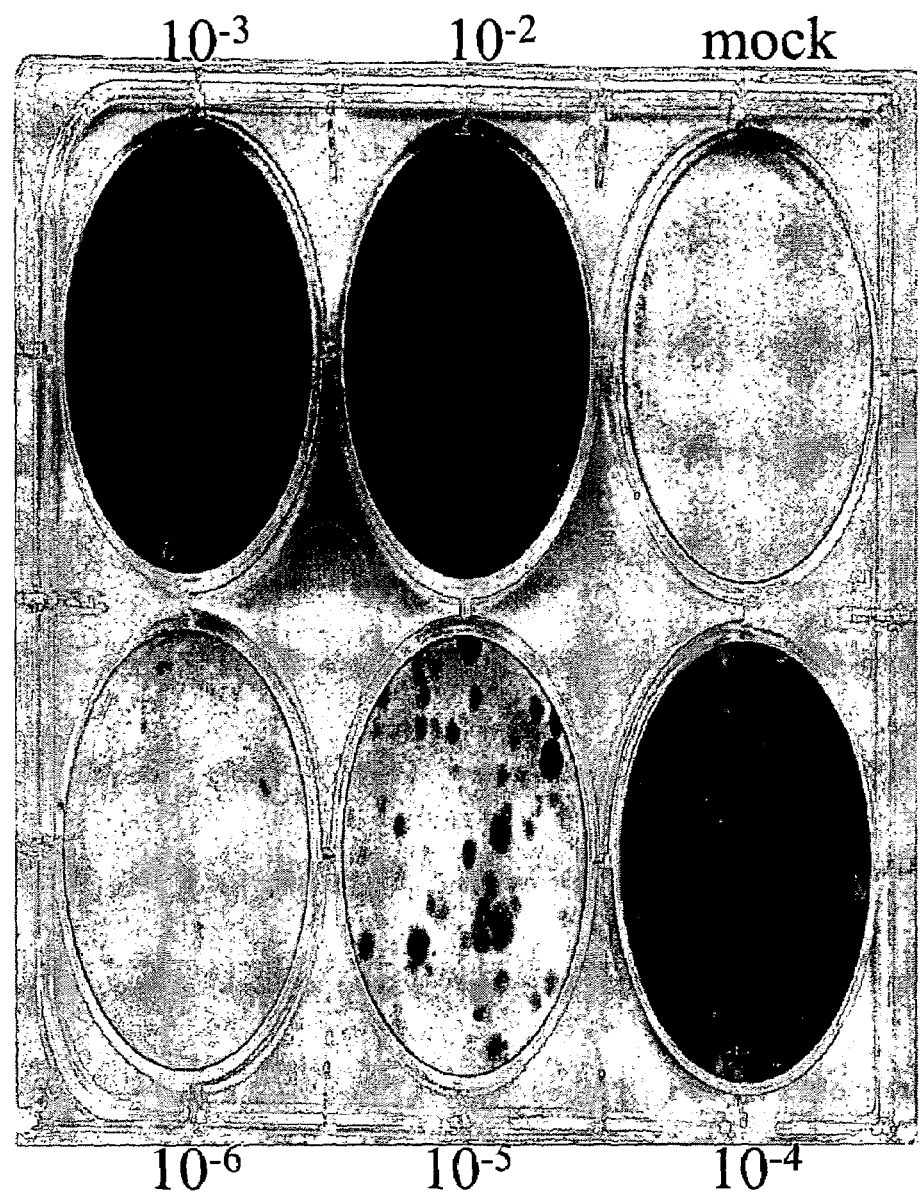

ATTACHED CELL LINES

CROSS-REFERENCE TO RELATED APPLICATIONS

This application claims the benefit of U.S. Provisional Patent Application No. 60/456,550, filed Mar. 24, 2003, and 60/529,405, filed Dec. 15, 2003, the contents of which are incorporated by reference in their entireties.

BACKGROUND OF THE INVENTION

1. Field of the Invention

This invention relates generally to cell lines suitable for use in viral growth, identification, titering or manipulation; vaccine growth or manipulation; viral transduction of cells; or recombinant production, screening, or measurement of protein or protein interactions in vitro.

2. Related Art

Mammalian cell lines are used as a model system for study of mammalian metabolism, physiology and disease. Mammalian cell lines are also used for the production or growth of virus and vaccines, antibodies and other therapeutic proteins, and other products used as therapeutics or reagents. In addition mammalian cell lines are used to identify or characterize virus, vaccines, proteins and other normal or modified cellular products. Common mammalian cell lines include those from human, ovine, porcine, bovine, rat, mouse, rabbit, raccoon, monkey, ape, etc. See for example the ATCC catalogue that specifically lists mammalian, amphibian, fish, reptile, arthropod, etc. cell lines. Each specific entry is hereby incorporated herein by reference. Other eukaryotic cells such as fish, e.g., SaBE-1c, EPC, RTG-2, IZSBS BS CL41, ECACC 93120820, WC 1 (IZSBS BS TCL65), etc. or insect cells, e.g., D2, KC. Dh 14, Dh 33, 79f7Dv3g, Ea.4, IPLB-Ld-65z, mosquito (such as: *Aedes albopictus* (larvae)—ECACC *Aedes albopictus* (larvae)—IZSBS Clone C6/36 *Aedes aegypti* ECACC 87091801, and TRA-171), *Antheraea* cells ECACC 90111908, other arthopods such as tick are important models, especially for genetics, viral studies, baculovirus infection, recombinant glycoprotein production, endocrinology, comparison studies, ecological monitoring and toxicology.

Other eukaryotic cell lines are also useful in accordance with the present invention. For example insect cells, such as mosquito, moth, armyworm, fruit fly, silkworm, etc. are also applied in culture. Plant cells, in part because they are totally animal free and are relatively easy to culture are also used extensively.

HEK 293 cells are and have been readily and freely available, for example, from commercial sources, such as the American Type Culture Collection, have been used extensively in in vitro assays, and for the production of recombinant proteins, vaccines and viruses. Because of the popularity of HEK 293 cells and their availability to the research community these cells are exemplified as one specific example of cells types to which the present invention is generally applicable. The present invention applies to all cell types, lines, or strains whose attachment properties might be beneficially altered either by increasing or decreasing attachment adherence, either permanently or transiently primarily for in vitro uses such as production or assays.

Properties including more rapid growth, more facile transfection, more efficient production, harvesting and/or purification of biochemicals (for example, proteins (including enzymes), hormones, peptide factors, lymphokines, growth factors, differentiation factors, lipids, including sterols, glycolipids, amine lipids, modified nucleic or amino acids etc.), engineered characteristics (including indicators, synthesis pathways for example for toxicity testing or bioproduction, etc.), might be advantageously inserted or selected for to achieve more useful cell lines as compared to the "wild-type" or standard type cell. This sentence has no verb for "Many cells" the assumed subject. Many cells are useful in the context of the present invention, for example, 293 cell lines and derivative cell lines publicly available either commercially or from depositories such as those listed by the USPTO of which the ATCC is one. Other well known depositories include DSMZi, ECACC, IZSBS and GEIMM. Various cell types are also available from many commercial or non-commercial distribution channels.

"Wild-type" HEK293 cells adhere only weakly to standard tissue culture supports making them difficult to use in automated formats and requiring special care in normal cell culture procedures and assay systems. In washing steps conventionally and repeatedly employed in such in vitro assays and other manipulations of cells, the cells readily detach from or are washed away from solid supports such as the plates or dishes in which the studies are performed. This problem typically results in inaccurate, unreliably low measurement or collection, or possibly selective or non-random sampling of the cells, product, protein, peptide or interaction to which the assay is directed. Because of this difficulty, HEK293 cells were engineered by Lysko at SmithKline Beecham Pharmaceuticals to constitutively express the Macrophage Scavenger Receptor (MSR), conferring a phenotype of increased adherence and allowing the use of these cells, 293 MSR, in previously technologically challenging applications.

Examples of desirability and utility of cells with improved attachment can be found in U.S. Pat. Nos. 5,683,903, 5,919,636 and 5,863,798 to Lysko teach an HEK293 cell engineered for enhanced attachment. The Lysko cells require serum for adherence. Furthermore the only improvement to the cell for adherence was the addition of the MSR gene. It is possible that further advantages might be achieved by inserting the MSR gene into cells already demonstrating improved adherence or other desirable characteristics. In addition to improved adherence, other capabilities or qualities are frequently desired in a cell.

The 293-H strain (Invitrogen, Carlsbad, Calif.) is a variant of the HEK293 cell line that was developed for better adherence than "wild-type" 293 cells in monolayer culture and is preferred for its ease of use for plaque assays and other anchorage dependent applications. This variant was selected based on increased adherence, transgene expression and permissiveness to transfection. A similar line 293 DSMZ ACC 305 is described as an adherent fibroblastoid cell line growing as monolayer. These cell lines, as examples of cells already demonstrating better adherence, could be engineered to further improve adherence to solid support matrices and other desired characteristics. CHO cells, a fibroblast-like and epithelial-like Chinese hamster ovary cell line, constitute another common cell line used in studies of genetics, toxicity screening, nutrition, and gene expression. These cells are typically grown in either monolayer or suspension. Improved adherence as described herein can especially be advantageously engineered into one or more CHO lines to improve utility. P1, a *drosophila melanogaster* embryo cell line that is semi-adherent, is known for use in virus studies especially with picomaviruses and rhabdoviruses. Similarly, COS-7 a green monkey fibroblast-like cell line grown in monolayer culture has been used for biological screening and viral replication. Cells such as these can also be engineered as described herein to extend or expand their utility.

The cell lines listed above as well as other known cells could more advantageously be used for many of their applications if adherence could be improved. Such improved adherence would retain more cells on the solid surface while permitting more rigorous processing steps such as automated washing in high throughput screening, efficient processing and assaying of cells would be enhanced.

In other applications, those using cells way wish to change a cells adherence for different phases of a project. For example, it may be desirable to grow or transfect cells attached or in suspension and subsequently render the cells more or less adherent, e.g., for analysis or harvesting of cells or cell product.

For some desired functions, such as bioproduction, there is a desire to expand and grow the cells in culture media free of animal derived components such as serum. Media can be formulated and cells can be adapted or modified so that existing cells can survive and indeed thrive in the absence of animal derived components. Alternatively, cells can be adapted to culture in a medium free of animal derived components.

Research and production activities in proteomics, vaccine production, protein folding, glycosylation, chaperoning and many other research areas requires or leads to significant quantities of biologically derived biochemicals. Some of these biochemicals are expected to be useful therapeutic agents.

In order to obtain the biologically active recombinant biochemicals in their most native and most likely active glycosylated form, mammalian cell-based expression systems should be, or are, utilized. Especially for therapeutic uses, serum free and more preferably animal component free culture conditions are desired.

The 293-F strain (Invitrogen, Carlsbad, Calif.) is a variant of the HEK293 cell line that was developed for growth in animal derived component free suspension media. Unlike "wild-type" 293 cells these cells can be grown either in monolayer culture in the presence of serum or in suspension culture in the absence of any animal derived component. This cell line is preferred for its ease of use for biochemical production and other suspension applications. This variant was selected based on increased transgene expression and permissiveness to transfection. A similar cell line, 293 ECACC 92052131 was adapted for growth in suspension by passaging HEK293 cells (ECACC No. 85120602) in nude mice.

CHO cells, a fibroblast-like and epithelial-like Chinese hamster ovary cell line, constitute another common cell line used in biochemical production and other suspension applications. These cells are grown in suspension for stable biochemical production. Improved growth in suspension, increased transgene expression, more human glycosylation patterns and permissiveness to transfection, as described herein, can especially be advantageously engineered into one or more CHO lines to improve utility.

Sf9, a *spodoptera frugiperda* cell line derived from IPLB-Sf-21-AE that can grow in both adherent serum supplemented or serum free suspension, is known for use biochemical production. Similarly, BHK-21 a hamster fibroblast-like cell line grown in monolayer culture has been used for biological screening and biochemical production. Cells such as these can also be engineered as described herein to extend or expand their utility.

The cell lines listed above as well as other known cells could more advantageously be used for many of their applications if their transfection, expression properties and/or effect from transfected biomolecules of the cells in suspension culture could be improved. Such improvements in cell systems would allow improvements in biochemical production systems reducing the time to product and increasing product yield and quality.

Another desired characteristic of cell lines for use in biochemical production is the ability to amplify the gene of interest within the target cell. The expression of the simian virus SV40 large T antigen is known to enable amplification of plasmid vectors containing the SV40 origin of replication. This is a common sequence found on many commercially available expression plasmid vectors. The amplification of an expression plasmid vector allows significantly greater expression of genes of interest. This increase in expression allows otherwise improbable or impossible products to be created such as a completely replication deficient recombinant *lentivirus*. Cells with characteristics of both vector amplification and improved adherence or suspension growth and improved expression would be especially useful. Adherence and suspnsion growth are not mutually exclusive since the time dimension allows cells to demonstrate improved adherence at one stage or under one set of conditions, and to demonstrate improved suspension growth at another time, earlier or later.

The 293-FT strain (Invitrogen, Carlsbad, Calif.) is a variant of the HEK293 cell line that was engineered to express the simian virus SV40 large T antigen. Unlike "wild-type" 293 cells, but like the 293-F strain, these cells can be grown either in monolayer culture in the presence of serum or in suspension culture in the absence of any animal derived component. This cell line is preferred for its ease of use for recombinant *lentivirus* production, biochemical production and suspension applications. This variant was selected based on amplification of SV40 origin of replication containing plasmid vectors, increased transgene expression, and permissiveness to transfection. A similar cell line, 293T/17 CRL-11268 was engineered to express a temperature sensitive mutant of the large T antigen for use in making recombinant retrovirus.

Chasin describes a CHO cell line DG44 that is deficient in the dihydrofolate reductase gene. See Chasin, L., et. al., *Proc. Natl. Acad. Sci. USA*. 77:4216–4220 (1980). Treatment of these cells with methotrexate after incorporation of both the dihydrofolate reductase gene and the gene of interest results in amplification of both genes leading to an increase in transgene expression.

There remains a need in the art for cell based tools useful in in vitro manipulations in genetic engineering and other applications that offer rapid growth capabilities; relative ease of transfection; are adherent and thus compatible with high throughput screening and automated testing; and permit obtaining of desired products and/or more clear and accurate results, either in the presence or absence of animal derived components. There is also a need for characterized cell lines that have rapid growth capabilities; relative ease of transfection; and grow in suspension in the absence of a solid support and in the absence of animal derived components for use in production of biochemicals. There is also a need for cell lines capable of amplification of plasmid vectors or genomic sequences that have rapid growth capabilities and relative ease of transfection.

BRIEF SUMMARY OF THE INVENTION

One aspect of the present invention provides improved adherence of cells to solid surfaces such as tissue culture plastic or beads. These cells may be engineered to include other incorporation sites for adding or screening additional genes. These cells may also be engineered to express target molecules on their membranes to increase targeting efficiency. Additionally, promoters that may or may not be inducible or repressible may be engineered into cells of the invention. The cells of the invention may be any cell line or derivative of a cell line that can be used in biological applications. Several suitable cell lines and promoters are mentioned above. Others are known in the art. Examples of various embodiments appear below. These embodiments are considered as demonstrative examples of the invention, which characteristics can be applied into the cell lines not specifically exemplified.

In one aspect, the invention provides improved cells, for example, HEK 293 cells or cells of another cell type, which cells have been transfected to alter adherence characteristics, for example, cells which have been transfected with a mammalian macrophage scavenger receptor gene. Preferably, this gene is the human Type I or II macrophage scavenger receptor gene. (See SEQ ID NOS: 1 or 3 of U.S. Pat. No. 5,683,903 to Lysko.) Preferably the cell is a cell such as the GIBCO® 293-H cell line demonstrating enhanced growth, transfection, expression and attachment characteristics before MSR gene transfection. The following cell lines of the invention have been deposited with the American Type Culture Collection, 10801 University Blvd., Manassas, Va. 20110-2209: FlpIn MSR (PTA-5076), 293FT (PTA5077), 293-H MSR (PTA5078), 293 MSR tet:R Hyg (PTA-5079), and FreeStyle™ (PTA5080).

In another aspect, the invention provides a method of enhancing the ability of cells, for example, HEK293 cells to attach in tissue culture. This method involves the steps of transfecting cells, for example, HEK293 cells or other cells whose adherence can be enhanced, with a selected mammalian macrophage scavenger receptor gene.

In yet another aspect, the invention provides a method of screening compounds for biological activity and or production. The method may involve screening improved 293 cells of the invention. In a preferred method, improved 293 cells have been further transfected with a selected gene and then screened for expression of the selected gene. In one more specific aspect, the cells expressing the selected genes are incubated in the presence of a compound of unknown biological activity, and then screened for the ability of the compound to affect the expressed gene product or its function or a measurable trait, characteristic or output of the cells.

In yet another aspect of the invention, cells engineered or selected to possess or express one or more desired trait or quality are engineered to modify adherence. Cells thus used may be selected from a desired cell line whose adherence is to be modified. The cells may, for example be cells adapted to selectable or desired culture conditions, such as growth in reduced serum or serum free culture. Similarly selected cells may be selected, for example, for their ability to grow in depleted media or in the presence of indicators.

In yet another aspect, the invention provides cells and a method for screening compounds for effects such as toxic effects. Cells of the invention can be washed with the compound or compounds to be screened. Cell metabolism, secretions, etc. can be monitored to determine effects of the compound.

In yet another aspect, the invention provides cells that expand or grow 1.5, 2, 3, 5, 7 or up to 10 times faster than "wild-type" 293 cells. In a preferred embodiment of this aspect, the cells grow or are adapted to grow in serum free or even more preferably animal derived component free medium or even chemically defined medium.

Yet another aspect of the present invention provides a high producing mammalian cell line capable of generating properly glycosylated biochemicals including proteins of interest. This cell line is particularly adapted to a serum-free medium which supports large-scale suspension transfection. The serum free medium which the cells are adapted to is free of animal-origin components. These cells can support both transient and stable transfection to maximize target biochemical yields.

Another aspect of the invention applies to amplification of plasmid vectors.

Another aspect of the invention relates to amplification of sequences incorporated into the genome.

Another aspect of the invention involves creation of replication-incompetent *lentiviruses* to deliver and express a gene of interest.

In yet another aspect, the invention provides cells that are more easily or efficiently transfected, for example, 3 fold, 5 fold 10 fold, 25 fold, 50 fold, even 100 fold or 1000 fold more efficiently than "wild-type" 293 cells. In a preferred embodiment of this aspect, the cells grow or are adapted to grow in serum free, or even more preferably, in animal derived component free medium. Chemically defined media may be preferred in some applications. In a preferred embodiment, transfection is rendered more efficient by engineering the cells to express a targeted marker. The marker then serves to partition the transfecting agent at the desired location.

One aspect of the present invention includes at least one recognition sequence. Preferably the at least one recognition sequence is present in conjunction with at least one additional aspect of the invention.

In one aspect of the present invention, a recognition sequence is inserted into the genome of a target cell line.

Flp-In™ employs a unique recombination mechanism. FLP recombinase catalyzes a site-specific recombination reaction that is involved in amplifying, for example, the 2 micron plasmid of *Saccharomyces cerevisiae*, during DNA replication. FLP recombinase of *S. cerevisiae* is used to recombine a gene of interest into a FRT site previously integrated into the host cell line. In the presence of FLP recombinase, a second DNA sequence containing a FRT site is integrated into the FRT site of the host cell genome. This specific integration results in the creation of an isogenic cell line where all transfected clones produce equivalent levels of the protein of interest. Flp-In™ cell lines have a single insertion of the FRT site in the genome. The expression level of the site is characterized by the expression of a reporter gene. When the FRT site is in a transcriptionally active area of the genome consistent high-level reporter gene expression is observed.

In a preferred aspect of the present invention, the FLP recombination site (FRT site) is integrated into an active section of the host cell genome.

In yet another aspect of the invention, aspects of faster expansion and ease of transfection are combined in the same cell. In a preferred embodiment of this aspect, the cells grow or are adapted to grow in serum free or even more preferably animal derived component free medium or in chemically defined medium.

In a preferred aspect of the invention, cells are engineered to express a surface receptor to bind extracellular compounds, for example for labeling cells, assaying compounds present in the medium, selectively partitioning compounds for reaction with the cell including uptake of bound compounds such as compounds having reactive activity with genetic material inside the cell. Especially preferred are reactive compounds that bind to DNA or RNA to activate or inactivate same and reactive compounds capable of excising or inserting genetic material from or into DNA or RNA within the cell nucleus or mitochondria. A receptor for a virus or retrovirus or a particle having viral or retroviral activity is also especially preferred.

In yet another aspect, cells can be engineered to express specific pathways or can be co-cultured with other cells. The expressed pathways or co-cultured cells might provide metabolites, for example, metabolites of a compound to be screened. The effects of metabolites on the reporter cell, for example an engineered 293 or other cell, could then be determined. One sub-aspect may include an adherent population and a suspension population. Either might provide the metabolite or reporter cell. In a preferred, aspect high throughput screening is employed. In an especially preferred aspect, the adherent cells are used multiple times, for example as a screen for sequential exposures of like or unlike compounds, including metabolite compounds.

Cells of the invention may be tagged with fluorophores or binders of fluorophores or other markers either internally or externally to aid in detection of properties of interest. In addition to or as an alternative to fluorophores other tags, such as nuclear tags, uncommon atoms, etc, can be used.

In a particular aspect of the invention, the cells producing the MSR are grown in a serum-free medium, preferably chemically defined medium. Preferably the host cell is a mammalian host cell and preferably Chinese hamster ovary (CHO) cells including, but not limited to CHO K1, CHO pro3⁻, CHO DG44, CHO DUXB11 and CHO DP12 cells. Other mammalian host cells useful in the method of the invention include, but are not limited to, mouse myeloma cells, NS0, and hybridoma cells, such as mouse hybridoma cells, baby hamster kidney (BHK) cells, COS cells, HeLa cells, C127 cells, mouse L cells, 293 cells and Ltk-cells.

Another aspect of the invention provides cells that have an inducible or repressible expression system. One such system is the T-REx™ system whereby repression of expression is inactivated in the presence of tetracycline.

T-REx™ employs a unique derepression mechanism that offers superior control over other inducible expression systems. The *E. coli* tetracycline operon is used to tightly regulate expression from a promoter. For T-REx™ the CMV promoter is used. Two tetracycline operator sites are positioned downstream from the CMV TATA element. The Tet repressor protein normally and stably expressed in T-REx™ cells inhibits CMV promoter activity. Expression of the gene or genes of interest under CMV control is thus effectively blocked. However, expression of the gene or genes of interest can be turned on to a high level by addition of tetracycline, fomenting expression by causing dissociation of the repressor complex. Other systems less tightly controlled or systems to be perfected offering tighter control may be used to control expression in cells of the present invention.

The inducible or repressible/derepressible expression system can be operably linked to one or more genes that modify attachment. The inducible or repressible expression system can be operably linked to one or more genes of interest that do not directly modify attachment. For example a cell line may be transfected in suspension (attachment genes off); and plated for assays or other characterization (attachment genes on). In a different aspect cells might be selected in suspension and attached to plastic for screening. In yet another aspect cells may be selected from attached cells (attachment genes on); and then grown in suspension (attachment genes off), for example, as biofactory cells. Alternatively, a characteristic not related directly or not related indirectly to attachment may be controlled by a gene of interest whose activity is inducible or repressible.

The cells of the invention having the enhanced attachment characteristics are particularly suitable for high throughput screening allowing for more rigorous or repetitive washing protocols. The cells can be used on any biologically compatible solid support, for example in flasks, multi-well plates or attached to beads.

Each of the forgoing aspects of the invention may be found individually or in combination with at least one other, up to as many as all of the above advantageous aspects. Additional aspects known in the art though not specifically discussed herein may be incorporated into and used with the present invention.

Other aspects and advantages of the present invention are described further in the following detailed description including several preferred embodiments of the present invention.

BRIEF DESCRIPTION OF THE DRAWINGS

FIG. 1 is a schematic of the MSR receptor.

FIG. 2 is a bar graph of β-galactosidase activity in GripTite™ 293 MSR, GIBCO® 293-H and Lysko 293 MSR after transient transfection with the shown amounts of Lipofectamine™ 2000.

FIG. 3. FIGS. 3A and 3B are photographs of tissue culture dishes stained with Toluidine Blue-O (FIG. 3A) to show the presence or absence of cells attached to the dish before and after enzymatic digestion of general attachment factors or X-gal stained for β-galactosidase activity (FIG. 3B) to show enzymatic activity of a transiently transfected lacZ gene.

FIG. 4 is a photograph of a tissue culture dish showing GIBCO® 293-H and GripTite™ 293 MSR cells stained with crystal violet to show the presence or absence of cells attached to the dish after the indicated treatment.

FIG. 5 is a photograph of a tissue culture dish X-gal stained for β-galactosidase activity. The indicated cell lines were transiently transfected with the lacZ gene as shown.

FIG. 6A is a sample key for FIGS. 6B, 6C, and 6D.

FIG. 6B is a photograph of tissue culture dishes X-gal stained for β-galactosidase activity to show enzymatic activity of a transiently transfected lacZ gene (left 4 columns) or stained with crystal violet (right 4 columns) to show the presence or absence of cells attached to the dish before and after washing with an automated plate washing device.

FIG. 6C is a bar graph of β-galactosidase activity (upper panel) and protein concentration (lower panel) for the indicated cell line and treatment protocol.

FIG. 6D is a bar graph the average concentration of Alamar Blue reduced by the indicated cell line and treatment protocol.

FIG. 7 is a photograph of tissue culture plates X-gal stained for β-galactosidase activity (left 6 columns) or for the presence of cells with Crystal Violet (right 6 columns) either using a 12-channel pipettor (top) or a Packard MultiPROBE II HTEX liquid handling robot (bottom).

FIG. 8 shows a Southern blot analysis of genomic DNA from potential Flp-In™ 293-MSR clones digested with NcoI.

FIG. 9 is a bar graph showing β-galactosidase activity from a lacZ gene that has been integrated into the genome of various potential Flp-In™ 293-MSR clones.

FIG. 10 is a Southern blot analysis of genomic DNA of potential Flp-In™ 293-MSR clones digested with BglII.

FIG. 11 is a Western blot of sublones generated by flp recombination of potential Flp-In™ 293-MSR clones with pcDNA6/FRT/TO/CAT and probed with anti-CAT antibody.

FIG. 12 is a bar graph of β-galactosidase activity in Flp-In 293 MSR subclones after recombination with pcDNA6/FRT/TO/CAT.

FIG. 13 is a photograph of a tissue culture dish X-gal stained for β-galactosidase activity used to determine which T-REx 293 MSR clones are tightly controlled by the tet repressor.

FIG. 14 is a bar graph of β-galactosidase activity expressed from a lacZ gene under the control of a tetracycline inducible promoter (upper panel) and fold induction of β-galactosidase activity (lower panel) both panels show expression in the presence and absence of tetracycline (5 μg/ml).

FIG. 15 is a bar graph showing percent cell retention of 293-H, 293 MSR, and T-REx 293 MSR cells after the indicated treatments.

FIG. 16 is a photograph of a tissue culture dish showing T-REx 293 and T-REx 293 MSR cells transiently transfected with the lacZ gene under the control of the tetracycline inducible promoter in the presence and absence of tetracycline at 5 μg/ml.

FIG. 17 is a photograph of tissue culture dishes stained with crystal violet to show the presence or absence of cells attached to the dish before and after enzymatic digestion and or chelation of attachment factors. The indicated cell lines were treated as shown.

FIG. 19 shows the number of tissue culture flasks required to utilize the same number of adherent 293 cells as FreeStyle™ 293 cells in one liter of suspension culture.

FIG. 24 shows expression of several reporter genes in shake flask format.

FIG. 25 shows a Western blot of 293FT, 293A, and T-Rex 293 cells stained for the simian virus SV40 large T antigen.

FIG. 26 shows a schematic representation of plasmids for use in making recombinant *lentivirus* using the 293FT cell line of the present invention. FIG. 26A shows a schematic representation pMDLgpRRE. FIG. 26B shows a schematic representation of pRSV/REV. FIG. 26C shows a schematic representation of pMD2-VSVG-ENV.

FIG. 27 shows plasmid maps of two versions of gene transfer vectors. FIG. 27A shows a schematic representation pRRL6/V5-DEST. FIG. 27B shows a schematic representation of pRRL6/V5-dTOPO

FIG. 29A is a protocol for production of *lentivirus*. FIG. 29B shows in tabular form the titers of lentiviral stocks prepared with inserts of varying size.

FIG. 30 shows Western blots with anti-V5-antibody of expression of various genes in HT-1080 cells using the lentiviral expression system. The upper panel shows the expression of β-galactosidase, CAT and GFP. The lower panel shows the expression of PKC and GFP.

FIGS. 31A, 31B and 31C show expression of marker genes using the lentiviral expression system. FIG. 31A shows the expression of β-galactosidase in HT-1080 cells transduced with recombinant *lentivirus* using the Gateway™ adapted lentiviral system. FIGS. 31B and 31C show the expression of GFP using the topoisomerase adapted lentiviral system.

FIGS. 32A and 32B show results of varying the multiplicity of infection on the observed expression level of β-galactosidase in HT-1080 cells using the lentiviral expression system. FIG. 32A depicts photographs of cells X-gal stained to detect β-galactosidase activity. FIG. 32B is a graph of β-galactosidase activity as a function of MOI.

FIGS. 33A and 33B show results of transduction of HT-1080 cells, growth arrested HT-1080 cells and quiescent primary foreskin fibroblasts with lentiviral vectors prepared using the 293FT cells of the invention. FIG. 33A is a bar graph of β-galactosidase activity observed in various actively growing or G1/S arrested HT-1080 cells. FIG. 33B provides photographs of contacted-inhibited primary foreskin cells transduced with lentiviral vectors and X-gal stained to detect β-galactosidase activity.

FIG. 34 is a photograph of Primary, post-mitotic rat neurons (cortical or hippocampal), transduced in duplicate at an MOI of 1, four days after plating with either RRL6/V5-GW/lacZ *lentivirus* prepared in the 293FT cells of the invention or rKAT6/V5-GW/lacZ retrovirus. Three days post-transduction, the wells were X-gal stained for β-galactosidase. Wells with an "X" in them were not transduced due to limiting amounts of virus available.

FIG. 35 shows long-term expression of β-galactosidase in cells transduced with either retrovirus or *lentivirus*. The upper panel shows photographs of transduced cells X-gal stained for β-galactosidase activity after 10 days. The lower panel shows photographs of transduced cells X-gal stained for β-galactosidase activity after 6 weeks.

FIG. 36 shows recombinant *lentivirus* titers from the 293 FT cell line described herein compared to two alternate 293 T lines and 293 A.

FIG. 37 shows a picture of a tissue culture plate stained with Crystal violet. This is an example of a viral titer plate.

DETAILED DESCRIPTION OF THE INVENTION

Figure 18:
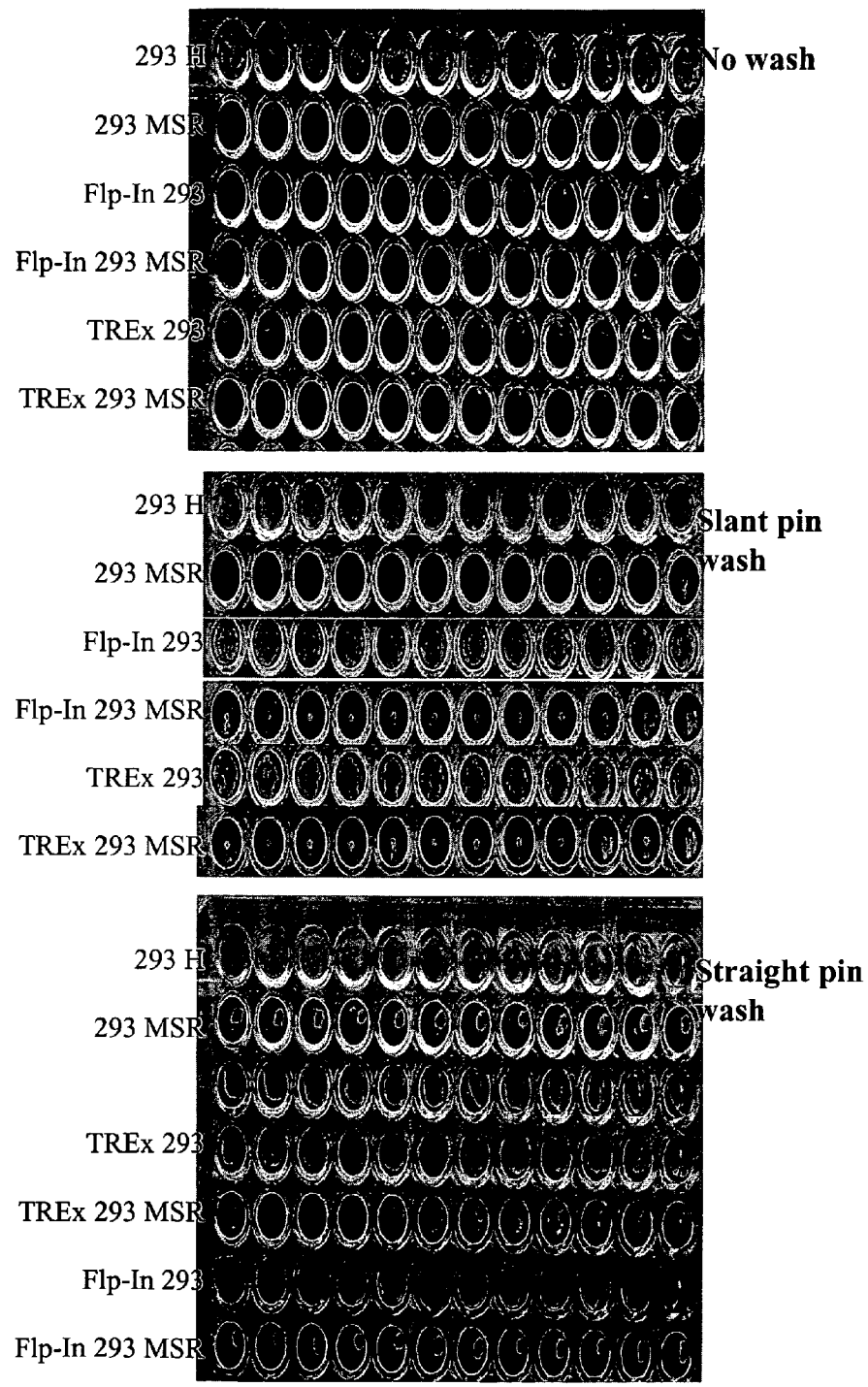
FIG. 18 is a photograph of tissue culture dishes stained with crystal violet to show the presence or absence of cells attached to the dish before and after washing with an automated plate washing device. The indicated cell lines were not washed (upper panel), washed with a slant pin apparatus (central panel), or a straight pin apparatus (lower panel).

In the discussion herein, a number of terms used in cell culture and recombinant DNA technology are utilized extensively. In order to provide a clearer and consistent understanding of the specification and claims, including the scope to be given such terms, the following definitions are provided.

Other terms used in the fields of recombinant DNA technology and molecular and cell biology as used herein will be generally understood by one of ordinary skill in the applicable arts.

"Biochemical": The term "biochemical" as used herein refers to any product produced by a cell. The product may be, but is not limited to a nucleic acid sequence, a modified nucleic acid, a modified amino acid, a polypeptide, a protein (including an enzyme), hormones, peptide factors, lymphokines, growth factors, differentiation factors, lipids, including sterols, glycolipids, amine lipids, a sugar, a modified sugar, or an enzyme modified substrate. A cell may produce one or two or several biochemical products of interest.

"Biomolecule": The term "biomolecule" as used herein refers to any biochemical as well as other small molecules, not excluding small polypeptide molecules, that can enter and effect or control happenings in a cell.

"DNA molecule": The term "DNA molecule" as used herein refers to any DNA molecule, of any size, from any source, including DNA from viral, prokaryotic, and eukaryotic organisms. The DNA molecule may be in any form, including, but not limited to, linear or circular, and single or double stranded. Non-limiting examples of DNA molecules include plasmids, vectors, and expression vectors. A DNA molecule may be a chemically modified DNA molecule or include modified nucleotides.

By "enhanced ability to attach" or "adhere more tightly" is meant that the cells of this invention attach to a solid support with sufficient avidity to resist the degree of detachment which normally occurs with the cells to which they are compared, e.g., "wild-type" 293 cells, 293-H cells, etc., caused by physical and/or chemical forces such as assay washing steps with enzyme solutions, buffer or growth medium. For example, the MSR expressing cells of this invention, because of the characteristic of enhanced attachment, provide results of, for example, two, five, seven, ten, twelve, fifteen twenty-five or even forty or more times the cell number remaining after one, two, three, four, five, six, seven or more washes as compared to the number of cells remaining following a like number of washes of "wild-type" cells. Improved adherence can be measured by time of washing, number of washings, angle of introduction of washing solution, concentration of chemical agent, and or physical force, if known. Indications of improved adherence can be selected from improved numbers of cells remaining after washing, for example, percentage of cells remaining after washing compared with prewashing; coverage area on a solid support matrix, for example a minimum surface area or a percent comparison or surface area covered pre and post wash; any indicator of cell activity, for example a minimum signal level or a comparison pre and post wash; light scatter turbidity or other measure of clear solid matrix surface, either as a maximum or a pre-post wash comparison. Improvement may be great or small, so long as the improvement meets a threshold need or results in an improvement in data obtained or ease of obtaining the data. For example, about a ten or twenty percent improvement is sometimes beneficial or adequate. Preferably an improvement in retention of about 25%, 30%, 40%, 50%, 60%, 2/3, 70%, 75%, 80%, 90%, 95% or even about 99% will be achieved to benefit the ease of obtaining and quality of data. For example, a wash protocol might remove 80, 90, 99 or even 100 percent of non-inventive cells. Cells of the invention may demonstrate improved adherence such that about 20%, 25%, etc. of the total starting cells might be retained. Similarly, if measured with the number of non-inventive retained cells after washing as a base, adequate or beneficial improvement might be seen with an even larger percent retention. For example, if a washing procedure typical removed 95% of non-inventive cells, a 100% improvement would be observed if only 90% were removed by practicing the present invention. In this example a 2000% improvement would be possible. Depending on numbers of non-inventive cells typically removed, a percent improvement of about 10%, 20%, 25%, 30%, 40%, 50%, 60%, 2/3, 70%, 75%, 80%, 90%, 100% 150% 200%, 300%, 400%, 500%, 600%, 700%, 800%, 9005, 1000%, 1500%, 2000%, 3000%, 500%, or even more for procedures removing great amounts of non-inventive cells might be observed. Washing may be automated or manual, by pipette (including multi channel pipettor), by plate washing apparatus, by virtually any liquid delivery system (preferably controlled in volume and/or pressure and or delivery speed (sheer) and/or angle. Embodiments of the present invention allow use of washing protocols normally incapable of retaining adequate cell mass or numbers.

"Expression": The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is a biochemical, expression includes the creation of that biochemical and any precursors.

"Gene": The term "gene" as used herein refers to a nucleic acid sequence that contains information necessary for expression of an RNA, a polypeptide, a protein or a biochemical. For functionality it includes the promoter and the structural gene as well as other control sequences involved in polymerization of the RNA and/or expression of the polypeptide, protein, or biochemical. Control sequences may be those naturally associated with the gene or may be control sequences from other genes.

"Gene of Interest" or "GOI": The term "gene of interest", commonly shortened to "GOI", refers to any sequence of nucleic acid that a researcher may be interested in expressing. It may be a complete or partial gene. It may be a composite of sequences from one or more organisms.

"Structural gene": The term "structural gene" as used herein refers to a DNA sequence that is transcribed into messenger RNA that is then translated into a sequence of amino acids characteristic of at least one specific polypeptide.

"Host": The term "host" as used herein refers to any prokaryotic or eukaryotic microorganism or cell that is or is to be the recipient of an expression vector, cloning vector, virus, recombinant virus, or any nucleic acid molecule including inhibitory nucleic acid molecules. The nucleic acid molecule may contain, but is not limited to, a recognition sequence, a structural gene, a promoter and/or an origin of replication.

"Recombinant host": The term "recombinant host" as used herein refers to any prokaryotic or eukaryotic microorganism or cell which contains at least one desired cloned sequence in an expression vector, cloning vector virus, recombinant virus, or any other nucleic acid molecule. The term "recombinant host" is also meant to include those host cells that have been genetically engineered to contain the desired chemical sequence on a host chromosome or in the host genome.

"Incorporating": The term "incorporating into" as used herein means becoming a part of a DNA and/or RNA molecule or primer especially any nucleic acid that exists in a host cell. Similarly, an expression product when expressed in a host cell may be said to be incorporated in the host cell.

"Inducer": The term "inducer" as used herein refers to an agent that triggers transcription from an operon, for example, a molecule that triggers gene transcription by binding to a regulator protein such as a repressor.

"Induction": The term "induction" as used herein is the switching on of transcription, for example, as a result of interaction of an inducer with a positive or negative regulator.

"Insert" or "Inserts": The terms "insert" or "inserts" as used herein include a desired nucleic acid segment or a population of nucleic acid segments that may be manipulated in accordance with the methods of the present invention. Thus, the terms insert(s) are meant to include a particular nucleic acid (preferably DNA) segment or a population of segments. Such insert(s) can comprise one or more genes.

"Nucleotide": The term "nucleotide" as used herein refers to a base-sugar-phosphate combination. Nucleotides are monomeric units of a nucleic acid sequence (DNA and RNA). Nucleotides may also include mono-, di- and triphosphate forms of such nucleotides. The term nucleotide includes ribonucleoside triphosphates, for example, ATP, UTP, CTG, GTP and deoxyribonucleoside triphosphates such as dATP, dCTP, dITP, dUTP, dGTP, dTTP, or derivatives thereof. Such derivatives include, for example, [α-S] dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. Other non-limiting examples of nucleotide analogs can be found in the World Intellectual Property Organization (WIPO) Handbook on Industrial and Documentation, Standard ST.25 (1988), including without limitation those listed therein in Tables 1 through 6.

"Labeled Nucleotide": According to the present invention, a "nucleotide" may be unlabeled or detectably labeled by well-known techniques. Detectable labels include, for example, radioactive isotopes, fluorescent labels, chemiluminescent labels, bioluminescent labels and enzyme labels.

"Polynucleotide": The term "polynucleotide" as used herein refers to a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides (relatively short polynucleotides), genes, vectors, plasmids, and the like. Polynucleotides are capable of hybridizing with complementary nucleic acid segments.

"Primer": The term "primer" as used herein refers to a single-stranded oligonucleotide molecule that is extended by covalent bonding of nucleotide monomers during amplification or polymerization of a DNA molecule.

"Promoter": The term "promoter" as used herein refers to a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

"Recognition sequence": The term "recognition sequence" as used herein refers to particular sequences which a protein, chemical compound, DNA, or RNA molecule (e.g., restriction endonuclease, a modification methylase, or a recombinase) recognizes and binds. In the present invention, a recognition sequence will usually refer to a recombination site. For example, a recognition sequence for FLP recombinase is FRT comprised of two direct 13 base pair repeats followed by an 8 base pair core region and an imperfect inverted copy of the 13 base pair repeat. See FIG. 10 of Gronostajski, R., *Journal of Biological Chemistry* 260:12320–12327 (1985). Other examples include, a recognition sequence for Cre recombinase, loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521–527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). See Landy, *Current Opinion in Biotechnology* 3:699–707 (1993). Such sites may be engineered to enhance production of products in the methods of the invention.

"Repression": The term "repression" as used herein refers to inhibition of transcription effected by the binding of a repressor, for example, a repressor protein, to a specific site on DNA.

"Repressor": The term "repressor" as used herein refers to a biochemical, commonly a protein which prevents transcription by binding to a specific site on DNA.

"Retrovirus": As used herein, retroviruses, viruses that require a reverse transcriptase activity to complete their lifecycle, are seen to include by way of example, but are not limited to, any member of the family retroviridae including human immunodeficiency viruses, bovine immunodeficiency virus, bovine leuukemia virus, human T-lymphotrophic viruses, caprine arthritis-encephalitis virus, equine infectious anemia virus, feline immunodeficiency virus, feline sarcoma and leukemia viruses, maedi/visna virus of sheep, mouse mammary tumor virus, simian immunodeficiency virus and other retroviruses known to those skilled in the art.

"Selectable marker": The term "selectable marker" as used herein refers to a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) DNA segments that encode products which provide resistance against otherwise toxic compounds (e.g., antibiotics); (2) DNA segments that encode products which are otherwise lacking in the recipient cell (e.g, tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1–5 above (e.g., antisense oligonucleotides); (7) DNA segments that bind products that modify a substrate (e.g., restriction endonucleases); (8) DNA segments that can be used to isolate or identify a desired molecule (e.g specific protein binding sites); (9) DNA segments that encode a specific nucleotide sequence which can be otherwise non-functional (e.g., for PCR amplification of subpopulations of molecules); (10) DNA segments, which when absent, directly or indirectly confer resistance or sensitivity to particular compounds; (11) DNA segements that encode RNA products that inhibit the expression of host or other expressed peptides or proteins (e.g., small interfering RNA); and/or (12) DNA segments that encode products that are toxic in recipient cells.

"Sequence": The term "sequence" as used herein refers to the chemical structure of a nucleic acid or polypeptide as well as the molecule represented by that structure.

"Solid support": The term "solid support" as used herein refers to any surface used for culturing, for in vitro assays, and the like. For example, a typical solid support is a plastic or glass tissue culture flask, a tissue culture plate, or a multi-well plate, hollow fibers, a test tube, plastic beads, glass beads, etc. Other solid supports are well known to those of skill in the art.

"Target Cell": The term "target cell" as used herein refers to any cell to which a desired compound is delivered. A target cell can be a host cell.

"Transfection": The term "transfection" as used herein refers to delivery of a nucleic acid or protein to a target cell, such that the target cell is rendered capable of expressing said nucleic acid or the protein is able to participate in a biological function, by any conventional methodology including, but not limited to, dextran-mediated transfection, calcium phosphate precipitation, polybrene mediated transfection, electroporation, mechanical transfection, and encapsulation of the polynucleotide(s) in liposomes. It will be understood that the term "nucleic acid" includes DNA and RNA and chimers thereof without regard to molecular weight or to modifications.

"Unit": The term "unit" as used herein refers to measurement of the activity of an enzyme. When referring, for example, to a DNA polymerase, one unit of activity is the amount of enzyme that will incorporate 10 nanomoles of dNTPs into acid-insoluble material (i.e., DNA or RNA) in 30 minutes under standard primed DNA synthesis conditions.

"Variant": The term "variant" as used herein refers to any "variant" of a specified cell line including progeny of the specified cell line, a modified or mutated cell line obtained or derived from the specified cell line or its progeny, or other recipient cell line that contains genetic material obtained directly or indirectly from the specified cell line. Such a variant cell line may, for example, be formed by removing genetic material from a specified microorganism or cell line and subsequently introducing it into a cell line (i.e., the progeny or other recipient cell line) by any conventional methodology including, but not limited to, dextran-mediated transfection, calcium phosphate precipitation, polybrene mediated transfection, protoplast fusion, electroporation, encapsulation of the polynucleotide(s) in liposomes, direct microinjection of the DNA into nuclei, transduction, differentiation and the like. A variant may be formed by introducing one or more mutations or modifications into the genome or other genetic material (e.g., vectors, plasmids, extrachromosomal elements, etc.) of a cell line. Such mutations or modifications may include one or more insertion mutations, deletion mutations and/or substitutions or various combinations thereof. The mutations or modifications may be insertions into the genome or other genetic material (e.g., vectors, plasmids, extrachromosomal elements, etc.) of the cell line. Alternatively, the mutations may be deletions of one or more bases and/or nucleic acid sequences from the genome or other genetic material (e.g., vectors, plasmids, extrachromosomal elements, etc.) of the cell line. In some instances, the mutations may be the alteration of one or more bases in the genome of the cell line. Such modifications or mutations may also comprise, for example, methylating or possibly substituting one or more nucleic acid bases and/or nucleic acid molecules for other nucleic acid molecules and/or bases. In addition, one cell line is a variant of a parent cell line if it contains the genome of the parent cell line but does not contain some or all of the same extrachromosomal nucleic acid molecules. Variants of a cell line of the invention may also include those cell lines obtained by the addition of one or more nucleic acid molecules into the cell line of interest. Nucleic acid molecules which may be introduced into a cell line will be recognized by one skilled in the art and may include, but are not limited to, vectors, plasmids, oligonucleotides, RNA, DNA, RNA/DNA hybrids, phage sequences, virus sequences, regardless of the form or conformation (e.g., linear, circular, supercoiled, single stranded, double stranded, single/double stranded hybrids and the like). Examples of mutations or other genetic alterations which may be incorporated into the cell line of the present invention include, but are not limited to, mutations or alterations that create: a cell line resistant to antibiotic selection, a cell line with increased permissiveness to transfection; a cell line with increased expression of transgenes; genomic incorporation of a gene of interest in a cell line; and genomic incorporation and amplification of a gene of interest in a cell line. Other suitable modifications are known to those skilled in the art and such modifications are considered to be within the scope of the present invention.

"Vector": The term "vector" as used herein refers to a plasmid, phagemid, cosmid, virus or phage nucleic acid or other nucleic acid molecule that is able to replicate autonomously or to be replicated in a host cell. Preferably a vector is characterized by one or a small number of restriction endonuclease recognition sites at which such nucleic acid sequences may be cut in a determinable fashion without loss of an essential biological function of the vector, and into which nucleic acid molecules may be spliced in order to bring about replication and cloning. The cloning vector may further contain one or more markers suitable for use in the identification of cells transformed with the cloning vector. Markers, for example, are antibiotic resistance genes including, but not limited to tetracycline or ampicilin resistance, hygromycin B or neomycin resistance; and/or fluorophores, including, but not limited to green fluorescent protein or β-lactamase.

"Cloning vector": A plasmid or phage DNA or other DNA sequence which is able to replicate autonomously in a prokaryotic host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline or ampicillin resistance or are fluorophores, including, but not limited to green fluorescent protein or β-lactamase.

"Expression vector": The term "expression vector" as used herein refers to a vector similar to a cloning vector but which is capable of enhancing the expression of a gene which has been cloned into it, after transfection into a host. The cloned gene is usually placed under the control of (i.e., operably linked to) certain control sequences such as promoter sequences.

"Virus": As used herein, any protein encased nucleic acid or derivative thereof capable of entering a host cell and causing replication of that nucleic acid and/or expression of a nucleic acid and/or polypeptide encoded by that nucleic acid.

"Wild type": As used herein, wild type refers to a naturally occurring type, a type isolated from nature or a standard type, for example, a cell line before manipulation or engineering.

In the disclosure and the claims, "and/or" means additionally or alternatively. Moreover, any use of a term in the singular also encompasses plural forms.

Adherent Culture

The Human Embryonic Kidney cell line (HEK 293) is widely used for expression of recombinant protein and adenovirus production. These cells are used extensively as examples throughout the discussion of the present invention. The "wild type" 293 cells adhere only weakly to standard tissue culture supports making these cells difficult or unsuitable for use in automated formats and requiring special care in normal cell culture procedures. Expression of the human Macrophage Scavenger Receptor Type I (MSR) gene increases adherence to tissue culture plastic and other solid support matrices.

There is an obvious need in the field for cell culture lines appropriate to both high-efficiency transfection and/or automated protocols. Among suitable cell lines the Human Embryonic Kidney cell line (HEK 293) is a common, transfectable cell line capable of high-level gene expression. Like most cell lines used in research and screening purposes, the "wild-type" 293 cell is very difficult to use in automated formats.

Many variants of the HEK 293 cell line are available with a wide array of characteristics. The fast-growing, easily transfectable and adherent 293-H cell line was originally isolated by Leaf Huang at U. Pittsburgh. Subclones were isolated and screened for high-efficiency transfection and increased adherence properties. The GIBCO® 293-H cell line (Invitrogen Corporation, Carlsbad, Calif.) is a fast-growing, high-transfection efficiency, high-expression, adherent 293 cell line. However, useful as this cell line is, this cell line is best used with poly-lysine coated plates to optimize adherence. Poly-lysine introduces increased expense and the additional variable increases uncertainty in high-throughput protocols.

Scientists at SmithKline Beecham created a 293 MSR cell line that exhibited significantly better adhesion qualities as compared to 293 "wild-type" or parental cells. See the above-mentioned Lysko patents. One aspect of the present invention incorporates the MSR technology into the GIBCO® 293-H cell line, resulting in a fast-growing, high-transfection efficiency, high-expression, 293 cell line that adheres especially well to solid matrices such as tissue culture plastic. This cell eliminates the need to use expensive specially coated plates and allows the use of these cells in a number of automated formats, especially high throughput formats such as multi-well plate formats.

By way of example the MSR gene was transfected into GIBCO® 293-H. Geneticin® resistant clones were selected and screened for resistance to trypsinization and expression of transiently transfected β-galactosidase or luciferase. See FIG. 3. Increased adherence to tissue culture supports was demonstrated in the GripTite™ 293 cell line using various cell-washing protocols See FIGS. 4–7. This cell line allows high-throughput protocols to be used with the HEK 293 cell line without significant cell loss from conventional and even more rigorous processing protocols. See FIGS. 6 and 7.

These cells named 293-H MSR or GripTite™ 293 MSR (Invitrogen Corporation, Carlsbad, Calif.) demonstrate advantages as compared to 293 MSR (Lysko) and GIBCO® 293-H. These advantages are especially evident when using plate scanning devices, plate reading devices and other adherent cell dependant cell detection devices as well as multi-channel pipettors, plate washers and/or a liquid-handling robot.

By way of example, the GripTite™ 293 MSR, GIBCO® 293-H and Lysko cells were transiently transfected with a plasmid encoding the lacZ gene and the activity of the expressed β-galactosidase determined using the ONPG assay. FIG. 2 shows the significantly higher transgene expression in the GripTite™ 293 MSR, GIBCO® 293-H cell lines as compared to the Lysko 293 MSR cell line.

The present invention thereby provides as one embodiment an improved cell line, for example, an improved human embryonic kidney cell line, 293-H MSR. The inventors have surprisingly found in one aspect that human embryonic kidney (HEK) 293 cells transfected with a mammalian macrophage scavenger receptor gene demonstrate an enhanced ability to attach to a solid support as compared to conventional, unmodified 293 cells, or even 293 cells that already demonstrated enhanced adherence characteristics as well as high transfection efficiency and transgene expression. In contrast to unmodified or other previously known 293 cells, the improved 293 cells of the invention are not as readily washed away as unmodified 293 cells under the normal conditions of biological assays and are easily transfectable. Essentially, GIBCO® 293-H cells expressing the Macrophage Scavenger Receptor (MSR) adhere more tightly to tissue culture plastic than parental HEK 293-H cell lines and are more easily transfected than the Lysko 293 MSR cell line. Thus, the improved 293 cells of the invention are particularly well suited for use in in vitro studies and other applications for which unmodified 293 cells may be used.

The human embryonic kidney cell line, 293, is readily available, e.g., from the American Type Culture Collection, 10801 University Blvd, Manassas, Va., U.S.A., under accession number ATCC CRL 1573. Exemplary cells of the present invention are on deposit at the ATCC.

Also encompassed by this invention are progeny and derivatives of the cell lines specifically exemplified and/or denosited with the ATCC in conjunction with this application. For example, the following cell lines were deposited on Mar. 24, 2003 with the American Type Culture Collection, 10801 University Blvd., Manassas, Va, 20110-2209: FlpIn MSR (PTA-5076), 293FT (PTA5077), 293-H MSR (PTA5078), 293 MSR tet:R Hyg (PTA-5079), and FreeStyle®. (PTA5030). Progeny and/or derivatives may be prepared using conventional techniques. See, e.g., Sambrook, *Molecular Cloning: A Laboratory Manual,* 2d ed., Cold Spring Harbor Press, Cold Spring Harbor, N.Y. (1989).

According to this invention, cells can be modified by transfection for example, with a selected mammalian macrophage scavenger receptor (MSR) gene. Currently, in a preferred embodiment, this gene is selected from a human MSR Type I or Type II gene, and most preferably, the gene is characterized by the sequence provided in GenBank, under accession number D90187 (MSR Type I) or D90188 (MSR Type II). The sequences SEQ ID NO:1 and 2 of MSR Type I are provided in FIG. 1 of Lysko. The sequences SEQ ID NO:3 and 4 of MSR Type II are provided in FIG. 2 of Lysko. According to Lysko, both of these genes were obtained from the human monocytic cell line THR-1 following 4 days of phorbol ester treatment. These two gene sequences are differential splice variants of a single human gene, and are described in more detail in Matsumoto, A., et al., *Proc. Natl. Acad. Sci. USA* 87:9133–9137 (1990), incorporated by reference herein.

The MSR protein is a trimeric integral membrane protein that recognizes polyanionic ligands, low density lipoproteins, bacterial endotoxins, lipopolysaccharides, and, especially relevant to the current invention, tissue culture treated plastic. See FIG. 1. The protein is implicated in the pathologic deposition of cholesterol during atherogenesis and in host defense against microbial pathogens.

The present inventors expect that non-human homologs of MSR I or MSR II will be similarly useful in preparing the improved cells, for example, human 293 cells according to the invention. Particularly desirable are the bovine (Kodama, T., et al., *Proc. Natl. Acad. Sci. USA* 85:9238–9242 (1988)), murine (Freeman, M., et al., *Proc. Natl. Acad. Sci. USA* 87:8810–8814 (1990)) and rabbit (Bickel, P. E. and Freeman, M. W., *J. Clin. Invest.* 90:1450–1457 (1992)) homologs, each of which is at least 60–80% homologous with the human MSR genes. It is further anticipated that other human scavenger receptor genes, particularly other genes that are produced recombinantly or are differentially selective for oxidized or acetylation-modified low density lipoprotein (LDL) species or another desired lipoprotein species, will be similarly useful.

In one embodiment of the present invention, one of these genes, preferably a human MSR gene, is selected and cloned into an appropriate vector for use in transfecting a host cell, e.g., a 293 cell such as the preferred GIBCO® 293-H cell available from Invitrogen Corporation.

Generally, a suitable expression vector is one that contains control or regulatory sequences operably linked with the nucleic acid sequences of the gene of interest, e.g., an MSR gene. These regulatory sequences are capable of directing the expression of the gene product in the host cell, for example, 293 cells. The MSR under the control of a tetracycline inducible promoter would express the MSR protein only in the presence of tetracycline. This allows the controlled deposition of cells on a tissue culture surface. Suitable vectors and regulatory sequences are well known to those of skill in the art and this invention is not limited by the selection thereof.

For example, suitable vectors may be, or contain components from, viral vectors selected from simian virus SV40, retroviruses, bovine papilloma virus, vaccinia virus, and adenovirus, or commonly used bacterial vectors or commonly used insect and/or mammalian expression vectors or integrative vectors which lead to a stable expression cell line. The vector used in some examples below is pCMV Sport 6 (Ohara, O., Temple, G., *Nucleic Acids Research* 29:E22 (2001)), which contains the promoter from cytomegalovirus, followed by an att B λ integrase recombination site and a polyadenylation site, the SV40 early enhancer, and a gene conferring resistance to neomycin.

Methods for introduction of a vector, e.g., a vector containing an MSR gene or other adherence enhancing gene into mammalian cells are well known. Examples of suitable methods include, without limitation, dextran-mediated transfection, calcium phosphate precipitation, polybrene mediated transfection, protoplast fusion, electroporation, encapsulation of the polynucleotide(s) in liposomes, viral transduction and direct microinjection of the DNA into nuclei, etc.

The Human Embryonic Kidney cell line, HEK 293, has been widely used for expression of recombinant protein and adenovirus production and thus serves as a broadly applicable example of the present invention. These native cells adhere weakly to standard tissue culture supports. In a preferred embodiment the human Type 1 Macrophage Scavenger Receptor (MSR) was transfected into the GIBCO® 293-H cell line (Invitrogen). Clones were screened for resistance to trypsinization and permissiveness to transfection. In other embodiments the tetracycline repressor (tetR) gene was transfected into the resulting 293-H MSR cell line to create 293 T-REx MSR and a single FRT site was inserted into 293-H MSR to create a cell line referred to as 293 Flp-In MSR. Increased adherence to tissue culture supports has been demonstrated in these examples using various cell-washing protocols. See FIGS. 7–18.

Sequences which contain selectable markers may also be transfected into the cell line. These markers may be contained on the vector containing the MSR gene, or may be separately transfected using conventional techniques, such as those described herein and elsewhere in the art. Selectable markers for mammalian cells are known in the art, and include for example, thymidine kinase, dihydrofolate reductase (together with methotrexate as a DHFR amplifier), aminoglycoside phosphotransferase, hydromycin B phosphotrans-ferase, asparagine synthetase, adenosine deaminase, metallothionien, and antibiotic resistant genes such as neomycin. Other markers may be readily selected by one of skill in the art, as desired.

As described in more detail below, if an MSR transfected cell is desired for use in a screening assay, the cell may also be transfected with other genes. The additional gene(s) may, for example, encode a protein, which will be screened for biological activity or for interaction with the MSR or another transfected gene, such as a marker.

Following transfection with the selected MSR gene (and optionally, any other gene), the cells are incubated in a suitable selection medium, e.g., Eagles MEM, Dulbecco's MEM or the like.

Once modified to contain the adherence enhancing gene, e.g., an MSR gene, or another suitable gene, according to the methods described above, the improved host cells, e.g., 293 cells, are particularly well suited for use in any assay in which an unmodified 293 cell may be used. Advantageously, the use of the improved 293 cells of the invention will result in superior attachment, and thus, more dependable, reproducible and accurate test results.

An exemplary use of the improved 293 cells of the invention includes the use of the cells in a method of screening compounds for biological activity. This method may involve use of the attachment enhanced 293 cells of the invention, which have been further transfected with a selected gene sequence. These cells are subsequently screened for expression of the selected gene. The cells expressing these selected genes are then incubated in the presence of a compound of unknown biological activity and further assayed for the ability of the compound to affect the expressed gene product.

Similarly, the attachment enhanced 293 cells and other cells of the invention may be used to identify antagonists of the MSR gene, i.e., to develop agents, e.g., for atherosclerosis. Suitable assays for identifying antagonists to an expressed gene product are well known to those of skill in the art. (e.g., Kodama, T., et al., *Nature* 343:531–535 (1990), Pearson, A. M., et al., *J. Biol. Chem.* 268:3554 (1993)).

Suspension Culture

There is an obvious need in the field for cell culture lines appropriate to both high-efficiency transfection and/or growth in suspension. Bioproduction level human biochemical production requires very large cell numbers. Bioproduction facilities range from 1 liter to 10,000 liter bioreactors. FIG. 19 lists the number tissue culture flasks required for $1 \times 10^9$ cells which is equivalent to a 1 liter bioreactor. The ability to culture cells in suspension reduces the physical space required to produce biochemicals. It is apparent that suspension culture has advantages in bioproduction or in assays advantageously using suspension cell culture. Among suitable cell lines, the Human Embryonic Kidney cell line (HEK 293) is a common, transfectable cell line capable of high level gene expression resulting in human biochemicals. Like most cells used for suspension production of biochemicals, the "wild-type" 293 cell line is difficult to use in animal component free suspension culture.

Many variants of the HEK 293 cell line are available with a wide variety of characteristics. The fast-growing easily transfectable and semi-adherent 293-F cell line was originally isolated at Cold Spring Harbor. This cell line was adapted to growth in serum free suspension culture. Subclones were isolated and screened for high-efficiency transfection and increased expression of transgenes. The GIBCO® 293-F cell line (Invitrogen Corporation, Carlsbad, Calif.) is a fast-growing, high-transfection efficiency, high-expression, adherent or suspension 293 cell line. However useful as this cell line is, its growth and transgene expression is dependant on certain animal derived factors. The GIBCO® 293-F cell line was adapted to suspension growth in a cell culture media that hindered efficient transfection.

Scientists at Invitrogen developed a cell culture media containing no components of animal origin. GIBCO® 293-F cells were adapted to growth in this media and scientists were surprised to find extremely high levels of transgene expression. These adapted cells are called FreeStyle™ 293, and are one aspect of the present invention.

The characteristics required for animal component free transfection and expression of human biochemicals include but are not limited to high efficiency transfection in suspension media, high level expression of transgenes, fast growth in suspension media, adaptability to various suspension cell culture formats and protocols.

The present invention thereby provides as one embodiment an improved human embryonic cell line FreeStyle™ 293. The inventors have surprisingly found that human embryonic kidney (HEK) 293 cells adapted first to growth in suspension media; subclones isolated and screened for high transfection efficiency and transgene expression; and finally adapted into suspension culture in a media free of any animal derived component demonstrate an enhanced transfection efficiency and transgene expression as compared to conventional "wild-type" 293 cells or even derivative cells that demonstrated growth in suspension culture. Exemplary cells of the present invention are on deposit at the ATCC.

Also encompassed by this invention are progeny and derivatives of the cell lines specifically exemplified and/or depositied with the ATCC in conjunction with this application. For example the FreeStyle™ 293 cell line has been deposited with the ATCC. Progeny and/or derivatives may be prepared using conventional techniques. See, e.g., Sambrook, *Molecular Cloning: A Laboratory Manual,* 2d ed., Cold Spring Harbor Press, Cold Spring Harbor, N.Y. (1989).

Human cell culture is often the preferred vehicle for expression of human biochemicals for research and for clinical use. However, there have been many obstacles to using human cell culture systems for biochemical production including the requirement for a solid support and serum for cell growth. The FreeStyle™ 239 cells allow scalable biochemical expression in many formats and volumes without optimization for each. See FIG. 20 for a comparison of β-galactosdiase expression in bioreactor and shake flask formats. These cells provide high level expression of both secreted and intracellular biochemicals in cell culture. See FIGS. 20–24.

Once modified to high efficiency transfection and high level transgene expression in animal component free suspension culture, improved host cells, e.g. FreeStyle™ 293 cells, are particularly well suited for use in bioproduction or in any homogenous assay in which an unmodified non-adherent 293 cell may be used. However the use of the improved 293 cells of the invention will result in superior transfection, and thus, more dependable reproducible and accurate test results.

An exemplary use of the improved 293 cells of the invention includes the use of the cells in a method of screening compounds for biological activity. This method may involve the use of the dispersal of the enhanced 293 cells of the invention, which have been further transfected with a selected gene sequence. These cells are subsequently screened for expression of the selected gene. The cells expressing these selected genes are then incubated in the presence of a compound of unknown biological activity and further assayed for the ability of the compound to affect the expressed gene product.

In one embodiment of the present invention, one of these genes, preferably a human gene, is selected and cloned into an appropriate vector for use in transfecting a host cell, e.g., a 293 cell such as the preferred FreeStyle™ 293 cell available from Invitrogen Corporation.

Generally, a suitable expression vector is one that contains control or regulatory sequences operably linked with the nucleic acid sequences of the gene of interest. These regulatory sequences are capable of directing the expression of the gene product in the host cell, for example, FreeStyle™ 293 cells. Suitable vectors and regulatory sequences are well known to those of skill in the art and this invention is not limited by the selection thereof.

For example, suitable vectors may be, or contain components from, viral vectors selected from simian virus SV40, retroviruses, bovine papilloma virus, vaccinia virus, and adenovirus, or commonly used bacterial vectors or commonly used insect and/or mammalian expression vectors or integrative vectors which lead to a stable expression cell line.

Methods for introduction of a vector into mammalian cells are well known. Examples of suitable methods include, without limitation, dextran-mediated transfection, calcium phosphate precipitation, polybrene mediated transfection, protoplast fusion, electroporation, encapsulation of the polynucleotide(s) in liposomes, viral transduction and direct microinjection of the DNA into nuclei.

The Human Embryonic Kidney cell line, HEK 293, has been widely used for expression of recombinant protein and adenovirus production and thus serves as a broadly applicable example of the present invention. The "wild-type" cells adhere weakly to standard tissue culture supports. In a preferred embodiment, genes are expressed using the improved 293 cells in multiple formats. In one example of such expression, β-galactosidase and luciferase were expressed in a bioreactor and shake flasks, see FIGS. 20 to 24.

Sequences which contain selectable markers may also be transfected into the cell line. These markers may be contained on the vector containing the gene of interest, or may be separately transfected using conventional techniques, such as those described herein. Selectable markers for mammalian cells are known in the art, and include for example, thymidine kinase, aminoglycoside phosphotransferase, hydromycin B phosphotransferase, asparagine synthetase, and adenosine deaminase. Other markers may be readily selected by one of skill in the art, as desired.

Host cells, for example HEK 293 host cells, and preferably a fast growing cell line with improved ease of transfection or transduction, or other desired quality, may be transduced with, e.g., viruses. A preferred virus is a virus with a receptor on the host cell or other host cell factors that allow improved expression from viral vectors. Because HEK 293 cells contain several adenoviral genes, replication incompetent adenoviral vectors easily transduce 293 cells.

In one embodiment of the present invention, FreeStyle™ 293 cells are transduced with replication incompetent adenovirus to produce a desired biochemical.

In another embodiment of the present invention, FreeStyle™ 293 cells are used to produce replication incompetent adenovirus fro use as a vaccine, a therapeutic or a reagent.

Retroviruses are RNA viruses that reverse transcribe their genome and integrate a DNA copy into at least one chromosome of the target cell. It was discovered that the retroviral packaging proteins (gag, pol and env) could be supplied in trans, thus allowing the creation of replication incompetent viral particles capable of stably delivering a gene of interest. These retroviral vectors have been available for gene delivery for many years (Miller et. al., *BioTechniques* 7:980–990 (1989)). One significant advantage of retroviral-based delivery is that the gene of interest is stably integrated into the genome of the host cell with very high efficiency. In addition, no viral genes are expressed in these recombinant vectors making them safe to use both in vitro and in vivo. However, one main drawback to the traditional Moloney-based retroviruses is that the target cell must undergo one round of cell division for nuclear import and stable integration to occur. Traditional retroviruses do not have an active mechanism of nuclear import and therefore must wait for the host cell nuclear membrane to breakdown during mitosis before they can access the host genomic DNA, see Miller et. al., *Mol. Cell. Biol.* 10:4239–4242 (1990).

Unlike traditional retroviruses, HIV (classified as a "*lentivirus*") is actively imported into the nuclei of non-dividing cells see Miller et. al., *BioTechniques* 7:980–990 (1989). HIV still goes through the basic retrovirus lifecycle (RNA genome reverse transcribed in the target cell and integrated into the host genome); however, cis-acting elements facilitate active nuclear import, allowing HIV to stably infect non-dividing cells. For reviews see Buchschacher et. al., *Blood* 95:2499–2504 (2000); Naldini et. al., *The Development of Human Gene Therapy*, Cold Spring Harbor Laboratory Press, (1999), pp. 47–60. It is important to note that, for both *lentivirus* and traditional retroviruses, no gene expression occurs until after the viral RNA genome has been reverse transcribed and integrated into the host genome.

Similar to other retrovirus expression systems, the packaging functions of HIV can be supplied in trans, allowing the creation of lentiviral vectors for gene delivery. With all the viral proteins removed, the gene delivery vector becomes safe to use and allows foreign DNA to be efficiently packaged. In addition, it has been shown that lentiviral (or any retroviral) envelope proteins can be substituted for ones with broader tropism. The substitution of envelope is called pseudotyping, and allows creation of lentiviral vectors capable of infecting a wider variety of cells than CD4+ cells. Many have found that the G protein from vesicular stomatitis virus (VSV-G) is an excellent pseudotyping envelope protein that imparts a very broad host range for the virus. See Yee et. al., *Proc. Natl. Acad. Sci. USA* 91:9564–9568 (1994). The ability of pseudo-typed *lentivirus* to infect a broad range of non-dividing cells has led to its extensive use in animal gene delivery and gene therapy. See Baek et. al., *Hum. Gene Ther.* 12:1551–1558 (2001); Park et. at., *Mol. Ther.* 4:164–173 (2001); Peng et. al., *Gene Ther* 8:1456–1463 (2001).

An exemplary virus (based loosely on HIV-1) can effectively transduce dividing and non-dividing mammalian cells (in culture or in vivo), thus broadening the possible applications beyond those of traditional Moloney (MLV)-based retroviral systems (Clontech, Stratagene, etc.). Directional TOPO® and Gateway™ lentiviral vectors (Invitrogen), based on the pRRL vector from Cell Genesys, have been created to clone gene(s) of interest with a V5 epitope, if desired. The exemplary vectors also carry the blasticidin resistance gene to allow for the selection of transduced cells. Without additional modifications, these vectors can theoretically accommodate up to ~6 kb of foreign genetic material. Three supercoiled packaging plasmids (gag/pol, rev and VSV-G envelope) are provided to supply helper functions and viral proteins in trans. Because only sequences flanked by the viral LTRs are packaged into virions (i.e. pRRL6/V5 vector). None of the three packaging plasmids contain LTRs; so while they are expressed in the producer cell, they are never packaged into the virions. The gene transfer vector pRRL6/V5 has been modified to be "self-inactivating" (Yu 1986, Yee 1987, Zufferey 1998). A deletion has been made in the 3' LTR (called "delta U3") that has no effect on the generation of viral genome for packaging in the producer cell. However once the produced virus transduces a target cell, the mechanisms of reverse transcription use the 3'LTR as a template to create the 5'LTR. The end result is an integrated viral genome that is defective in both its 5' and 3' LTRs, and is no longer capable of producing packagable viral genome. This means that transduction with the lentiviral vectors is a "one shot deal", ending with the gene of interest integrated into the host cell genome.

Because four individual plasmids are required for recombinant *lentivirus* production, a simple transfection into most commonly used cell lines will not produce useful amounts of recombinant virus. The amount of DNA that is delivered to the nucleus of a cell using most methods of transfection is limited. Because of this limitation, it was necessary to use an amplifiable system to efficiently produce recombinant *lentivirus*. The packaging plasmids pMDLgpRRE also known as pLP1 (Invitrogen) and pMD2-VSVG-Env also known as pLPVSVG (Invitrogen) contain the simian virus SV40 large T antigen binding site #2. See FIG. 26. Both pRRL vectors, pLenti6V5 DEST and pLenti6V5TOPO (Invitrogen) contain the complete simian virus SV40 origin of replication including all three large T antigen binding sites. See FIG. 27. The inclusion of these sites on the plasmid backbone promotes large T antigen mediated plasmid amplification. Because the 293FT cell line of the invention is a fast growing, easily transfectable, more DNA is initially delivered to the cell. Because the 293FT cell line of the invention is large T antigen expressing cell line, the DNA that is delivered is amplified. This improvement in the amount of DNA delivered increases the probability that all four required plasmids are available for viral growth. Because the delivered plasmid DNA is amplified, more viral particles can be made. This amplification insures recombinant virus production.

Because *lentivirus* production is dependant on genomic integtration, it is difficult to get large numbers of viral particles. The 293 FT cell line of the invention allows viral titers in the range of $10^6$ to $10^7$ per ml. Transfection of other 293 cell lines by comparison resulted in significantly fewer infectious viral particles. See FIG. 37.

The following examples illustrate in detail the preferred methods for preparing the modified cells of the invention and exemplary uses thereof. These examples are illustrative only and are not intended to limit the scope of the invention.

PRIOR ART EXAMPLES

Example 1 of U.S. Pat. No. 5,683,903

Calcium Phosphate Transfection of Macrophage Scavenger Receptor I and into Human Embryonic Kidney 293 Cells The macrophage scavenger receptor I or II cDNAs, respectively were subcloned into the mammalian expression vector pCDN in the correct orientation. (Aiyar, N., *Mol. Cell. Biochem.* 131:75–86 (1994)).

The resulting construct containing the macrophage scavenger receptor I or II cDNA was used to transfect human embryonic kidney (HEK) 293 cells by calcium phosphate. One day prior to the transfection, the HEK 293 cells were plated into 10 cm dishes at a density of $2 \times 10^5$ cells, so that the cells would be approximately 10% confluent within 24 hours for transfection. The cells were seeded into Eagle's Minimal Essential Medium (EMEM) supplemented with 2 mM L-glutamine and 10% fetal bovine serum (FBS).

The DNA was prepared for transfection by sterile ethanol precipitation. Following ethanol precipitation, the DNA pellet was dried inside a tissue culture hood. The pellet was then resuspended in 450 μL of sterile water and 50 μL of 2.5 M $CaCl_2$. Ten μg of DNA were used per 10 cm dish. While gently swirling the DNA mixture, 500 μL of sterile 2×BBS (50 mM N,N-bis 2-hydroxyethyl-2-aminoethane sulfonic acid, 280 mM NaCl and 1.5 mM $NaHPO_4$) was added. The BBS/DNA-$CaCl_2$ solution was allowed to form a precipitate by sitting at room temperature for 10–20 minutes.

The solution was then gently mixed to ensure adequate suspension of the precipitate and then added dropwise into the 10 cm dish of cells. The plate was gently swirled to distribute contents evenly. After a 12–16 hour incubation, the medium was carefully removed, and the cells were washed once with 5 ml of PBS (without $Ca^{2+}$ or $Mg^{2+}$) followed by the addition of 10 ml of EMEM supplemented with 2 mM L-glutamine and 10% FBS.

Following an overnight incubation, the medium was removed, and the cells were carefully washed once with 5 ml of PBS (without $Ca^{2+}$ or $Mg^{2+}$). To initiate selection, 10 ml of fresh EMEM with L-glutamine supplemented with 2 mM L-glutamine, 10% FBS and 0.4 mg/ml of geneticin (GIBCO-BRL) were added. Two or three days later, the medium was changed.

After approximately 2–3 weeks, each plate was examined under the microscope for small patches of growing cells. The patches were grown large enough to be seen as small spots on the bottom of the plate. Once at this stage, all of the medium was removed and 3 μL of trypsin was added directly to the patch of cells. By pipetting up and down several times, the patch of cells was transferred to a 24 well dish containing 1 ml of medium with geneticin. The cells were expanded from this 24 well stage to a 6 well plate or T-25 Flask. Because the 293 cells grow best in conditioned medium, cells were fed based on their rate of growth, but typically not more than once a week.

Example 2 of U.S. Pat. No. 5,683,903

Comparison of Transfected and Untransfected 293 Cells

To demonstrate the surprising results of the above transfection, and the greater accuracy obtained in using the transfected 293 cells (Lysko 293 MSR cells) in assays, transfected 293 cells of this invention and untransfected 293 cells were seeded at the same cell density (100,000 per well) into 24-well plastic tissue culture dishes. These cells were allowed to grow for two days before testing. Cell growth appeared to be equivalent.

The same biochemical assay was performed on the transfected and untransfected cells.

The presence of macrophage scavenger receptors was confirmed by incubating transfected 293 cells with $^{125}$I-acetylated LDL at a concentration of approximately 5 μg/ml (specific activity about 100–300 cpm/ng protein) for 5 hours at 37° C., essentially as described in Ashkenas, J., et al., *J Lipid Res.* 34:983–1000 (1993). In replicate experiments, $^{125}$I-acetylated LDL binding/uptake amounted to an average of 1.75 μg/mg protein (n=76). Where it has been possible to measure $^{125}$I-acetylated LDL binding/uptake to untransfected 293 cells, the average was 0.20 μg/mg protein (n=6).

After the assays were performed on the cells, they were dissolved in 0.1 M NaOH, and aliquots were used to determine total protein concentration by the Pierce BCA assay with bovine serum albumin as the standard. In an attempt to keep as many untranfected cells as possible attached to the culture dished, the untransfected cells were washed only twice, while the transfected cells were washed seven times as per the procedure cited above.

Superior attachment of the transfected cells was observed in a comparison of recoverable protein, with an average of 113+/−2.3 μg protein/well (n=24) versus the untransfected cells with an average of 21.8+/−4.8 μg protein/well (n=12).

PRESENT EXAMPLES

Example 1

Isolation of the MSR I Gene

The 293 MSR cell line was obtained from SmithKline Beecham. Genomic DNA was isolated from the SKB 293 MSR cell line; the MSR gene was isolated using PCR. The primers used to isolate the MSR gene and attach attB1 and attB2 sites are: 5' gene specific, 5'-GAACCATGGAG-CAGTGGGATCACTT-3' (SEQ ID NO:1), 5' attB1 linker 5'-GGGGACAAGTTTGTACAAAAAAGCAG-GCTGAACCATG GAGCAGTGGGATCACTT-3' (SEQ ID NO:2), 3' gene specific 5'-TGCATTATAAAGTGCAAGT-GACTC-3'(SEQ ID NO:3), and 3' attB2 linker 5'-GGG-GACCACTTTGTACAAGAAAGCTGGGTTGCATTATA AAGTGCAAGTGACTC-3' (SEQ ID NO:4).

```
5' gene specific,
5'-GAACCATGGAGCAGTGGGATCACTT-3',

5' attB1 linker
5'-GGGGACAAGTTTGTACAAAAAAGCAGGCTGAACCATGGAGCAGTGG

ATCACTT-3',

3' gene specific
5'-TGCATTATAAAGTGCAAGTGACTC-3',
and

3' attB2 linker
5'-GGGGACCACTTTGTACAAGAAAGCTGGGTTGCATTATAAAGTGCAAG

TGACTC-3'.
```

The resulting fragment was recombined in a B×P reaction to create an Entry clone using the Gateway™ system from Invitrogen. The Entry clone was recombined with pDEST12.2 to make an expression clone. In the final construct, pCMV Sport6 MSR.neo, the full cytomegalovirus (CMV) enhancer/promoter drives expression of the MSR I gene and the SV40 poly A signal completes the transcript.

Generation of the 293 H MSR Stable Cell Line

The 293 H MSR cell line was generated by transfecting $1 \times 10^6$ GIBCO® 293-H cells with 4 µg pCMV Sport6 MSR-.neo and 6 µl LipofectAMINE™ 2000. Twenty-four hours post-transfection the cells were trypsinized and diluted into 100 mm dishes at $10^5$, $10^4$, and $10^3$ cells per plate. Twenty-four hours after dilution, the cell culture media (DMEM, 10% FBS, 1% MEM-NEAA) was replaced with media containing 600 µg/ml Geneticin. Forty-eight distinct foci that had formed after 11 days of Geneticin selection were picked and expanded as single clones.

Generation and Screening of 293 MSR Clones

Geneticin resistant clones were tested for enhanced adherence to tissue culture plastic and permissiveness to transfection/expression.

Clones were screened for adherence and resistance to trypsinization as follows. Cells were plated $2 \times 10^5$ cells per well in a 24-well tissue culture plate and allowed to adhere over night in a 37° C. $CO_2$ cell culture incubator. Cells were washed with 0.5 ml Dulbecco's Phosphate Buffered Saline without Calcium or Magnesium (D-PBS no $Ca^{++}$ no $Mg^{++}$) and treated for one minute with Trypsin EDTA. The trypsin was aspirated off and the cells washed with 0.5 ml of D-PBS (no $Ca^{++}$ no $Mg^{++}$) and stained with 1 ml 0.2% Toluidine Blue-O in 10% Formalin to visualize the remaining cells. Positive clones were those that were still attached to the plate after a final wash to remove excess stain. Trypsinization revealed 5 clones, #4, 7, 12, 15 and 32, with significantly enhanced adhesion properties as compared to the parental 293-H cell line. See FIG. 3A.

Clones were transfected with pCMV•SPORT-βgal to determine transfection and expression characteristics (Sambrook, J., et al., "Assay for β-galactosidase in Extracts of Mammalian Cells," in *Molecular Cloning: A Laboratory Manual*, Cold Spring Harbor Press, Cold Spring Harbor, N.Y. Second Edition, (1989), p. 16.66). Cells were plated $2 \times 10^5$ cells per well in 24-well tissue culture plates and allowed to adhere over night in a 37° C. $CO_2$ cell culture incubator. Cells were transfected on duplicate plates with 0.8 µg pCMV•Sport β-galactosidase and 0–3 µl LipofectAMINE™ 2000. Twenty-four hours after transfection, cells were washed and either harvested for ONPG assay or stained using the X-gal stain protocol. See FIG. 3B.

Clones were frozen down, thawed and allowed to recover before the trypsinization and transfection and expression experiments were repeated to confirm the preferred phenotype. Clone #32 was determined to have the best adherence, transfection and expression characteristics and was sent for cell banking.

Twenty-two vials of Seed Cell Bank stocks were frozen down at $2.5 \times 10^6$ cells per vial. One vial was thawed and showed 97% viability upon thaw. *Mycoplasma* testing was performed and the results indicated no mycoplasma contamination. Virus testing was performed and the results indicated no viral contamination. Sterility testing was performed and the results indicated no adventitious agents were present.

Example 2

Confirmation of Adherence Characteristics

GIBCO® 293-H and 293 H MSR cells were plated on Costar® tissue culture treated 24-well plates and allowed to adhere overnight in a 37° C. 5% $CO_2$ cell culture incubator. Cells were treated as follows: cells were washed with 1 ml D-PBS (no $Ca^{++}$ no $Mg^{++}$) (D-PBS), incubated in 250 µl Versene 1:5000 (Invitrogen) for 5 minutes, the Versene removed and 250 µl trypsin added for 1 minute and removed. Cells were incubated with 1 ml D-PBS for 10 minutes. Cells were washed with 1 ml D-PBS the D-PBS removed and incubated in 250 µl trypsin for 1 or 2 minutes. Following the above treatments, the cells were stained with 0.05% Crystal Violet in PBS+10% Formalin. See FIG. 4. The GripTite™ 293 MSR cells remained attached after each treatment, even 10 minutes in trypsin, where the GIBCO® 293-H cells were washed from the plate after a few minutes in PBS.

Example 3

Confirmation of Transfection Characteristics

GIBCO® 293-H and 293 H MSR were plated on Costar® tissue culture treated 24-well plates and allowed to adhere overnight in a 37° C. 5% $CO_2$ cell culture incubator. Cells were transfected with 0.8 µg pCMV SPORT-βgal and 0–4 µl Lipofectamine™ 2000™. Cells were washed once in D-PBS and stained using the β-Gal Staining Kit (Invitrogen Corporation, Carlsbad, Calif.). The GripTite™ 293 MSR cells remained attached through the 7 wash staining protocol, where many GIBCO® 293-H cells were washed away. Both cell lines expressed β-galactosidase as measured by blue staining of cells. See FIG. 5, this figure also demonstrates the increased adherence of GripTite™ 293 MSR cells as compared to GIBCO® 293-H cells.

Example 4

Comparrison of Transfection Characteristics to Lysko 293 MSR

Lysko 293 MSR, GIBCO® 293-H and 293 H MSR were plated on Costar® tissue culture treated 24-well plates and allowed to adhere overnight in a 37° C. 5% $CO_2$ cell culture incubator. Cells were transfected with 0.8 μg pCMV SPORT-βgal and 0–5 μl Lipofectamine™ 2000™. Cells were washed once in D-PBS and harvested for ONPG assays. The GripTite™ 293 MSR and GIBCO® 293-H cells expressed similar amounts of β-galactosidase as measured ONPG, however the Lysko 293 MSR cells only produced one-fifth the amount of β-galactosidase. See FIG. 2.

Example 5

Cells Washed with Plate Washers

293-H and GripTite™ 293 MSR cells were plated in one row each on 5× Falcon tissue culture treated 96-well plates and allowed to adhere for 24 hours in a 37° C. 5% $CO_2$ cell culture incubator. Plates were washed using the same basic protocol in plate washers from three suppliers, the CCS Packard Plate-Wash™96/384, Molecular Devices Embla 96/384 Well Washer, and the Tecan PW-96. The wash protocol consisted of the removal of media, the addition of 100 μl D-PBS, and the removal of the D-PBS. The wash cycle was repeated three times with a final aspiration to remove all remaining D-PBS. Plates were stained with 0.05% Crystal Violet in PBS+10% Formalin. The media was removed from the no wash control plate and 100 μl D-PBS was carefully added to wash the cells before staining. The D-PBS was removed and the plate stained with 0.05% Crystal Violet in PBS+10% Formalin as above. In each case, more GripTite™ 293 MSR cells remained attached after each treatment than GIBCO® 293 H cells.

Cells Washed with Plate Washers (2)

To further show the utility of the MSR cell lines and to demonstrate that useful experiments can be performed using a plate washer, 293-H and 293 H MSR cells were plated as above, transfected and evaluated using a series of methods on parallel plates. Transfected cells were assayed for β-galactosidase expression using an ONPG assay and X-gal staining, Bradford assays were performed to show the protein recovery in each well, and an Alamar Blue MTT assay was performed to demonstrate a different type of assay that could be successfully performed using the MSR cells.

GIBCO® 293-H and 293 H MSR cells were plated in one row each of 5 Falcon tissue culture treated 96-well plates and allowed to adhere overnight in a 37° C. 5% $CO_2$ cell culture incubator. Cells were transfected with 0.3 μg pCMV•SPORT-βgal and 1 μl Lipofectamine™ 2000™. After 24 hours, plates were washed as above using the CCS Packard Plate-Wash™ 96/384 with either the slant-pin or the straight-pin wash head. To directly measure the cellular respiration in each well after washing, 100 μl Alamar Blue™ was added to each well using a 12-channel pipettor. Plates were read at A570 and A600 after 2 and 4 hours and the Alamar Blueυ reduction calculated Plates were harvested for ONPG and Bradford assays or X-gal stained. See FIG. 6.

To show that an enzymatic assay is more consistent in 293 H MSR cells after plate washing, β-galactosidase expression was measured. In the transfected cells, the parental 293-H cell line expressed somewhat more β-galactosidase than the 293 H MSR cell line (FIG. 6C), however the cells were easily disrupted and fell off of the plate during the media removal. Because the GIBCO® 293-H cells did not adhere as reliably, β-galactosidase expression was low under two of the three conditions. In addition, the reproducibility between wells was much lower in the GIBCO® 293-H cells as compared to the 293 H MSR cells; the error bars representing the standard deviation between 8 samples are much larger for the GIBCO® 293-H cells than the 293 H MSR cells.

The Alamar Blue™ Assay was difficult to perform in GIBCO® 293-H cells after plate washing. There were not enough cells remaining to accurately determine the concentration of Alamar Blue™ reduced. Even after washing with the straight-pin dispenser, there were enough 293 H MSR cells remaining in the wells to measure the concentration of Alamar Blue™ reduced. The more gentle no wash and slant-pin dispenser washes also resulted in acceptable average concentration of Alamar Blue™ reduced (FIG. 6D). Together these methods show that, although it may be possible to use the parental 293-H cells for some applications, the 293 H MSR is more reliable when the cells are exposed to the shear forces involved in plate washing. Using the GripTite™ 293 MSR cell line in these experiments resulted in more signal per well, smaller error per well and more robust and reliable results in each assay format.

Example 6

Packard MultiPROBE® II HTEX Manipulations

GIBCO® 293-H and 293 H MSR cells were plated in 6 wells per row on 4× Falcon tissue culture treated 96-well plates and allowed to adhere overnight in a 37° C. 5% $CO_2$ cell culture incubator. Cells were transfected with 0.3 μg pCMV•SPORT-βgal and 1 μl Lipofectamine™ 2000. Twenty-four hours after transfection, the media was removed from the wells and 100 μl Alamar Blue™ was added to each well using either a Packard MultiPROBE® II HTEX or a 12-channel pipettor. Plates were read at A570 and A600 after 2 and 4 hours and the Alamar Blue™ reduction calculated. The Alamar Blue™ was removed and the plates stained using either 0.05% Crystal Violet in PBS+10% Formalin or the β-Gal Staining Kit (Invitrogen Corporation, Carlsbad, Calif.). As was observed in each of the previous examples, the GripTite™ 293 MSR cells remained attached after where the GIBCO® 293-H cells did not. See FIG. 7.

Example 7

Generation of the Flp-In™ 293 MSR Stable Cell Line

The Flp-In™ 293 MSR cell line was generated by transfecting $9 \times 10^5$ 293 H MSR cells per well of a 6-well plate with 2 μg of pFRTlacZeo2 using LipofectAMINE™ 2000 (Invitrogen) in duplicate. Twenty-four hours post transfection, cells were trypsinized and transferred to 100 mm plates with 10 mL cell culture media and placed under 100 μg/mL Zeocin selection. After 10 to 35 days of antibiotic selection, 24 clones were picked and transferred to T75 flasks. For each clone, one vial of viable cells was frozen, and one pellet of cells was frozen at −80° C. for DNA Southern blot analysis.

Determination of Single Integration

Southern blots were conducted to identify clones with a single integration of the vector pFRTlacZeo2. Cell pellets were processed with the SNAP Whole Blood DNA Isolation kit (Invitrogen) to obtain genomic DNA. Two individual overnight digests of 15 µg of DNA were performed using either NcoI or BglII. DNA was electrophoresed overnight on an 0.8% agarose gel. Southern blots of the digested DNA were performed using Nytran SupPerCharge TurboBlotter™ (Schleicher & Schuell). Using the High Prime DNA labeling kit (Roche), 25 ng of a 1967 bp EcoRV lacZ gel-purified fragment was random primed labeled with $\alpha^{32}$P-dCTP. Membranes were hybridized overnight at 60° C. in QuikHyb™ (Stratagene) and washed according to the manufacturers instructions. The labeled membrane was exposed to film for several days at −80° C. with an intensifying screen. The appearance of a single band per lane on the blot identified seven possible single integrant clones #1, 2, 6, 10, 13, 15, and 17. See FIG. 8.

The pFRTlacZeo2 vector contains the lacZ gene, which encodes β-galactosidase allowing the extent of gene expression to be measured. If the vector is inserted into an active section of the genome, β-galactosidase expression levels will be higher and thus recombined open reading frames should also be expressed well. β-galactosidase activity was assayed using the Galacton Plus detection kit (Tropix) to select the highest expressing clone from the above clones. See FIG. 9. The clones with the highest β-galactosidase activity were 2, 10, and 17. High β-galactosidase activity suggests that the FRT site integrated in a transcriptionally active "hot spot".

A second Southern blot was conducted on clones 2, 10 and 17 to verify a single integrant. Again 15 µg of genomic DNA from clones 2, 10, and 17 were digested with BglII. This blot verified that clones 2 and 17 were single integrants. See FIG. 10.

Flp Dependant Integration

The Flp recombination transfection with LipofectAMINE™ 2000 was performed with pcDNA6/FRT/TO/CAT, transporting the gene to be flipped into the Flp-In™ 293 MSR cell line, and pOG44, expressing the Flp recombinase on a non-selectable plasmid, in a 1:9 ratio. Cells were plated at a density of $7\times10^5$ cells per well in 6-well plates. A total of 2 µg of the 1:9 DNA-mix was used with 6 µl of LipofectAMINE™ 2000 in a total of 400 µl Opti-MEM™. Twenty-four hours post transfection, the cells were washed and given fresh media. Forty-eight hours post transfection the cells were transferred to 100 mm plates and selected with 10 µg/ml blasticidin. Following 13 days of selection, 17 subclones were picked and transferred to 12-well plates, four days later 10 clones were transferred to 6-well plates.

Western Blots

Nineteen to twenty-one days after the subclones were picked, they were trypsinized, pelleted and frozen at −80° C. Lysates of 10 subclones were prepared using IGEPAL® CA-630 (Sigma, NP-40 replacement) lysis buffer. The proteins in the lysate (20 µg/lane) were separated on a 4–20% Novex® Tris-Glycine SDS-PAGE gel. Following electrophoresis, the proteins were transferred to a 0.45 µm nitrocellulose membrane. Western blotting was performed using a primary rabbit polyclonal antibody reactive to chloramphenicol acetyl transferase (CAT, 1:5000, Invitrogen) and the Western Breeze™ Chemiluminescence Kit (Invitrogen) with a secondary anti-rabbit antibody. Each clone showed a similar amount of CAT expression. See FIG. 11.

During Flp recombination the lacZ gene is cut at the frt site and the gene of interest is inserted. After a successful recombination, no galactosidase activity should be seen. β-galactosidase activity in the β-subclones was assayed as above to verify inactivation of the lacZ gene. All of the subclones have reduced levels of β-galactosidase when compared to the parental clone. See FIG. 12.

Twenty-eight vials of R&D Master stocks were frozen down at $1\times10^7$ cells per vial. One vial was thawed and showed 98% viability upon thaw. *Mycoplasma* testing was performed on the supernatant of the culture after 6 days in antibiotic-free media and the results indicated no *mycoplasma* contamination.

Example 8

Generation of the T-REx™ 293 MSR Stable Cell Line

The T-REx™ 293 MSR cell line was generated by transfecting $2\times10^5$ GripTite™ 293 MSR cells with 0.8 µg pTetR:Hyg and 2 µl LipofectAMINE™ 2000. Twenty-four hours post-transfection the cells were resuspended and diluted into 100 mm dishes at $2\times10^5$, $2\times10^4$, and $2\times10^3$ cells per plate. Twenty-four hours after dilution, the cell culture media (DMEM 10% FBS 1% MEM-NEAA) was replaced with media containing 600 µg/ml Geneticin and 200 µg/ml Hygromycin B. Distinct foci formed after 18 days of Hygromycin B selection. Those foci that adhered to the plate through two PBS washes and a 5 minute Versene 1:5000 incubation were picked and expanded as single clones.

Screening of T-REx™ 293 MSR Clones

Clones were pre-screened for tetracycline controlled expression of β-galactosidase by transfection with 0.320 µg pTetO β-gal and 1 µl LipofectAMINE™ 2000 in the absence of tetracycline. Forty-eight hours after transfection the cells were stained with X-gal, all clones that stained blue were discarded. The remaining clones were screened for adherence to tissue culture treated plastic and resistance to trypsinization as above. Those clones that did not appear blue after X-gal staining were expanded for further screening. See FIG. 13.

To evaluate the ability to induce expression of transiently transfected LacZ by addition of tetracycline, clones #2, 4, 6, 7, 13, and 14 were transfected with pTetO:βgal in the presence and absence of tetracycline. Clones were plated at $2\times10^5$ cells per well in a 24-well plate and allowed to adhere over night in a 37° C. $CO_2$ cell culture incubator. Cells were transfected with 0.8 µg pTetO:β-gal and 2 µl LipofectAMINE™ 2000. Cells were washed and either harvested for β-galactosidase assay or stained using the X-gal stain protocol 48 hours after transfection. β-galactosidase activity was assayed using the Galacton Plus detection kit (Tropix). Six clones were chosen for further characterization. See FIG. 14.

GIBCO® 293-H and GripTite™ 293 MSR cells and T-REx™ 293 MSR cells were plated in one row each on a Falcon tissue culture treated 96-well plate and allowed to adhere overnight in a 37° C. 5% $CO_2$ cell culture incubator. After 24 hours, plates were washed as above with a 12 channel pipettor. After 2 or 4 washes with 100 µl PBS, 100 µl Alamar Blue™ was added to each well. Plates were read at A570 and A600 after 2 and 4 hours and the Alamar Blue™ reduction calculated. As expected the GripTite™ 293 MSR and T-REx™ 293 MSR cells remained attached where the GIBCO® 293-H cells did not stay attached to the plate. See FIG. 15.

Tetracycline control was also evaluated compared to the T-Rex 293 cell line (Invitrogen). Cells were plated at $2 \times 10^5$ cells per well in a 24-well plate and allowed to adhere over night in a 37° C. $CO_2$ cell culture incubator. Cells were transfected with 0.8 μg pTetO:β-gal and 2 μl LipofectAMINE™ 2000. Cells were washed and either harvested for β-galactosidase assay or stained using the X-gal stain protocol 48 hours after transfection. β-galactosidase activity was assayed as above. The T-REx™ 293 MSR cells performed as well as the T-Rex 293 cells. See FIG. 16.

The clone with the most consistently low un-induced and high induced β-galactosidase activity was chosen for expansion and banking. Twenty-nine vials of Seed Cell Bank stocks were frozen down at $3.1 \times 10^6$ cells per vial. One vial was thawed and showed 87% viability upon thaw. *Mycoplasma* testing was performed and the results indicated no mycoplasma contamination. Virus testing was performed and the results indicated no viral contamination. Sterility testing was performed and the results indicated no adventitious agents were present.

Example 9

Confirmation of Adherence Characteristics in all MSR Cell Lines

In order to show that the GripTite™ 293 MSR cell line and its derivatives have similar adherence properties, the 293 MSR, Flp-In™ 293 MSR and T-REx™ 293 MSR cell lines were assayed for adherence to tissue culture treated plastic. Each MSR cell line was matched with a parental or similar cell line without the MSR gene, (i.e., 293 MSR with GIBCO® 293-H, Flp-In™ 293 MSR with Flp-In™ 293, and T-REx™ 293 MSR with T-REx™ 293). GIBCO® 293-H, 293 H MSR, T-REx™ 293, T-REx™ 293 MSR, Flp-In™ 293 and Flp-In™ 293 MSR were plated on Costar tissue culture treated 24-well plates and allowed to adhere over night in a 37° C. $CO_2$ cell culture incubator. Cells were treated as follows: cells were washed with 1 ml D-PBS no $Ca^{++}$ no $Mg^{++}$, the PBS removed, cells were then incubated in 250 μl Versene 1:5000 for 5 minutes, the Versene removed and 250 μl trypsin added for 1 minute and removed. Cells were incubated with 1 ml D-PBS (no $Ca^{++}$ no $Mg^{++}$) for 10 minutes. Cells were washed with 1 ml D-PBS (no $Ca^{++}$ no $Mg^{++}$), the D-PBS removed and incubated in 250 μl trypsin for 1 or 2 minutes. Following the above treatments the cells were stained with 0.05% Crystal Violet in PBS+10% Formalin.

In all cases, Versene 1:5000 incubation followed by trypsin treatment removed the cells from the tissue culture plate. However, the non-MSR cell lines detached from the plate after all other treatments (10 minute incubation in D-PBS, 1 minute trypsin, or 2 minutes trypsin) where the MSR cell lines did not, demonstrating a reduced dependence on calcium and magnesium for adherence and resistance to trypsin treatment. See FIG. 17.

Plate Washing Experiments

Plate washers are commonly used in automated procedures. The "wild-type" 293 cells line do not adhere to regular tissue culture treated plastic well enough to allow the use of plate washers. It is thus important to show that the GripTite™ 293 cell lines withstand the forces associated with using a plate washer.

GIBCO® 293-H, 293 H MSR, T-REx™ 293 MSR and Flp-In™ 293 MSR cells were plated at $2 \times 10^4$ cells per well in one row each on 3×96-well plates and allowed to adhere for 48 hours in a 37° C. $CO_2$ cell culture incubator. Plates were washed using a CCS Packard PlateWash™ 96/384. One plate was washed using a slant-pin dispensing attachment, one plate was washed using a straight-pin dispensing attachment and one plate was left untreated. The wash protocol consisted of the removal of media, the addition of 100 μl D-PBS (no $Ca^{++}$ no $Mg^{++}$), and the removal of the D-PBS (no $Ca^{++}$ no $Mg^{++}$); for each wash cycle this protocol was repeated three times with a final aspiration to remove all remaining D-PBS (no $Ca^{++}$ no $Mg^{++}$). Plates were stained with 0.05% Crystal Violet in PBS+10% Formalin.

In this experiment, the GIBCO® 293-H cells were partially removed from the plate during the media removal required for staining but were able to withstand the gentle wash cycle using the slant-pin dispenser; however, all cells were removed during washing with the straight-pin dispenser. Under all conditions, the MSR cells remained attached where the non-MSR cells did not. Because the GIBCO® 293-H cells do not adhere well in the absence of polylysine, it was difficult to remove media and wash the cells for staining without removing a large number of the cells; because of this, the 293-H no wash control wells appear less dense than the remaining cells. The no wash control plate shows holes in the 293 H MSR monolayer from pipette-tip damage, the slant-pin dispenser wash cycle the MSR monolayers are nearly perfect. There was a measurable loss of 293 H MSR cells from the wells washed with the straight-pin dispenser, however many cells were left attached. The MSR cells remained attached with very little cell loss, as compared to the non-MSR cells, after washing with the slant-pin dispensing head. The straight-pin dispensing head sheared all cells off of the plates at the point of dispensation; but, where the non-MSR cells were almost completely removed from the plate, the majority of the MSR cells remained attached. See FIG. 18.

It has been demonstrated that the 293 H MSR cell line adheres to tissue culture treated plastic after manipulations with a 12-channel pipettor, plate washers and a liquid handling robot. From FIG. 17, it is apparent that the 293 H MSR cell line is resistant to trypsinization, yet when desired a simple Versene incubation allows easy removal of the cells for passaging. FIGS. 2, 5 and 6 show that the 293 H MSR cell line has the high-efficiency, high-expression transfection characteristics of GIBCO® 293-H as well as adherence properties to withstand repeated manipulations of an X-gal stain protocol. PBS washes with a 12-channel pipettor and plate washers both dislodged a significant number of 293-H cells but not 293 H MSR cells (FIGS. 6, 7 and 17). In FIGS. 6 and 7 assays are performed following plate washing showing not only that the 293 H MSR cells remain attached to the plate, but also that the cells are viable. In addition, there is less variability in the Alamar Blue™ and ONPG assays when the 293 H MSR cell line is used as compared to 293-H. Finally, addition of the Alamar Blue™ substrate using a Packard MultiPROBE® II HTEX dislodged the majority of "wild type" GIBCO® 293-H cells while the 293 H MSR cells remained attached to the tissue-culture treated plate.

Example 10

Generation of the FreeStyle™ 293 Cell Line

In order to facilitate human biochemical expression, a subclone of HEK 293, an optimized media formulation and a transfection reagent for expression of biologically active materials in a scalable suspension format were developed. HEK 293-F cells were obtained from Robert Horlick at Pharmacopoeia. A fast-growing variant was isolated and adapted to growth in serum free suspension culture, unfortunately the media that the cells were adapted to does not allow transfection. Several fast growing clones were adapted into adherent culture. Sub-clones were isolated and screened for efficient transfection and high protein production. These cells, after adaptation, demonstrated characteristics of rapid growth and ease of transfection. This subclone was adapted into FreeStyle™ 293 Expression Medium and named FreeStyle™ 293 cells. The FreeStyle™ 293 cells are grown in suspension for ease of use and were not transfected with the MSR gene.

Expression of Reporter Proteins in FreeStyle™ 293 Cells

FreeStyle™ 293-F cells were maintained in an 8% $CO_2$ humidified tissue-culture incubator at 37° C. in FreeStyle™ 293 Expression Medium and subcultured every three to four days by seeding fresh media with $2–5 \times 10^5$ cells/ml. Transfections were performed as follows using pcDNA3.1/LacZ/V5-His for β-galactosidase expression, pcDNA5/FRT/lucA for luciferase expression, pcDNA4CAT for chloramphenicol acetyltransferase, and pTO EGF for Epidermal Growth Factor (EGF) expression. DNA was diluted as follows, 1 µg of DNA was diluted into 33 µl Opti-MEM Reduced Serum Medium (Opti-MEM®) (Invitrogen) per ml total culture volume, mixed gently and incubated for a total of 15 minutes. A high transfection efficiency transfection reagent, 293 fectin™ (Invitrogen) was gently mixed and 1–2 µl diluted into 33 µl Opti-MEM® per ml total culture volume, mixed gently and incubated for a total of 5 minutes. Diluted DNA was added to diluted 293 fectin™ and transfection complexes were allowed to form for 20–30 minutes. The total complex volume of 66 µl was added to $1 \times 10^6$ FreeStyle™ 293-F cells in 0.93 µl FreeStyle™ 293 Expression Medium. Cells were incubated in an 8% $CO_2$ humidified tissue-culture incubator at 37° C. on an orbital shaker platform rotating at 125 rpm. Transgene expression was monitored at 24 hour intervals to determine appropriate harvest times. Larger protocols are scalable from this protocol. Three ml cultures with $3 \times 10^6$ FreeStyle™ 293 cells were transfected with a 200 µl transfection complex composed of 3 µg plasmid DNA and 3–5 µl 293 fectin™ in Opti-MEM®. For cultures with a 30 ml final volume, 30 µg plasmid DNA and 30–50 PI of 293 fectin™ were each diluted into 1 ml Opti-MEM®, mixed after an appropriate incubation to create the transfection complexes, and 2 ml complexes were added to $3 \times 10^7$ FreeStyle™ 293 cells in 28 ml FreeStyle™ 293 Expression Medium for a final volume of 30 ml in 250 ml disposable Erlenmeyer tissue culture flasks.

Several reporter systems were used to demonstrate utility of the FreeStyle™ 293 Expression System. Cells were transfected using the protocol outlined above. Forty-eight hours after transfection, cell lysates were collected and assayed for expression of the appropriate reporter. For β-galactosidase, the ONPG assay was used. For luciferase, the Promega Luciferase Assay System was used. EGF expression was measured using the Quantikine® human EGF Immunoassay from R&D systems. Chloramphenicol Acetyl-transferase expression was measured using the CAT Elisa system from Roche. FIG. 24 shows expression levels of human Epidermal Growth Factor, Chloramphenicol Acetyltransferase, luciferase and β-galactosidase. All proteins were expressed from the CMV. Expression levels are dependant on both the vector system and the protein of interest. The variability of expression levels seen in FIG. 24 reflects both differences in the expression vectors and differences in the expression levels of different proteins in this system.

Expression in Transiently Transfected 30 ml FreeStyle™ 293 Cultures

Figure 21:
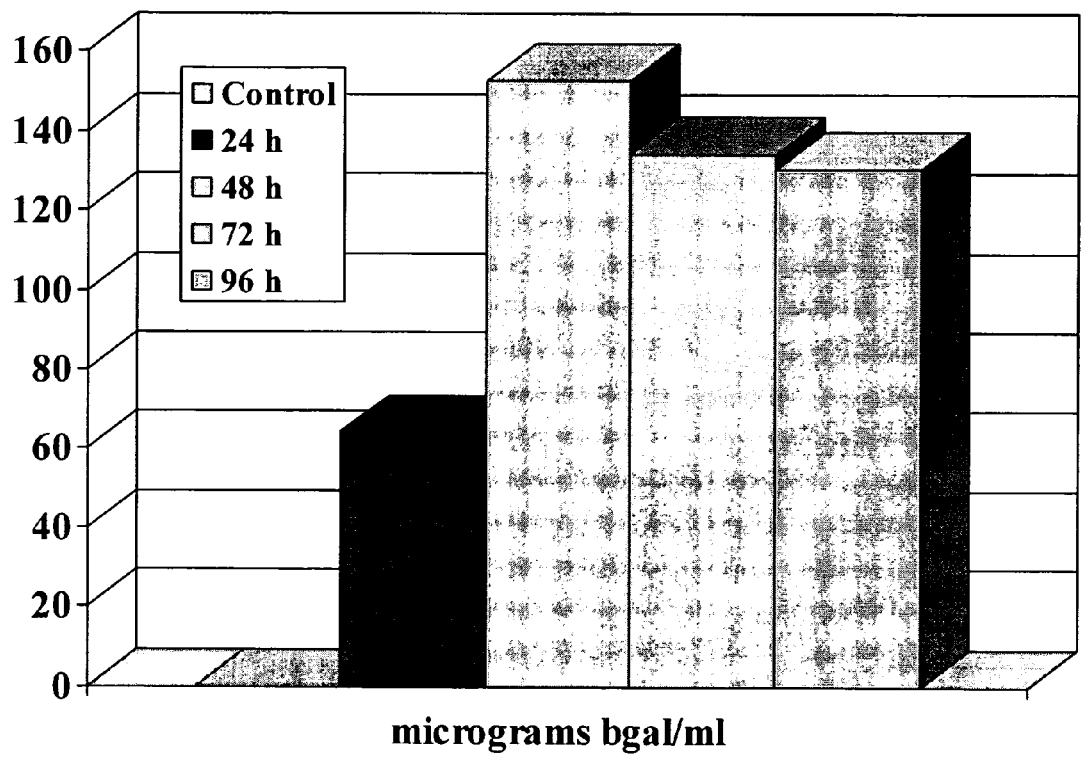
FIG. 21 shows expression of β-galactosidase in a shake flask format harvested at 1, 2, 3 and 4 days after transfection.
Figure 22:
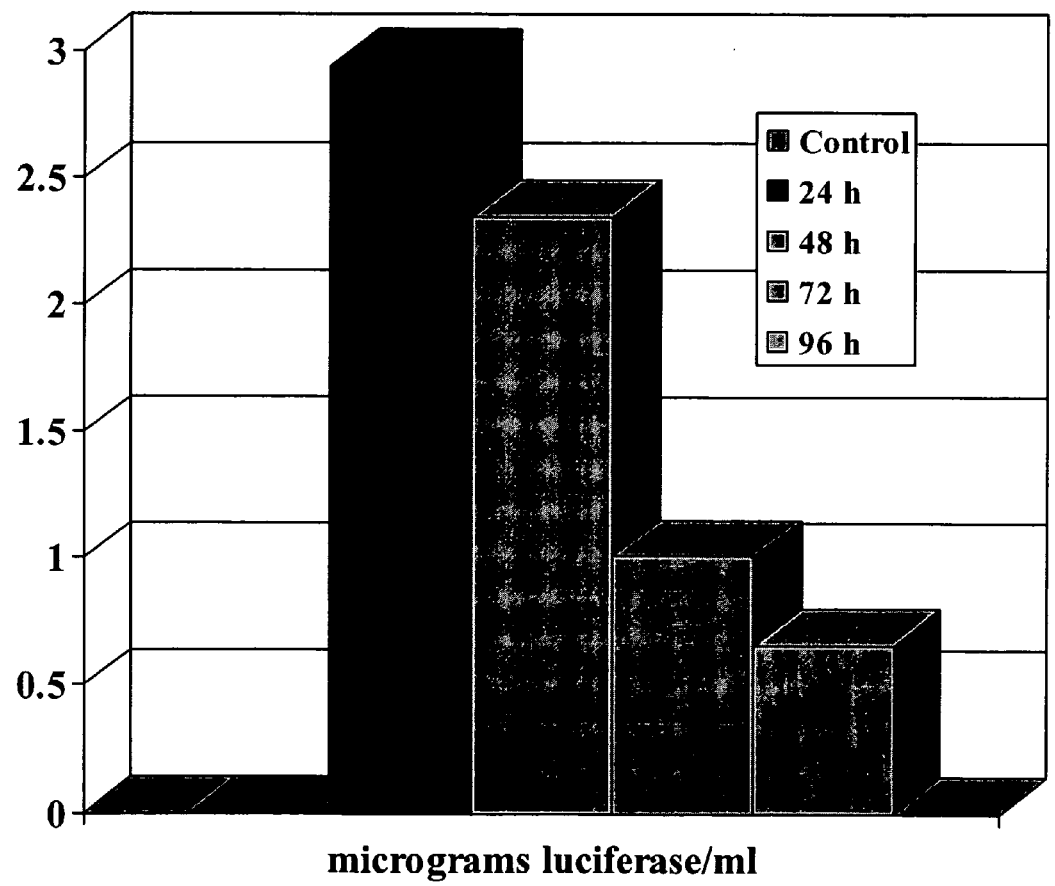
FIG. 22 shows the expression of luciferase in a shake flask format harvested at 1, 2, 3 and 4 days after transfection.

FreeStyle™ 293 cells were transfected as above in 30 ml cultures using pCMV Sport β-gal and pCMV Sport luc. Aliquots were taken at 0, 24, 48, 72, and 96 hours and assayed for β-galactosidase or luciferase activity. FIGS. 21 and 22 show expression of these two reporter proteins over time in Freestyle™ 293 cells. The mRNA that encodes luciferase and the luciferase protein are both less stable than those for β-galactosidase, which is reflected in the time course of expression. The luciferase expression started at a peak at 24 hours and fell over the following 3 time points where the β-galactosidase expression peaked at 48 hours and slowly fell over the next 2 time points.

Bioreactor-Scale Growth of FreeStyle™ 293-F Cells

Because most suspension cell culture is done in bioreactors it was important to look at transfection of FreeStyle™ 293 cells in this format. In order to reduce shear forces that decrease cell viability, turbine impellers were replaced with one pitched-blade impeller and the baffle plates were removed. FreeStyle™ 293-F cells were expanded in shaker or spinner cultures until there were enough cells to seed the bioreactor at the minimal working volume with $2–5 \times 10^5$ cells/ml in FreeStyle™ Expression Medium. The appropriate bioreactor conditions were 37° C., pH 7.3, 50% dissolved $O_2$ and a mix speed of 90–100 rpm. If the viability dropped below 90%, the impeller speed was reduced, the cultures were checked for contamination and the pH and nutrient levels were confirmed using independent methods to ensure that the bioreactor sensors were reading accurately. Two to four days after seeding the culture, the glucose and glutamine levels were checked. When glucose levels reached 2 g/l, the culture was supplemented back to 4.5 µl and when L-glutamine levels reached 200 mg/l, the culture was supplemented back to 584 mg/l with L-glutamine or GlutaMAX™-I Supplement (Invitrogen).

Transfection of FreeStyle™ 293 Cells in Bioreactor Format

Figure 23:
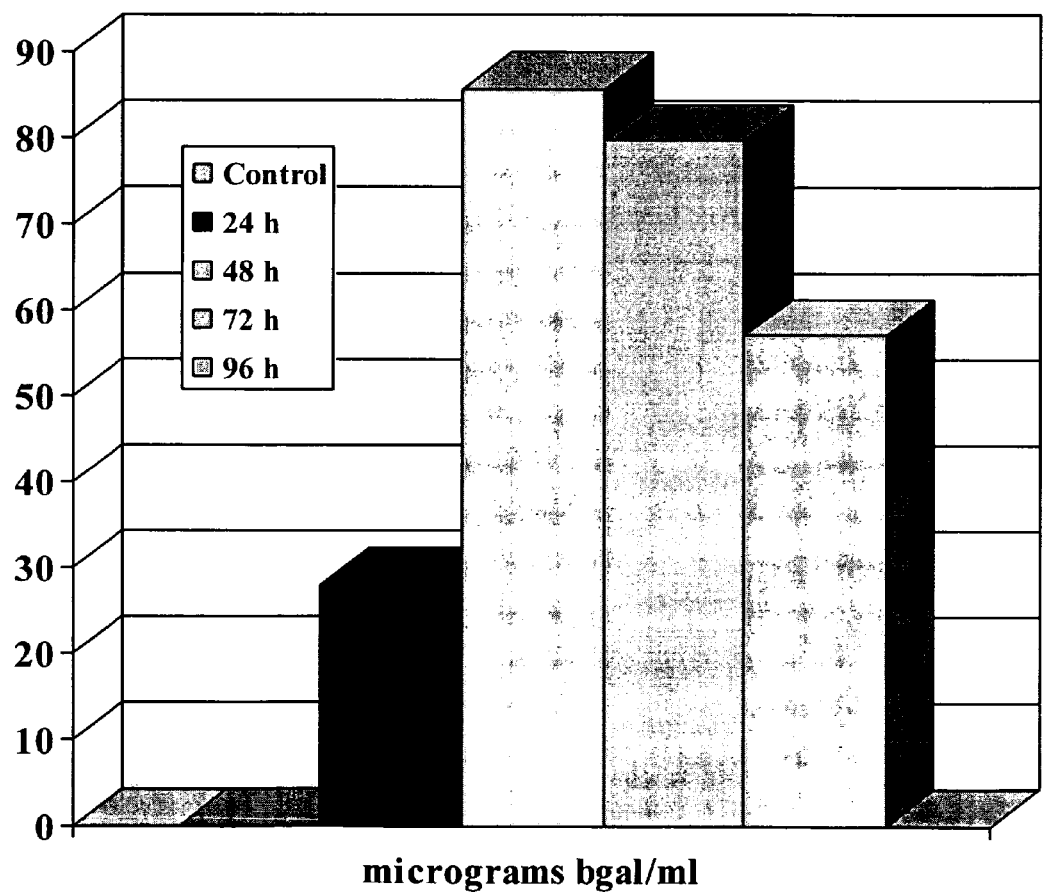
FIG. 23 shows the expression of β-galactosidase in a 1 liter bioreactor format harvested at 1, 2 and 4 days after transfection.

Several days before transfection, a 5 liter Celligen Bioreactor was seeded with $2–5 \times 10^5$ cells per ml in a single cell suspension. The day of transfection, cells were counted and suspended at $3.8 \times 10^9$ cells in 3.55 liters medium. The transfection complex was made as follows: 3.8 mg of plasmid DNA was diluted into 125.5 ml Opti-MEM®, and incubated for a total of 15 minutes. Five ml of 293 fectin™ was diluted into 125.5 ml Opti-MEM®, and incubated for a total of 5 minutes. The diluted DNA was added to the diluted 293 fectin™ and transfection complexes were allowed to form for 20–30 minutes. The total complex volume of 251 ml was added to the bioreactor. Nutrient levels were monitored and the culture supplemented as necessary. β-gal expression was monitored at 24 hour intervals using the ONPG assay. FIG. 23 shows the expression of β-galactosidase at 24, 48, 72 and 96 hours after transfection.

Scalability of the FreeStyle™ 293 Expression System

Figure 20:
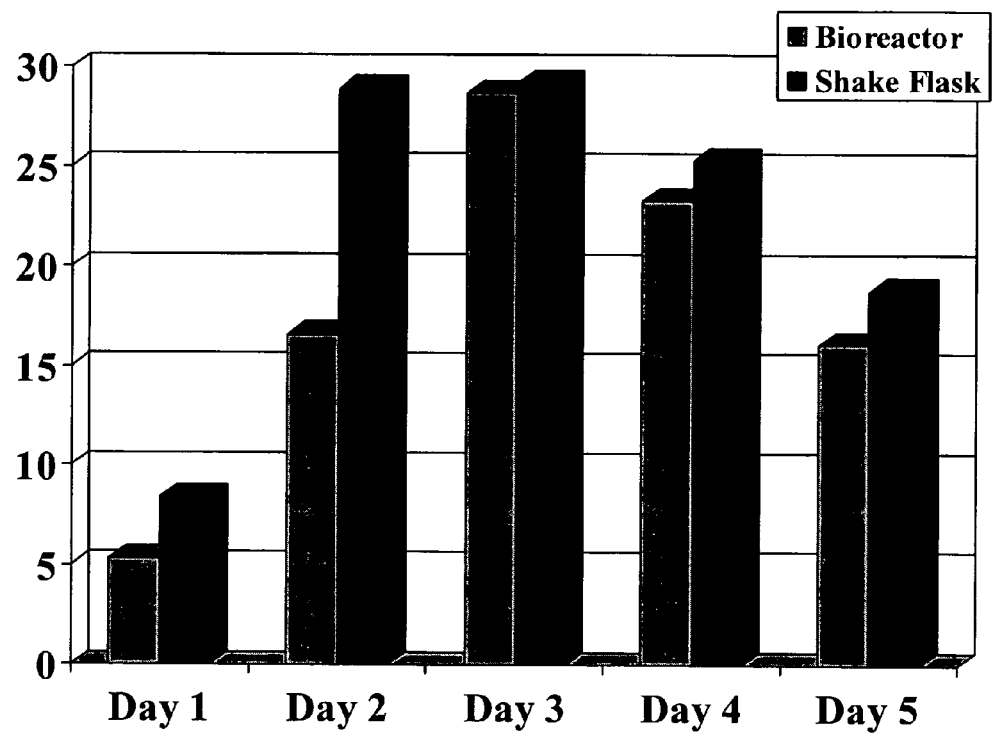
FIG. 20 shows expression of β-galactosidase in both a bioreactor and a shake flask format.

When scaling up from one expression system to another it is common to see significant differences in product yield. The FreeStyle™ 293 cells allow simple scale up from small to large volumes without the need to optimize conditions for different formats and without significant differences in protein yield. FIG. 20 shows expression of β-galactosidase in FreeStyle™ Cells in both a 30 ml shaker flask and a 5 liter bioreactor. See protocols for cell culture and transfection above. Although expression in the 30 ml flask was greater during the first 48 hours, by Day 3 both systems were producing the same amount of protein per ml total culture.

Example 11

Generation of the Simian Virus SV40 Large T Antigen in GIBCO® 293-F Cells

The simian virus SV40 large T antigen (SV40 TAg) gene was transfected into GIBCO® 293-F cells using pCMVSPORT6Tag.neo(A-B). This vector has had the SV40 origin of replication modified such that it is not capable of replicating in the presence of the SV40 TAg. The SV40 TAg is expressed from the CMV promoter. The neo gene, which confers resistance to the antibiotic Geneticin®, is expressed from a modified SV40 origin of replication promoter. Forty-eight clones were isolated after Geneticin® selection. Geneticin® resistant clones were tested for enhanced adherence to tissue culture plastic and permissiveness to transfection/expression.

Clones were screened for the presence of the simian virus large T antigen (SV40 TAg) using an Elisa. Clones were plated in a 96-well Elisa plate and allowed to adhere over night in a 37° C. $CO_2$ cell culture incubator. The media was removed and the cells were washed then lysed and frozen. The plates were thawed overnight to allow complete binding of the antigen to the plate. The plate was washed and an anti-SV40 TAg-Biotin antibody was added. The plate was washed and a strep-avidin —HRP conjugate was added. The plate was washed again and the substrate was added for visualization of the presence of the SV40 TAg. The clones with the highest expression levels of the SV40 TAg were expanded and frozen down for further testing. The positive clones were transiently transfected with pCMVSPORT β-gal neo with and without the SV40 origin of replication to measure the ability of the vector to amplify in the presence of the SV40 TAg. Clones number 38 and 42 had the greatest degree of amplification. These clones were then used to make recombinant virus.

Expression of the SV40 large T antigen was confirmed by western blot analysis. See FIG. 25. Total cell lysates were prepared using NP40 lysis buffer (Igepal CA636, Sigma) and the protein (20 μg/lane) were separated on a 4–20% Novex® Tris-Glycine gel. Following electrophoresis, the proteins were transferred to nitrocellulose. Western blotting was performed using the Western Breeze™ Chemiluminescence Kit (Invitrogen), using anti-large T antigen mouse monoclonal antibody (2 μg/ml, PharMingen). In comparing 293FT, 293A and T-Rex 293 only the 293FT cell line expressed the SV40 TAg.

Clones were plated $5\times10^6$ cells per 100 mm plate. Twenty-four hours later, the culture medium was replaced with 5 ml OptiMem/10% FBS and cells were co-transfected, as follows. 12 μg DNA total, at a mass ratio of 1:1:1:1 pRRL6/V5/gene:pMDLgpRRE:pRSV/REV:pMD2-VSVG (3 μg of each DNA) was mixed with 1.5 ml of OptiMem™ media. In a separate tube, 36 μl of LipofectAMINE™ 2000 was mixed with 1.5 ml of OptiMem™ media. After a 5-minute incubation, the two mixtures were combined and incubated for an additional 20 minutes. At the completion of the incubation, the transfection complex was added to the cells dropwise and the culture plate was gently swirled to mix. The following day the transfection complex was replaced with complete medium (DMEM, 10% FBS, 1% penicillin/streptomycin, L-glutamine and non-essential amino acids). Forty-eight hours post transfection, virus-containing supernatants were harvested, centrifuged at 3000 rpm for 15 minutes to remove dead cells, and placed in cryovials in 1 ml aliquots. Titers were performed on fresh supernatants (see below) and the remaining viral aliquots were stored at −80° C.

Viral Titering and Transduction

To titer recombinant virus, HT1080 cells were seeded at $2\times10^5$ cells per well in 6-well plates the day before transduction. Ten-fold serial dilutions of viral supernatant ranging from $10^{-2}$ to $10^{-6}$ were prepared. The dilutions were mixed by gentle inversion and added to cells. One well served as an untransduced control (mock) and the remaining five wells contained 1 ml each of the viral dilutions. Six μg/ml polybrene was added to each well. The plate was gently swirled to mix. The following day, the medium was replaced with complete medium. Forty-eight hours post transduction, the cells were placed under 10 μg/ml blasticidin selection (Invitrogen). After 10 to 12 days selection, resulting colonies were stained with crystal violet: A 1% crystal violet solution was prepared in 10% ethanol. Each well was washed with 2 ml PBS followed by incubation in 1 ml crystal violet solution for 10 minutes at room temperature. Excess stain was removed and followed by two 2 ml PBS washes. Colonies visible to the naked eye were counted to determine the viral titer of the original supernatants. In FIG. 38, colonies were countable in the $10^{-5}$ and $10^{-6}$ dilutions (46 and 5, respectively) resulting in a final titer of $4.8\times10^6$ (average of $46\times10^5$ and $5\times10^6$). The clone that resulted in the highest viral titer was banked.

R&D Master Cell stocks were frozen down at $1\times10^7$ cells per vial. One vial was thawed and showed 97% viability upon thaw. *Mycoplasma* testing was performed and the results indicated no mycoplasma contamination.

Example 12

Production of Recombinant Lentiviral Vectors Using the 293FT Cell Line of the Invention Confirmation of the Expression Properties of the Transfer Vectors Used to Make Recombinant *Lentivirus*.

Figure 28A:
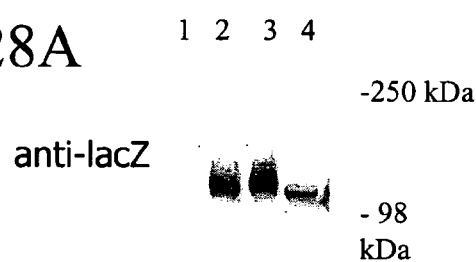
FIGS. 28A and 28B show the results of a Western blot of COS-7 cells transfected with recombinant gene transfer vectors and an expression vector control then stained with anti-lacZ antibody (FIG. 28A) and anti-V5-antibody (FIG. 28B).
Figure 28B:
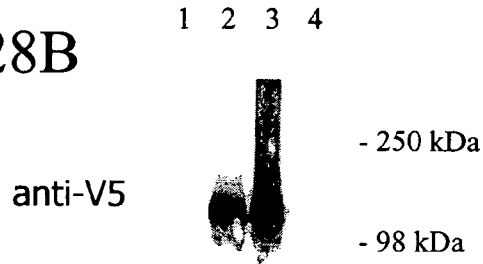

To verify protein expression and the functionality of the V5 epitope tag, the lacZ ORF (with or without a stop codon) was Gateway™ cloned into pRRL6/V5-DEST. The resulting attB expression clones were transiently transfected into COS cells and analyzed by anti-β-galactosidase and anti-V5 western blotting (FIGS. 28A and 28B). Compared to pcDNA3.1/V5His/lacZ, pRRL6/V5-GW/lacZ expressed equally well with and without the V5 epitope tag. In addition, lacZ(no stop) resulted in an efficiently expressed V5-tagged fusion protein (lane 3).

Virus Production Optimization

An effective time-course for production is shown in FIG. 29A. This protocol includes high density plating of the 293FT cells of the invention at $5\times10^6$ cells per 100 mm plate and transfection using the optimal lipid to DNA ratio using LipofectAMINE™ 2000. In addition, viral supernatants can be harvested either 2 or 3 days post transfection with minimal differences in viral yield. Presumably, the short half-life of the virus in culture media at 37° C. negates any advantage of viral accumulation over one extra day.

It is known in the art that the size of an inserted gene of interest can affect viral titer. Three different genes were Gateway™ cloned into pRRL6/V5-DEST (lacZ, CAT and protein kinase C) and one gene was directionally TOPO® cloned (GFP). Viral production was compared between these four gene-containing vectors and an empty vector, pRRL6/V5. See FIG. 29B. Averages from three independent experiments showed that the empty vector yielded the highest viral titer (average $1.4 \times 10^7$ cfu/ml), while the largest insert (lacZ) yielded the lowest titers (average $4.7 \times 10^5$ pfu/ml).

Inserted genes of intermediate size (GFP, CAT and PKC) yielded titers somewhere in between ($4 \times 10^6$, $9 \times 10^6$ and $3 \times 10^6$; respectively). These data indicated that both the Gateway™ and TOPO® versions of these vectors produce viral supernatants that easily exceed the target titer of $10^5$, even with the large lacZ gene. The wild type HIV-1 genome is approximately 10 kb and the elements present in pRRL6/V5 vectors add up to 3.7 kb. Therefore, the theoretical gene-packaging limit is approximately 6 kb.

Viral Gene Delivery and Expression

The ability of the lentiviral vectors to deliver and express a variety of genes was further investigated. To confirm the above results, and to verify that a functional V5 epitope tag was efficiently added to the expressed proteins, cell lysates were prepared from HT1080 cells stably transduced with either the lacZ, CAT, GFP or protein kinase C viruses. Transduced cells were selected with 10 µg/ml blasticidin for ten days. Total cell lysates were prepared using NP40 lysis buffer (Igepal CA636, Sigma) and the samples (20 µg/lane) were separated on a 4–20% Novex® Tris-Glycine gel. Following electrophoresis, the proteins were transferred to nitrocellulose. Western blotting was performed using the Western Breeze™ Chemiluminescence Kit (Invitrogen), anti-V5 mouse monoclonal antibody (1:2000 dilution, Invitrogen).

All four proteins are efficiently expressed and properly fused to a detectable V5 epitope. In addition, delivery and efficient expression of protein kinase C (a "relevant" gene, i.e., not a common test gene, e.g., lacZ, GFP or CAT) indicates the robustness and broad applicability of this virus production system. See FIG. 30.

To look at the ability of recombinant *Lentivirus* produced in 293FT cells of the invention to produce functional protein, HT1080 cells were transduced with either Gateway™ generated RRL6/V5-G/lacZ or TOPO® generated RRL6/V5-dT/GFP. Stably transduced cells were selected with blasticidin and analyzed by either X-gal staining or GFP fluorescence. See FIGS. 31A-31C. Both Gateway™ lacZ and dTOPO® GFP vectors efficiently generated heterogeneous pools of stably transduced cells in which nearly 100% of the cells expressed the heterologous gene. In addition to HT1080, HeLa and CHO cells have been stably transduced with similar efficiencies and levels of gene expression.

Gene Expression is Correlated to MOI

Theoretically, the multiplicity of infection (MOI=number of virus per cell) should correlate with gene delivery and expression. To investigate this, HT1080 cells were transduced in duplicate at various MOIs, ranging from 0.05 to 1. See FIG. 32. Forty-eight hours post transduction, cells were either X-Gal stained (panel A) or cell lysates were harvested for quantitation of β-galactosidase activity (panel B). As the X-Gal staining indicates, an increasing number of cells express α-galactosidase as the MOI increases. At an MOI of 1, greater than 80% of the cells express α-galactosidase. At higher MOIs (e.g. MOI 5), 100% of the cells were transduced. When cell lysates were analyzed for β-galactosidase activity, a near-linear dose response was observed as the MOI increased from 0.05 to 1 (panel B). At higher MOIs (e.g. MOI 5), the β-galactosidase activity continues to increase, but graph tends to flatten out.

Long-Term Gene Expression from Recombinant Lentiviral Vectors Produced in the 293FT Cell Line of the Invention HT1080 cells were transduced with either the RRL6/V5-GW/lacZ *lentivirus* or the rKAT6/V5-GW/lacZ retrovirus and stably selected with blasticidin. Cultures were maintained in blasticidin and were X-Gal stained at 10 days and 6 weeks post transduction. See FIG. 35. No loss of gene expression was observed over 6 weeks in culture, indicating that lentiviral gene delivery is stable and gene expression is persistent even at 6 weeks post transduction.

Example 13

Transduction of Growth Arrested Cells with Recombinant *Lentivirus* Produced in the 293FT Cells of the Invention.

Lentiviral Transduction of Non-Dividing Cells

One of the key advantages of *lentiviruses* over traditional retroviruses is that they are capable of stably transducing non-dividing cells. This significantly expands the potential tranducible target cells to include: 1) growth- or drug-arrested cells in culture, 2) non-dividing primary cell cultures, and 3) animals/tissues. To verify that our lentiviral vectors could perform under these conditions, three different approaches were tested.

Drug-Arrested Cells

Actively-growing cells in culture can be arrested at specific phases of the cell cycle using a variety of drugs. This approach is widely used in cell cycle analysis and tumor biology. One commonly used drug, aphidicolin, reversibly binds to DNA polymerase delta and is used to arrest cells at the G1/S transition (Seki 1980). To test the activity of our lentiviral vectors under conditions of cell cycle arrest, we transduced aphidicolin-blocked HT1080 cells with RRL6/V5-GW/lacZ virus. As controls, similarly blocked cells were transduced with a traditional Moloney-based retrovirus carrying the same lacZ gene (rKAT6/V5-GW/lacZ virus). Virus was applied to either actively growing cells or aphidicolin-arrested cells at an MOI of 1, in duplicate. Forty-eight hours post transduction, β-galactosidase activity was measured, see FIG. 33A. Both retrovirus and *lentivirus* were capable of transducing actively growing cells, but only the lentiviral vector was capable of transducing the non-dividing culture.

Quiescent Primary Cells

Our second approach was to apply the lentiviral vectors to non-dividing primary human cultures. A low-passage primary human foreskin fibroblast culture was plated into 6-well format and allowed to grow to confluence. Primary fibroblasts are strongly contact inhibited and can be maintained for many weeks arrested in quiescence ($G_0$) when maintained as a confluent culture. Both *lentivirus* (RRL6/V5-GW/lacZ) and retrovirus (rKAT6/V5-GW/lacZ) were applied to confluent quiescent primary fibroblasts and forty-eight hours post transduction cultures were X-Gal stained. See FIG. 33B. Similar to the results in aphidicolin-arrested cells, only the lentiviral vector appeared capable of transducing non-dividing cells. Approximately 50% of the quiescent primary cells were transduced at an MOI of 1.

Post-Mitotic Primary Neurons

Neuronal research is one area where lentiviral vectors can offer significant advantages over other gene transfer methods. Neuronal cultures are typically non-dividing, "post-mitotic" cells that transfect poorly. Traditional Moloney retroviruses are not useful for these applications because the cells never go through mitosis. Lentiviral vectors are one solution to overcome these hurdles.

Primary, post-mitotic rat neuronal tissues (cortical and hippocampal) were processed and plated. Four days after plating, cells were tranduced at an MOI of 1 with either RRL6/V5-GW/lacZ *lentivirus* or rKAT6/V5-GW/lacZ retrovirus. Three days post-transduction, cultures were stained for β-galactosidase. See FIG. 34. All wells transduced with the lentiviral vectors stained blue, with approximately 50% of the cells expressing detectable β-galactosidase. Conversely, wells transduced with the rKAT retrovirus did not show any β-galactosidase expression. These results indicated that the *lentiviruses* effectively transduced post-mitotic neurons of either cortical or hippocampal origin.

REFERENCE LIST

Baek et. al., *Hum. Gene Ther.* 12:1551–1558 (2001)
Biosafety in *Microbiological and Biomedical Laboratories*, 4th Ed., Centers for Disease Control
Buchschacher et. al., *Blood* 95:2499–2504 (2000)
Dull, et. al., *J. Virol.* 72:8463–8471 (1998)
Lewis et. al., *J. Virol.* 68:510–516 (1994)
Miller et. al., *BioTechniques* 7:980–990 (1989)
Miller et. al., *Mol. Cell. Biol.* 10:4239–4242 (1990)
Mochizuki et. al., *J. Virol.* 72:8873–8883 (1998)
Naldini et. al., *The Development of Human Gene Therapy*, Cold Spring Harbor Laboratory Press, (1999), pp. 47–60
Naldini et. al., *Proc. Natl. Acad. Sci. USA* 93:11382–11388 (1996)
Park et. at., *Mol. Ther.* 4:164–173 (2001)
Peng et. al., *Gene Ther* 8:1456–1463 (2001)
Seki et. al., *Biochem Biophys Acta* 610:413 (1980)
Yee et. al., *Proc. Natl. Acad. Sci. USA* 84:5197–5201 (1987)
Yee et. al., *Proc. Natl. Acad. Sci. USA* 91:9564–9568 (1994)
Yu et. al., *Proc. Natl. Acad. Sci. USA* 83:3194–3198 (1986)
Zufferey et. al., *J. Virol.* 72:9873–9880 (1998).

Having now fully described the present invention in some detail by way of illustration and example for purposes of clarity of understanding, it will be clear to one of ordinary skill in the art that the same can be performed by modifying or changing the invention within a wide range of similarly working conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A cell line selected from the group consisting 293-H MSR deposited with the American Type Culture Collection (ATCC) as accession number PTA-5078, Flpin MSR deposited with the ATCC as accession number PTA-5076 and 293 MSR test:R Hyg deposited with the ATCC as accession number PTA-5079.

2. The cell line of claim 1, wherein the cell line is Flpin MSR deposited with the ATCC as accession number PTA-5076.

3. The cell line of claim 1, wherein the cell line is 293 MSR tet:R Hyg deposited with the ATCC as accession number PTA-5079.

4. The cell line of claim 1, wherein the cell line is 293-H MSR deposited with the ATCC as accession number PTA-5078.

5. The cell line of claim 1, wherein the cell line is transfected with a DNA molecule.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Homo sapiens

<400> SEQUENCE: 1
gaaccatgga gcagtgggat cactt                                           25

<210> SEQ ID NO 2
<211> LENGTH: 54
<212> TYPE: DNA
<213> ORGANISM: Homo sapiens

<400> SEQUENCE: 2
ggggacaagt ttgtacaaaa aagcaggctg aaccatggag cagtgggatc actt          54

<210> SEQ ID NO 3
<211> LENGTH: 24
<212> TYPE: DNA
<213> ORGANISM: Homo sapiens

<400> SEQUENCE: 3
tgcattataa agtgcaagtg actc                                            24

<210> SEQ ID NO 4
<211> LENGTH: 53
<212> TYPE: DNA
<213> ORGANISM: Homo sapiens

```
<400> SEQUENCE: 4
ggggaccact ttgtacaaga aagctgggtt gcattataaa gtgcaagtga ctc        53
```